US007655785B1

(12) United States Patent
Bentwich

(10) Patent No.: US 7,655,785 B1
(45) Date of Patent: Feb. 2, 2010

(54) BIOINFORMATICALLY DETECTABLE GROUP OF NOVEL REGULATORY OLIGONUCLEOTIDES AND USES THEREOF

(75) Inventor: Itzhak Bentwich, Kfar Daniel (IL)

(73) Assignee: Rosetta Genomics Ltd., Rehovot (IL)

( * ) Notice: Subject to any disclaimer, the term of this patent is extended or adjusted under 35 U.S.C. 154(b) by 666 days.

(21) Appl. No.: 10/708,953

(22) Filed: Apr. 2, 2004

Related U.S. Application Data

(63) Continuation-in-part of application No. 10/708,204, filed on Feb. 16, 2004, and a continuation of application No. 10/707,980, filed on Jan. 29, 2004, and a continuation-in-part of application No. 10/707,975, filed on Jan. 29, 2004, now abandoned, and a continuation-in-part of application No. 10/707,147, filed on Nov. 24, 2003, and a continuation-in-part of application No. PCT/IL03/00970, filed on Nov. 16, 2003, which is a continuation of application No. 10/604,985, filed on Aug. 29, 2003, now abandoned, which is a continuation-in-part of application No. 10/651,227, filed on Aug. 29, 2003, which is a continuation of application No. 10/605,924, filed on Aug. 29, 2003, which is a continuation-in-part of application No. 10/649,653, filed on Aug. 28, 2003, which is a continuation of application No. 10/605,923, filed on Aug. 28, 2003, which is a continuation-in-part of application No. 10/604,926, filed on Aug. 27, 2003, which is a continuation of application No. 10/345,201, filed on Jan. 16, 2003, which is a continuation-in-part of application No. 10/321,503, filed on Dec. 18, 2002, which is a continuation-in-part of application No. 10/310,914, filed on Dec. 6, 2002, which is a continuation-in-part of application No. 10/293,338, filed on Nov. 14, 2002, which is a continuation of application No. 10/604,727, filed on Aug. 13, 2003, and a continuation of application No. 10/604,726, filed on Aug. 13, 2003.

(60) Provisional application No. 60/468,251, filed on May 7, 2003.

(51) Int. Cl.
| C12N 15/00 | (2006.01) |
| A61K 31/70 | (2006.01) |
| C07H 21/04 | (2006.01) |

(52) U.S. Cl. .................. 536/24.1; 536/23.1; 536/24.3; 536/24.5; 435/320.1; 514/44

(58) Field of Classification Search ........................ None
See application file for complete search history.

(56) References Cited

U.S. PATENT DOCUMENTS

| 6,573,099 | B2 | 6/2003 | Graham |
| 2002/0086356 | A1 | 7/2002 | Tuschl et al. |
| 2002/0150891 | A1* | 10/2002 | Hood et al. .................. 435/6 |
| 2003/0108923 | A1 | 6/2003 | Tuschl et al. |
| 2003/0228691 | A1 | 12/2003 | Lewis et al. |
| 2004/0053411 | A1 | 3/2004 | Cullen et al. |

FOREIGN PATENT DOCUMENTS

| WO | WO 01/68836 | 9/2001 |
| WO | WO 01/75164 | 10/2001 |
| WO | WO 02/44321 | 6/2002 |
| WO | WO 02/094185 | 11/2002 |
| WO | WO 03/029459 | 4/2003 |
| WO | WO 03/070884 | 8/2003 |
| WO | WO 03/070903 | 8/2003 |
| WO | WO 03/070918 | 8/2003 |
| WO | WO 03/074654 | 9/2003 |
| WO | WO 2004/009779 | 1/2004 |

OTHER PUBLICATIONS

John, B., et al. (2004) Human MicroRNA Targets. PLoS Biology v.2(22):1862-1879.*
Lee, R. C., R. L. Feinbaum and V. Ambros. The *C. elegans* heterochronic gene lin-4 encodes small RNAs with antisense complementarity to lin-14 Cell Dec. 3, 1993 843-854 75.
Wightman, B., I. HA and G. Ruvkun. Posttranscriptional regulation of the heterochronic gene lin-14 by lin-4 mediates temporal pattern formation in *C. elegans* Cell Dec. 3, 1993 855-862 75.
Gallinaro, H., L. Domenjoud and M. Jacob. Structural study of the 5' end of a synthetic premessenger RNA from adenovirus. Evidence for a long-range exon-intron interaction J Mol Biol Jul. 15, 1994 205-225 240.
Lu, C. and R. Bablanian. Characterization of small nontranslated polyadenylylated RNAs in vaccinia virus-infected cells Proc Natl Acad Sci U S A Mar. 5, 1996 2037-2042 93.
Crawford, E. D., E. P. Deantoni, R. Etzioni, V. C. Schaefer, R. M. Olson and C. A. Ross. Serum prostate-specific antigen and digital rectal examination for early detection of prostate cancer in a national community-based program. The Prostate Cancer Education Council Urology Jun. 1996 863-869 47.

(Continued)

*Primary Examiner*—Sean R McGarry
*Assistant Examiner*—Jennifer Pitrak
(74) *Attorney, Agent, or Firm*—Teddy C. Scott, Jr.; Polsinelli Shughart PC

(57) ABSTRACT

The present invention relates to a first group of novel oligonucleotides, here identified as Genomic Address Messenger or GAM oligonucleotide, and a second group of novel operon-like polynucleotides, here identified as Genomic Record or GR polynucleotide. GAM oligonucleotides selectively inhibit translation of known 'target' genes, many of which are known to be involved in various diseases. Nucleic acid molecules are provided respectively encoding 15454 GAM precursors oligonucleotides, and 681 GR polynucleotides, as are vectors and probes both comprising the nucleic acid molecules, and methods and systems for detecting GAM oligonucleotides and GR polynucleotides and specific functions and utilities thereof, for detecting expression of GAM oligonucleotides and GR polynucleotides, and for selectively enhancing and selectively inhibiting translation of the respective target genes thereof.

18 Claims, 31 Drawing Sheets

OTHER PUBLICATIONS

Engdahl HM, Hjalt TA, Wagner EG. A two unit antisense RNA cassette test system for silencing of target genes. Nucleic Acids Res. Aug. 15, 1997 3218-27 25.

Dsouza, M., N. Larsen and R. Overbeek. Searching for patterns in genomic data Trends Genet Dec. 1997 497-498 13.

Moss, E. G., R. C. Lee and V. Ambros. The cold shock domain protein LIN-28 controls developmental timing in *C. elegans* and is regulated by the lin-4 RNA Cell 1997 637 88.

Fire, A., S. Xu, M. K. Montgomery, S. A. Kostas, S. E. Driver and C. C. Mello. Potent and specific genetic interference by double-stranded RNA in *Caenorhabditis elegans* Nature Feb. 19, 1998 806-811 391.

Waterhouse, P. M., M. W. Graham and M. B. Wang. Virus resistance and gene silencing in plants can be induced by simultaneous expression of sense and antisense RNA Proc Natl Acad Sci U S A Nov. 10, 1998 13959-13964 95.

Ngo, H., C. Tschudi, K. Gull and E. Ullu. Double-stranded RNA induces mRNA degradation in *Trypanosoma brucei* Proc Natl Acad Sci U S A Dec. 8, 1998 14687-14692 95.

Verma, S. and F. Eckstein. Modified oligonucleotides: synthesis and strategy for users Annu Rev Biochem *No date in Pubmed* 1998 99-134 67.

Wuchty, S., W. Fontana, I. L. Hofacker and P. Schuster. Complete suboptimal folding of RNA and the stability of secondary structures Biopolymers Feb. 1999 145-165 49.

Mathews, D. H., J. Sabina, M. Zuker and D. H. Turner. Expanded sequence dependence of thermodynamic parameters improves prediction of RNA secondary structure J Mol Biol May 21, 1999 911-940 288.

Chang, P. L. Encapsulation for somatic gene therapy Ann N Y Acad Sci Jun. 18, 1999 146-158 875.

Zhang, M. Q. Large-scale gene expression data analysis: a new challenge to computational biologists Genome Res Aug. 1999 681-688 9.

Grisaru, D., M. Sternfeld, A. Eldor, D. Glick and H. Soreq. Structural roles of acetylcholinesterase variants in biology and pathology Eur J Biochem Sep. 1999 672-686 264.

Fire, A. RNA-triggered gene silencing Trends Genet Sep. 1999 358-363 15.

Tabara, H., M. Sarkissian, W. G. Kelly, J. Fleenor, A. Grishok, L. Timmons, A. Fire and C. C. Mello. The rde-1 gene, RNA interference, and transposon silencing in *C. elegans* Cell Oct. 15, 1999 123-132 99.

Ryo, A., Y. Suzuki, K. Ichiyama, T. Wakatsuki, N. Kondoh, A. Hada, M. Yamamoto and N. Yamamoto. Serial analysis of gene expression in HIV-1-infected T cell lines FEBS Lett Nov. 26, 1999 182-186 462.

Olsen, P. H. and V. Ambros. The lin-4 regulatory RNA controls developmental timing in *Caenorhabditis elegans* by blocking LIN-14 protein synthesis after the initiation of translation Dev Biol Dec. 15, 1999 671-680 216.

Tuschl, T., P. D. Zamore, R. Lehmann, D. P. Bartel and P. A. Sharp. Targeted mRNA degradation by double-stranded RNA in vitro Genes Dev Dec. 15, 1999 3191-3197 13.

Reinhart, B. J., F. J. Slack, M. Basson, A. E. Pasquinelli, J. C. Bettinger, A. E. Rougvie, H. R. Horvitz and G. Ruvkun. The 21-nucleotide let-7 RNA regulates developmental timing in *Caenorhabditis elegans* Nature Feb. 24, 2000 901-906 403.

Pitt, J. N., J. A. Schisa and J. R. Priess. P granules in the germ cells of *Caenorhabditis elegans* adults are associated with clusters of nuclear pores and contain RNA Dev Biol Mar. 15, 2000 315-333 219.

Hammond, S. M., E. Bernstein, D. Beach and G. J. Hannon. An RNA-directed nuclease mediates post-transcriptional gene silencing in *Drosophila* cells Nature Mar. 16, 2000 293-296 404.

Slack, F. J., M. Basson, Z. Liu, V. Ambros, H. R. Horvitz and G. Ruvkun. The lin-41 RBCC gene acts in the *C. elegans* heterochronic pathway between the let-7 regulatory RNA and the LIN-29 transcription factor Mol Cell Apr. 2000 659-669 5.

Fortier, E. and J. M. Belote. Temperature-dependent gene silencing by an expressed inverted repeat in *Drosophila* Genesis Apr. 2000 240-244 26.

Mourrain, P., C. Beclin, T. Elmayan, F. Feuerbach, C. Godon, J. B. Morel, D. Jouette, A. M. Lacombe, S. Nikic, N. Picault, K. Remoue, M. Sanial, T. A. Vo and H. Vaucheret. Arabidopsis SGS2 and SGS3 genes are required for posttranscriptional gene silencing and natural virus resistance Cell May 26, 2000 533-542 101.

Sijen, T. and J. M. Kooter. Post-transcriptional gene-silencing: RNAs on the attack or on the defense? Bioessays Jun. 2000 520-531 22.

Brenner, S., M. Johnson, J. Bridgham, G. Golda, D. H. Lloyd, D. Johnson, S. Luo, S. McCurdy, M. Foy, M. Ewan, R. Roth, D. George, S. Eletr, G. Albrecht, E. Vermaas, S. R. Williams, K. Moon, T. Burcham, M. Pallas, R. B. Dubridge, J. Kirchner, K. Fearon, J. Mao and K. Corcoran. Gene expression analysis by massively parallel signature sequencing (MPSS) on microbead arrays Nat Biotechnol Jun. 2000 630-634 18.

Ryo, A., Y. Suzuki, M. Arai, N. Kondoh, T. Wakatsuki, A. Hada, M. Shuda, K. Tanaka, C. Sato, M. Yamamoto and N. Yamamoto. Identification and characterization of differentially expressed mRNAs in HIV type 1-infected human T cells AIDS Res Hum Retroviruses Jul. 1, 2000 995-1005 16.

Nilsson, M., G. Barbany, D. O. Antson, K. Gertow and U. Landegren. Enhanced detection and distinction of RNA by enzymatic probe ligation Nat Biotechnol Jul. 2000 791-793 18.

Kent, W. J. and A. M. Zahler. Conservation, regulation, synteny, and introns in a large-scale *C. briggsae-C. elegans* genomic alignment Genome Res Aug. 2000 1115-1125 10.

Kennerdell, J. R. and R. W. Carthew. Heritable gene silencing in *Drosophila* using double-stranded RNA Nat Biotechnol Aug. 2000 896-898 18.

Smith, N. A., S. P. Singh, M. B. Wang, P. A. Stoutjesdijk, A. G. Green and P. M. Waterhouse. Total silencing by intron-spliced hairpin RNAs Nature Sep. 21, 2000 319-320 407.

Voinnet, O., C. Lederer and D. C. Baulcombe. A viral movement protein prevents spread of the gene silencing signal in *Nicotiana benthamiana* Cell Sep. 29, 2000 157-167 103.

Metter MF, Aufsatz W, van der Winden J, Matzke MA, Matzke AJ. Transcriptional silencing and promoter methylation triggered by double-stranded RNA. EMBO J. Oct. 2000 5194-201 19.

Yang, D., H. Lu and J. W. Erickson. Evidence that processed small dsRNAs may mediate sequence-specific mRNA degradation during RNAi in *Drosophila* embryos Curr Biol Oct. 5, 2000 1191-1200 10.

Anandalakshmi, R., R. Marathe, X. GE, J. M. Herr, Jr., C. Mau, A. Mallory, G. Pruss, L. Bowman and V. B. Vance. A calmodulin-related protein that suppresses posttranscriptional gene silencing in plants Science Oct. 6, 2000 142-144 290.

Fagard, M., S. Boutet, J. B. Morel, C. Bellini and H. Vaucheret. AGO1, QDE-2, and RDE-1 are related proteins required for post-transcriptional gene silencing in plants, quelling in fungi, and RNA interference in animals Proc Natl Acad Sci U S A Oct. 10, 2000 11650-11654 97.

Pasquinelli, A. E., B. J. Reinhart, F. Slack, M. Q. Martindale, M. I. Kuroda, B. Maller, D. C. Hayward, E. E. Ball, B. Degnan, P. Muller, J. Spring, A. Srinivasan, M. Fishman, J. Finnerty, J. Corbo, M. Levine, P. Leahy, E. Davidson and G. Ruvkun. Conservation of the sequence and temporal expression of let-7 heterochronic regulatory RNA Nature Nov. 2, 2000 86-89 408.

Llave, C., K. D. Kasschau and J. C. Carrington. Virus-encoded suppressor of posttranscriptional gene silencing targets a maintenance step in the silencing pathway Proc Natl Acad Sci U S A Nov. 21, 2000 13401-13406 9.

Cogoni, C. and G. Macino. Post-transcriptional gene silencing across kingdoms Curr Opin Genet Dev Dec. 2000 638-643 10.

Elbashir, S. M., W. Lendeckel and T. Tuschl. RNA interference is mediated by 21- and 22-nucleotide RNAs Genes Dev Jan. 15, 2001 188-200 15.

Bernstein, E., A. A. Caudy, S. M. Hammond and G. J. Hannon. Role for a bidentate ribonuclease in the initiation step of RNA interference Nature Jan. 18, 2001 363-366 409.

Vaucheret, H. and M. Fagard. Transcriptional gene silencing in plants: targets, inducers and regulators Trends Genet Jan. 2001 29-35 17.

Thomas, C. L., L. Jones, D. C. Baulcombe and A. J. Maule. Size constraints for targeting post-transcriptional gene silencing and for RNA-directed methylation in *Nicotiana benthamiana* using a potato virus X vector Plant J Feb. 2001 417-425 25.

Galyam, N., D. Grisaru, M. Grifman, N. Melamed-Book, F. Eckstein, S. Seidman, A. Eldor and H. Soreq. Complex host cell responses to antisense suppression of ACHE gene expression Antisense Nucleic Acid Drug Dev Feb. 2001 51-57 11.

Sharp, P. A. RNA interference—2001 Genes Dev Mar. 1, 2001 485-490 15.

Mallory, A. C., L. Ely, T. H. Smith, R. Marathe, R. Anandalakshmi, M. Fagard, H. Vaucheret, G. Pruss, L. Bowman and V. B. Vance. HC-Pro suppression of transgene silencing eliminates the small RNAs but not transgene methylation or the mobile signal Plant Cell Mar. 2001 571-583 13.

Matzke, M. A., A. J. Matzke, G. J. Pruss and V. B. Vance. RNA-based silencing strategies in plants Curr Opin Genet Dev Apr. 2001 221-227 11.

Schisa, J. A., J. N. Pitt and J. R. Priess. Analysis of RNA associated with P granules in germ cells of *C. elegans* adults Development Apr. 2001 1287-1298 128.

Di Serio, F., H. Schob, A. Iglesias, C. Tarina, E. Bouldoires and F. Meins, Jr. Sense- and antisense-mediated gene silencing in tobacco is inhibited by the same viral suppressors and is associated with accumulation of small RNAs Proc Natl Acad Sci U S A May 22, 2001 6506-6510 98.

Elbashir, S. M., J. Harborth, W. Lendeckel, A. Yalcin, K. Weber and T. Tuschl. Duplexes of 21-nucleotide RNAs mediate RNA interference in cultured mammalian cells Nature May 24, 2001 494-498 411.

Piccin, A., A. Salameh, C. Benna, F. Sandrelli, G. Mazzotta, M. Zordan, E. Rosato, C. P. Kyriacou and R. Costa. Efficient and heritable functional knock-out of an adult phenotype in *Drosophila* using a GAL4-driven hairpin RNA incorporating a heterologous spacer Nucleic Acids Res Jun. 15, 2001 E55-55 29.

Vance, V. and H. Vaucheret. RNA silencing in plants—defense and counterdefense Science Jun. 22, 2001 2277-2280 292.

Argaman, L., R. Hershberg, J. Vogel, G. Bejerano, E. G. Wagner, H. Margalit and S. Altuvia. Novel small RNA-encoding genes in the intergenic regions of *Escherichia coli* Curr Biol Jun. 26, 2001 941-950 11.

Grishok, A., A. E. Pasquinelli, D. Conte, N. Li, S. Parrish, I. Ha, D. L. Baillie, A. Fire, G. Ruvkun and C. C. Mello. Genes and mechanisms related to RNA interference regulate expression of the small temporal RNAs that control *C. elegans* developmental timing Cell Jul. 13, 2001 23-34 106.

Hutvagner, G., J. McLachlan, A. E. Pasquinelli, E. Balint, T. Tuschl and P. D. Zamore. A cellular function for the RNA-interference enzyme Dicer in the maturation of the let-7 small temporal RNA Science Aug. 3, 2001 834-838 293.

Hammond, S. M., S. Boettcher, A. A. Caudy, R. Kobayashi and G. J. Hannon. Argonaute2, a link between genetic and biochemical analyses of RNAi Science Aug. 10, 2001 1146-1150 293.

Vaucheret, H., C. Beclin and M. Fagard. Post-transcriptional gene silencing in plants J Cell Sci Sep. 2001 3083-3091 114.

Wesley, S. V., C. A. Helliwell, N. A. Smith, M. B. Wang, D. T. Rouse, Q. Liu, P. S. Gooding, S. P. Singh, D. Abbott, P. A. Stoutjesdijk, S. P. Robinson, A. P. Gleave, A. G. Green and P. M. Waterhouse. Construct design for efficient, effective and high-throughput gene silencing in plants Plant J Sep. 2001 581-590 27.

Mattick, J. S. and M. J. Gagen. The evolution of controlled multitasked gene networks: the role of introns and other noncoding RNAs in the development of complex organisms Mol Biol Evol Sep. 2001 1611-1630 18.

Carter, R. J., I. Dubchak and S. R. Holbrook. A computational approach to identify genes for functional RNAs in genomic sequences Nucleic Acids Res Oct. 1, 2001 3928-3938 29.

Moss, E. G. RNA interference: its a small RNA world Curr Biol Oct. 2, 2001 R772-775 11.

Ketting, R. F., S. E. Fischer, E. Bernstein, T. Sijen, G. J. Hannon and R. H. Plasterk. Dicer functions in RNA interference and in synthesis of small RNA involved in developmental timing in *C. elegans* Genes Dev Oct. 15, 2001 2654-2659 15.

Ruvkun, G. Molecular biology. Glimpses of a tiny RNA world Science Oct. 26, 2001 797-799 294.

Lee, R. C. and V. Ambros. An extensive class of small RNAs in *Caenorhabditis elegans* Science Oct. 26, 2001 862-864 294.

Lau, N. C., L. P. Lim, E. G. Weinstein and D. P. Bartel. An abundant class of tiny RNAs with probable regulatory roles in *Caenorhabditis elegans* Science Oct. 26, 2001 858-862 294.

Lagos-Quintana, M., R. Rauhut, W. Lendeckel and T. Tuschl. Identification of novel genes coding for small expressed RNAs Science Oct. 26, 2001 853-858 294.

Itaya, A., A. Folimonov, Y. Matsuda, R. S. Nelson and B. Ding. Potato spindle tuber viroid as inducer of RNA silencing in infected tomato Mol Plant Microbe Interact Nov. 2001 1332-1334 14.

Mattick, J. S. Non-coding RNAs: the architects of eukaryotic complexity EMBO Rep Nov. 2001 986-991 2.

Elbashir, S. M., J. Martinez, A. Patkaniowska, W. Lendeckel and T. Tuschl. Functional anatomy of siRNAs for mediating efficient RNAi in *Drosophila melanogaster* embryo lysate Embo J Dec. 3, 2001 6877-6888 20.

Ambros, V. microRNAs: tiny regulators with great potential Cell Dec. 28, 2001 823-826 107.

Blaszczyk, J., J. E. Tropea, M. Bubunenko, K. M. Routzahn, D. S. Waugh, D. L. Court and X. Ji. Crystallographic and modeling studies of RNase III suggest a mechanism for double-stranded RNA cleavage Structure Dec. 2001 1225-1236 9.

Crete, P., S. Leuenberger, V. A. Iglesias, V. Suarez, H. Schob, H. Holtorf, S. Van Eeden and F. Meins. Graft transmission of induced and spontaneous post-transcriptional silencing of chitinase genes Plant J Dec. 2001 493-501 28.

Smallridge, R. A small fortune Nat Rev Mol Cell Biol Dec. 2001 867 2.

Eddy, S. R. Non-coding RNA genes and the modern RNA world Nat Rev Genet Dec. 2001 919-929 2.

Lu, C. M. miRNA bead detection Genaco Biomedical Products PHS 398 2001 1.

Matzke, M., A. J. Matzke and J. M. Kooter. RNA: guiding gene silencing 2001 1080 293.

Grosshans, H. and F. J. Slack. Micro-RNAs: small is plentiful J Cell Biol Jan. 7, 2002 17-21 156.

Meshorer, E., C. Erb, R. Gazit, L. Pavlovsky, D. Kaufer, A. Friedman, D. Glick, N. Benarie and H. Soreq. Alternative splicing and neuritic mRNA translocation under long-term neuronal hypersensitivity Science Jan. 18, 2002 508-512 295.

Paddison, P. J., A. A. Caudy and G. J. Hannon. Stable suppression of gene expression by RNAi in mammalian cells Proc Natl Acad Sci U S A Feb. 5, 2002 1443-1448 99.

Moss, E. G. MicroRNAs: hidden in the genome Curr Biol Feb. 19, 2002 R138-140 12.

Banerjee, D. and F. Slack. Control of developmental timing by small temporal RNAs: a paradigm for RNA-mediated regulation of gene expression Bioessays Feb. 2002 119-129 24.

Elbashir, S. M., J. Harborth, K. Weber and T. Tuschl. Analysis of gene function in somatic mammalian cells using small interfering RNAs Methods Feb. 2002 199-213 26.

Han, Y. and D. Grierson. Relationship between small antisense RNAs and aberrant RNAs associated with sense transgene mediated gene silencing in tomato Plant J Feb. 2002 509-519 29.

Nicholson, R. H. and A. W. Nicholson. Molecular characterization of a mouse cDNA encoding Dicer, a ribonuclease III ortholog involved in RNA interference Mamm Genome Feb. 2002 67-73 13.

Puerta-Fernandez, E., A. Barroso-Deljesus and A. Berzal-Herranz. Anchoring hairpin ribozymes to long target RNAs by loop-loop RNA interactions Antisense Nucleic Acid Drug Dev Feb. 2002 1-9 12.

Giordano, E., R. Rendina, I. Peluso and M. Furia. RNAi triggered by symmetrically transcribed transgenes in *Drosophila melanogaster* Genetics Feb. 2002 637-648 160.

Martens, H., J. Novotny, J. Oberstrass, T. L. Steck, P. Postlethwait and W. Nellen. RNAi in Dictyostelium: the role of RNA-directed RNA polymerases and double-stranded RNase Mol Biol Cell Feb. 2002 445-453 13.

Mourelatos, Z., J. Dostie, S. Paushkin, A. Sharma, B. Charroux, L. Abel, J. Rappsilber, M. Mann and G. Dreyfuss. miRNPs: a novel class of ribonucleoproteins containing numerous microRNAs Genes Dev Mar. 15, 2002 720-728 16.

Seggerson, K., L. Tang and E. G. Moss. Two genetic circuits repress the *Caenorhabditis elegans* heterochronic gene lin-28 after translation initiation Dev Biol Mar. 15, 2002 215-225 243.

Morel, J. B., C. Godon, P. Mourrain, C. Beclin, S. Boutet, F. Feuerbach, F. Proux and H. Vaucheret. Fertile hypomorphic Argonaute (ago1) mutants impaired in post-transcriptional gene silencing and virus resistance Plant Cell Mar. 2002 629-639 14.

Catalanotto, C., G. Azzalin, G. Macino and C. Cogoni. Involvement of small RNAs and role of the qde genes in the gene silencing pathway in Neurospora Genes Dev Apr. 1, 2002 790-795 16.

Boutla, A., K. Kalantidis, N. Tavernarakis, M. Tsagris and M. Tabler. Induction of RNA interference in *Caenorhabditis elegans* by RNAs derived from plants exhibiting post-transcriptional gene silencing Nucleic Acids Res Apr. 1, 2002 1688-1694 30.

Pasquinelli, A. E. and G. Ruvkun. Control of developmental timing by micrornas and their targets Annu Rev Cell Dev Biol Epub 2002 Apr. 2, 2002 495-513 18.

Paddison, P. J., A. A. Caudy, E. Bernstein, G. J. Hannon and D. S. Conklin. Short hairpin RNAs (shRNAs) induce sequence-specific silencing in mammalian cells Genes Dev Apr. 15, 2002 948-958 16.

Beclin, C., S. Boutet, P. Waterhouse and H. Vaucheret. A branched pathway for transgene-induced RNA silencing in plants Curr Biol Apr. 16, 2002 684-688 12.

Eddy, S. R. Computational genomics of noncoding RNA genes Cell Apr. 19, 2002 137-140 109.

Lagos-Quintana, M., R. Rauhut, A. Yalcin, J. Meyer, W. Lendeckel and T. Tuschl. Identification of tissue-specific microRNAs from mouse Curr Biol Apr. 30, 2002 735-739 12.

Kent, W. J. Blat—the Blast-like alignment tool Genome Res Apr. 2002 656-664 12.

Hutvagner, G. and P. D. Zamore. RNAi: nature abhors a double-strand Curr Opin Genet Dev Apr. 2002 225-232 12.

Nilsson, M., J. Baner, M. Mendel-Hartvig, F. Dahl, D. O. Antson, M. Gullberg and U. Landegren. Making ends meet in genetic analysis using padlock probes Hum Mutat Apr. 2002 410-415 19.

Pasquinelli, A. E. MicroRNAs: deviants no longer Trends Genet Apr. 2002 171-173 18.

Lai, E. C. Micro RNAs are complementary to 3' UTR sequence motifs that mediate negative post-transcriptional regulation Nat Genet Apr. 2002 363-364 30.

Schwarz, D. S. and P. D. Zamore. Why do miRNAs live in the miRNP? Genes Dev May 1, 2002 1025-1031 16.

Brantl, S. Antisense-RNA regulation and RNA interference Biochim Biophys Acta May 3, 2002 15-25 1575.

Li, H., W. X. Li and S. W. Ding. Induction and suppression of RNA silencing by an animal virus Science May 17, 2002 1319-1321 296.

Zamore, P. D. Ancient pathways programmed by small RNAs Science May 17, 2002 1265-1269 296.

Chen, S., E. A. Lesnik, T. A. Hall, R. Sampath, R. H. Griffey, D. J. Ecker and L. B. Blyn. A bioinformatics based approach to discover small RNA genes in the *Escherichia coli* genome Biosystems Mar.-May 2002 157-177 65.

Lee, N. S., T. Dohjima, G. Bauer, H. Li, M. J. Li, A. Ehsani, P. Salvaterra and J. Rossi. Expression of small interfering RNAs targeted against HIV-1 rev transcripts in human cells Nat Biotechnol May 2002 500-505 20.

Draghici, S. Statistical intelligence: effective analysis of high-density microarray data Drug Discov Today Jun. 1, 2002 S55-63 7.

Silhavy, D., A. Molnar, A. Lucioli, G. Szittya, C. Hornyik, M. Tavazza and J. Burgyan. A viral protein suppresses RNA silencing and binds silencing-generated, 21- to 25-nucleotide double-stranded RNAs Embo J Jun. 17, 2002 3070-3080 21.

Ayash-Rashkovsky, M., Z. Weisman, J. Diveley, R. B. Moss, Z. Bentwich and G. Borkow. Generation of Th1 immune responses to inactivated, gp120-depleted HIV-1 in mice with a dominant Th2 biased immune profile via immunostimulatory [correction of imunostimulatory] oligonucleotides—relevance to AIDS vaccines in developing countries Vaccine Jun. 21, 2002 2684-2692 20.

Tabara, H., E. Yigit, H. Siomi and C. C. Mello. The dsRNA binding protein RDE-4 interacts with RDE-1, DCR-1, and a DExH-box helicase to direct RNAi in *C. elegans* Cell Jun. 28, 2002 861-871 109.

Bettencourt, R., O. Terenius and I. Faye. Hemolin gene silencing by ds-RNA injected into *Cecropia pupae* is lethal to next generation embryos Insect Mol Biol Jun. 2002 267-271 11.

Hooper, N. M. and A. J. Turner. The search for alpha-secretase and its potential as a therapeutic approach to Alzheimer s disease Curr Med Chem Jun. 2002 1107-1119 9.

Liu, Q., S. Singh and A. Green. High-oleic and high-stearic cottonseed oils: nutritionally improved cooking oils developed using gene silencing J Am Coll Nutr Jun. 2002 205S-211S 21.

Zeng, Y., E. J. Wagner and B. R. Cullen. Both natural and designed micro RNAs can inhibit the expression of cognate mRNAs when expressed in human cells Mol Cell Jun. 2002 1327-1333 9.

McManus, M. T., C. P. Petersen, B. B. Haines, J. Chen and P. A. Sharp. Gene silencing using micro-RNA designed hairpins Rna Jun. 2002 842-850 8.

Reinhart, B. J., E. G. Weinstein, M. W. Rhoades, B. Bartel and D. P. Bartel. MicroRNAs in plants Genes Dev Jul. 1, 2002 1616-1626 16.

McCaffrey, A. P., L. Meuse, T. T. Pham, D. S. Conklin, G. J. Hannon and M. A. Kay. RNA interference in adult mice Nature Jul. 4, 2002 38-39 418.

Hannon, G. J. RNA interference Nature Jul. 11, 2002 244-251 418.

Dennis, C. The brave new world of RNA Nature Jul. 11, 2002 122-124 418.

Jacque, J. M., K. Triques and M. Stevenson. Modulation of HIV-1 replication by RNA interference Nature Jul. 25, 2002 435-438 418.

Cullen, B. R. RNA interference: antiviral defense and genetic tool Nat Immunol Jul. 2002 597-599 3.

Ma, C. and A. Mitra. Intrinsic direct repeats generate consistent post-transcriptional gene silencing in tobacco Plant J Jul. 2002 37-49 31.

Novina, C. D., M. F. Murray, D. M. Dykxhoorn, P. J. Beresford, J. Riess, S. K. Lee, R. G. Collman, J. Lieberman, P. Shankar and P. A. Sharp. siRNA-directed inhibition of HIV-1 infection Nat Med Jul. 2002 681-686 8.

Pomerantz, R. J. RNA interference meets HIV-1: will silence be golden? Nat Med Jul. 2002 659-660 8.

Zeng, Y. and B. R. Cullen. RNA interference in human cells is restricted to the cytoplasm Rna Jul. 2002 855-860 8.

Xiang, C. C., O. A. Kozhich, M. Chen, J. M. Inman, Q. N. Phan, Y. Chen and M. J. Brownstein. Amine-modified random primers to label probes for DNA microarrays Nat Biotechnol Jul. 2002 738-742 20.

Llave, C., K. D. Kasschau, M. A. Rector and J. C. Carrington. Endogenous and silencing-associated small RNAs in plants Plant Cell Jul. 2002 1605-1619 14.

Rhoades, M. W., B. J. Reinhart, L. P. Lim, C. B. Burge, B. Bartel and D. P. Bartel. Prediction of plant microRNA targets Cell Aug. 23, 2002 513-520 110.

Hipfner, D. R., K. Weigmann and S. M. Cohen. The bantam gene regulates *Drosophila* growth Genetics Aug. 2002 1527-1537 161.

Liu, Q., S. P. Singh and A. G. Green. High-stearic and High-oleic cottonseed oils produced by hairpin RNA-mediated post-transcriptional gene silencing Plant Physiol Aug. 2002 1732-1743 129.

Stoutjesdijk, P. A., S. P. Singh, Q. Liu, C. J. Hurlstone, P. A. Waterhouse and A. G. Green. hpRNA-mediated targeting of the *Arabidopsis* FAD2 gene gives highly efficient and stable silencing Plant Physiol Aug. 2002 1723-1731 129.

Suzuma, S., S. Asari, K. Bunai, K. Yoshino, Y. Ando, H. Kakeshita, M. Fujita, K. Nakamura and K. Yamane. Identification and characterization of novel small RNAs in the aspS-yrvM intergenic region of the *Bacillus subtilis* genome Microbiology Aug. 2002 2591-2598 148.

Milligan, L., T. Forne, E. Antoine, M. Weber, B. Hemonnot, L. Dandolo, C. Brunel and G. Cathala. Turnover of primary transcripts is a major step in the regulation of mouse H19 gene expression EMBO Rep Aug. 2002 774-779 3.

Hamilton, A., O. Voinnet, L. Chappell and D. Baulcombe. Two classes of short interfering RNA in RNA silencing Embo J Sep. 2, 2002 4671-4679 21.

Lee, Y., K. Jeon, J. T. Lee, S. Kim and V. N. Kim. MicroRNA maturation: stepwise processing and subcellular localization Embo J Sep. 2, 2002 4663-4670 21.

Klahre, U., P. Crete, S. A. Leuenberger, V. A. Iglesias and F. Meins, Jr. High molecular weight RNAs and small interfering RNAs induce systemic posttranscriptional gene silencing in plants Proc Natl Acad Sci U S A Sep. 3, 2002 11981-11986 99.

Park, W., J. Li, R. Song, J. Messing and X. Chen. Carpel Factory, a Dicer homolog, and HEN1, a novel protein, act in microRNA metabolism in *Arabidopsis thaliana* Curr Biol Sep. 3, 2002 1484-1495 12.

Jiang, M. and J. Milner. Selective silencing of viral gene expression in HPV-positive human cervical carcinoma cells treated with siRNA, a primer of RNA interference Oncogene Sep. 5, 2002 6041-6048 21.

Martinez, J., A. Patkaniowska, H. Urlaub, R. Luhrmann and T. Tuschl. Single-stranded antisense siRNAs guide target RNA cleavage in RNAi Cell Sep. 6, 2002 563-574 110.

Allshire, R. Molecular biology. RNAi and heterochromatin—a hushed-up affair Science Sep. 13, 2002 1818-1819 297.

Reinhart, B. J. and D. P. Bartel. Small RNAs correspond to centromere heterochromatic repeats Science Sep. 13, 2002 1831 297.

Volpe, T. A., C. Kidner, I. M. Hall, G. Teng, S. I. Grewal and R. A. Martienssen. Regulation heterochromatic silencing and histone H3 lysine-9 methylation by RNAi Science Sep. 13, 2002 1833-1837 297.

Baulcombe, D. DNA events. An RNA microcosm Science Sep. 20, 2002-2003 297.

Llave, C., Z. Xie, K. D. Kasschau and J. C. Carrington. Cleavage of Scarecrow-like mRNA targets directed by a class of *Arabidopsis* miRNA Science Sep. 20, 2002 2053-2056 297.

Mochizuki, K., N. A. Fine, T. Fujisawa and M. A. Gorovsky. Analysis of a piwi-related gene implicates small RNAs in genome rearrangement in tetrahymena Cell Sep. 20, 2002 689-699 110.

Hutvagner, G. and P. D. Zamore. A microRNA in a multiple-turnover RNAi enzyme complex Science Sep. 20, 2002 2056-2060 297.

Coburn, G. A. and B. R. Cullen. Potent and specific inhibition of human immunodeficiency virus type 1 replication by RNA interference J Virol Sep. 2002 9225-9231 76.

Caudy, A. A., M. Myers, G. J. Hannon and S. M. Hammond. Fragile X-related protein and VIG associate with the RNA interference machinery Genes Dev Oct. 1, 2002 2491-2496 16.

Ishizuka, A., M. C. Siomi and H. Siomi. A *Drosophila* fragile X protein interacts with components of RNAi and ribosomal proteins Genes Dev Oct. 1, 2002 2497-2508 16.

Voinnet, O. RNA silencing: small RNAs as ubiquitous regulators of gene expression Curr Opin Plant Biol Oct . 2002 444-451 5.

Golden, T. A., S. E. Schauer, J. D. Lang, S. Pien, A. R. Mushegian, U. Grossniklaus, D. W. Meinke and A. Ray. Short Integuments1/Suspensor1/Carpel Factory, a Dicer homolog, is a maternal effect gene required for embryo development in *Arabidopsis* Plant Physiol Oct. 2002 808-822 130.

Merkle, I., M. J. Van Ooij, F. J. Van Kuppeveld, D. H. Glaudemans, J. M. Galama, A. Henke, R. Zell and W. J. Melchers. Biological significance of a human enterovirus B-specific RNA element in the 3' nontranslated region J Virol Oct. 2002 9900-9909 76.

Froeyen, M. and P. Herdewijn. RNA as a target for drug design, the example of Tat-TAR interaction Curr Top Med Chem Oct. 2002 1123-1145 2.

Carmell, M. A., Z. Xuan, M. Q. Zhang and G. J. Hannon. The Argonaute family: tentacles that reach into RNAi, developmental control, stem cell maintenance, and tumorigenesis Genes Dev Nov. 1, 2002 2733-2742 16.

Provost, P., D. Dishart, J. Doucet, D. Frendewey, B. Samuelsson and O. Radmark. Ribonuclease activity and RNA binding of recombinant human Dicer Embo J Nov. 1, 2002 5864-5874 21.

Zhang, H., F. A. Kolb, V. Brondani, E. Billy and W. Filipowicz. Human Dicer preferentially cleaves dsRNAs at their termini without a requirement for ATP Embo J Nov. 1, 2002 5875-5885 21.

Mallory, A. C., B. J. Reinhart, D. Bartel, V. B. Vance and L. H. Bowman. A viral suppressor of RNA silencing differentially regulates the accumulation of short interfering RNAs and micro-RNAs in tobacco Proc Natl Acad Sci U S A Nov. 12, 2002 15228-15233 99.

Gottesman, S. Stealth regulation: biological circuits with small RNA switches Genes Dev Nov. 15, 2002 2829-2842 16.

Calin, G. A., C. D. Dumitru, M. Shimizu, R. Bichi, S. Zupo, E. Noch, H. Aldler, S. Rattan, M. Keating, K. Rai, L. Rassenti, T. Kipps, M. Negrini, F. Bullrich and C. M. Croce. Frequent deletions and downregulation of micro- RNA genes miR15 and miR16 at 13q14 in chronic lymphocytic leukemia Proc Natl Acad Sci U S A Nov. 26, 2002 15524-15529 99.

Gaudilliere, B., Y. Shi and A. Bonni. RNA interference reveals a requirement for myocyte enhancer factor 2A in activity-dependent neuronal survival J Biol Chem Nov. 29, 2002 46442-46446 277.

Jones, L. Revealing micro-RNAs in plants Trends Plant Sci Nov. 2002 473-475 7.

Schauer, S. E., S. E. Jacobsen, D. W. Meinke and A. Ray. DICER-LIKE1: blind men and elephants in *Arabidopsis* development Trends Plant Sci Nov. 2002 487-491 7.

Okazaki, Y., M. Furuno, T. Kasukawa, J. Adachi, H. Bono, S. Kondo, et al. Analysis of the mouse transcriptome based on functional annotation of 60,770 full-length cDNAs Nature Dec. 5, 2002 563-573 420.

Dennis, C. Small RNAs: the genome's guiding hand? Nature Dec. 19-26, 2002 732 420.

Uchida, N., S. Hoshino, H. Imataka, N. Sonenberg and T. Katada. A novel role of the mammalian GSPT/eRF3 associating with poly(A)-binding protein in Cap/Poly(A)-dependent translation J Biol Chem Dec. 27, 2002 50286-50292 277.

Huttenhofer, A., J. Brosius and J. P. Bachellerie. RNomics: identification and function of small, non-messenger RNAs Curr Opin Chem Biol Dec. 2002 835-843 6.

Wood, N. T. Unravelling the molecular basis of viral suppression of PTGS Trends Plant Sci 2002 384 7.

Cohen, O., C. Erb, D. Ginzberg, Y. Pollak, S. Seidman, S. Shoham, R. Yirmiya and H. Soreq. Neuronal overexpression of "readthrough" acetylcholinesterase is associated with antisense-suppressible behavioral impairments Mol Psychiatry *No date in pubmed* 2002 .874-885 7.

Mlotshwa, S., O. Voinnet, M. F. Mette, M. Matzke, H. Vaucheret, S. W. Ding, G. Pruss and V. B. Vance. RNA silencing and the mobile silencing signal Plant Cell *No date in pubmed* 2002 S289-301 14 Suppl.

Tang, G., B. J. Reinhart, D. P. Bartel and P. D. Zamore. A biochemical framework for RNA silencing in plants Genes Dev Jan. 1, 2003 49-63 17.

Kawasaki, H. and K. Taira. Short hairpin type of dsRNAs that are controlled by tRNA(Val) promoter significantly induce RNAi-mediated gene silencing in the cytoplasm of human cells Nucleic Acids Res Jan. 15, 2003 700-707 31.

Ashrafi, K., F. Y. Chang, J. L. Watts, A. G. Fraser, R. S. Kamath, J. Ahringer and G. Ruvkun. Genome-wide RNAi analysis of *Caenorhabditis elegans* fat regulatory genes Nature Jan. 16, 2003 268-272 421.

Kamath, R. S., A. G. Fraser, Y. Dong, G. Poulin, R. Durbin, M. Gotta, A. Kanapin, N. Le Bot, S. Moreno, M. Sohrmann, D. P. Welchman, P. Zipperlen and J. Ahringer. Systematic functional analysis of the *Caenorhabditis elegans* genome using RNAi Nature Jan. 16, 2003 231-237 421.

Tuschl, T. Functional genomics: RNA sets the standard Nature Jan. 16, 2003 220-221 421.

Iyer, L. M., E. V. Koonin and L. Aravind. Evolutionary connection between the catalytic subunits of DNA-dependent RNA polymerases and eukaryotic RNA-dependent RNA polymerases and the origin of RNA polymerases BMC Struct Biol Jan. 28, 2003 1 3.

Shi, Y. Mammalian RNAi for the masses Trends Genet Jan. 2003 9-12 19.

Cerutti, H. RNA interference: traveling in the cell and gaining functions? Trends Genet Jan. 2003 39-46 19.

Zeng, Y. and B. R. Cullen. Sequence requirements for micro RNA processing and function in human cells Rna Jan. 2003 112-123 9.

Kawasaki, H., E. Suyama, M. Iyo and K. Taira. siRNAs generated by recombinant human Dicer induce specific and significant but target site-independent gene silencing in human cells Nucleic Acids Res Feb. 1, 2003 981-987 31.

Reiner, A., D. Yekutieli and Y. Benjamini. Identifying differentially expressed genes using false discovery rate controlling procedures Bioinformatics Feb. 12, 2003 368-375 19.

Doench, J. G., C. P. Petersen and P. A. Sharp. siRNAs can function as miRNAs Genes Dev Feb. 15, 2003 438-442 17.

Gupta, V., A. Cherkassky, P. Chatis, R. Joseph, A. L. Johnson, J. Broadbent, T. Erickson and J. Dimeo. Directly labeled mRNA produces highly precise and unbiased differential gene expression data Nucleic Acids Res Feb. 15, 2003 e13 31.

Boffelli, D., J. McAuliffe, D. Ovcharenko, K. D. Lewis, I. Ovcharenko, L. Pachter and E. M. Rubin. Phylogenetic shadowing of primate sequences to find functional regions of the human genome Science Feb. 28, 2003 1391-1394 299.

Kasschau, K. D., Z. Xie, E. Allen, C. Llave, E. J. Chapman, K. A. Krizan and J. C. Carrington. P1/HC-Pro, a viral suppressor of RNA silencing, interferes with *Arabidopsis* development and miRNA unction Dev Cell Feb. 2003 205-217 4.

Carmell, M. A., L. Zhang, D. S. Conklin, G. J. Hannon and T. A. Rosenquist. Germline transmission of RNAi in mice Nat Struct Biol Feb. 2003 91-92 10.

Dostie, J., Z. Mourelatos, M. Yang, A. Sharma and G. Dreyfuss. Numerous microRNPs in neuronal cells containing novel microRNAs Rna Feb. 2003 180-186 9.

Lagos-Quintana, M., R. Rauhut, J. Meyer, A. Borkhardt and T. Tuschl. New microRNAs from mouse and human Rna Feb. 2003 175-179 9.

Wilson, J. A., S. Jayasena, A. Khvorova, S. Sabatinos, I. G. Rodrigue-Gervais, S. Arya, F. Sarangi, M. Harris-Brandts, S. Beaulieu and C. D. Richardson. RNA interference blocks gene expression and RNA synthesis from hepatitis C replicons propagated in human liver cells Proc Natl Acad Sci U S A Mar. 4, 2003 2783-2788 100.

Lim, L. P., M. E. Glasner, S. Yekta, C. B. Burge and D. P. Bartel. Vertebrate microRNA genes Science Mar. 7, 2003 1540 299.

Maniataki, E., A. E. Martinez De Alba, R. Sagesser, M. Tabler and M. Tsagris. Viroid RNA systemic spread may depend on the interaction of a 71-nucleotide bulged hairpin with the host protein VirP1 Rna Mar. 2003 346-354 9.

Ambros, V., B. Bartel, D. P. Bartel, C. B. Burge, J. C. Carrington, X. Chen, G. Dreyfuss, S. R. Eddy, S. Griffiths-Jones, M. Marshall, M. Matzke, G. Ruvkun and T. Tuschl. A uniform system for microRNA annotation Rna Mar. 2003 277-279 9.

Findley, S. D., M. Tamanaha, N. J. Clegg and H. Ruohola-Baker. Maelstrom, a *Drosophila* spindle-class gene, encodes a protein that colocalizes with Vasa and RDE1/AGO1 homolog, Aubergine, in nuage Development Mar. 2003 859-871 130.

Hershberg, R., S. Altuvia and H. Margalit. A survey of small RNA-encoding genes in *Escherichia coli* Nucleic Acids Res Apr. 1, 2003 1813-1820 31.

Zhou, A., S. Scoggin, R. B. Gaynor and N. S. Williams. Identification of NF-kappa B-regulated genes induced by TNFalpha utilizing expression profiling and RNA interference Oncogene Apr. 3, 2003 2054-2064 22.

Brennecke, J., D. R. Hipfner, A. Stark, R. B. Russell and S. M. Cohen. bantam encodes a developmentally regulated microRNA that controls cell proliferation and regulates the proapoptotic gene hid in *Drosophila* Cell Apr. 4, 2003 25-36 113.

Lim, L. P., N. C. Lau, E. G. Weinstein, A. Abdelhakim, S. Yekta, M. W. Rhoades, C. B. Burge and D. P. Bartel. The microRNAs of *Caenorhabditis elegans* Genes Dev Apr. 15, 2003 991-1008 17.

Xu, P., S. Y. Vernooy, M. Guo and B. A. Hay. The *Drosophila* microRNA Mir-14 suppresses cell death and is required for normal fat metabolism Curr Biol Apr. 29, 2003 790-795 13.

Xie, Z., K. D. Kasschau and J. C. Carrington. Negative feedback regulation of Dicer-Like1 in *Arabidopsis* by microRNA-guided mRNA degradation Curr Biol Apr. 29, 2003 784-789 13.

Carmichael, G. G. Antisense starts making more sense Nat Biotechnol Apr. 2003 371-372 21.

Yelin, R., D. Dahary, R. Sorek, E. Y. Levanon, O. Goldstein, A. Shoshan, A. Diber, S. Biton, Y. Tamir, R. Khosravi, S. Nemzer, E. Pinner, S. Walach, J. Bernstein, K. Savitsky and G. Rotman. Widespread occurrence of antisense transcription in the human genome Nat Biotechnol Apr. 2003 379-386 21.

Boutet, S., F. Vazquez, J. Liu, C. Beclin, M. Fagard, A. Gratias, J. B. Morel, P. Crete, X. Chen and H. Vaucheret. *Arabidopsis* HEN1: a genetic link between endogenous miRNA controlling development and siRNA controlling transgene silencing and virus resistance Curr Biol May 13, 2003 843-848 13.

Ambros, V., R. C. Lee, A. Lavanway, P. T. Williams and D. Jewell. MicroRNAs and other tiny endogenous RNAs in *C. elegans* Curr Biol May 13, 2003 807-818 13.

Liang, X. S., J. Q. Lian, Y. X. Zhou, Q. H. Nie and C. Q. Hao. A small yeast RNA inhibits HCV IRES mediated translation and inhibits replication of poliovirus in vivo World J Gastroenterol May 2003 1008-1013 9.

Grad, Y., J. Aach, G. D. Hayes, B. J. Reinhart, G. M. Church, G. Ruvkun and J. Kim. Computational and experimental identification of *C. elegans* microRNAs Mol Cell May 2003 1253-1263 11.

Abrahante, J. E., A. L. Daul, M. Li, M. L. Volk, J. M. Tennessen, E. A. Miller and A. E. Rougvie. The *Caenorhabditis elegans* hunchback-like gene lin-57/hbl-1 controls developmental time and is regulated by microRNAs Dev Cell May 2003 625-637 4.

Lin, S. Y., S. M. Johnson, M. Abraham, M. C. Vella, A. Pasquinelli, C. Gamberi, E. Gottlieb and F. J. Slack. The *C elegans* hunchback homolog, hbl-1, controls temporal patterning and is a probable microRNA target Dev Cell May 2003 639-650 4.

Zamvil, S. S. and L. Steinman. Diverse targets for intervention during inflammatory and neurodegenerative phases of multiple sclerosis Neuron Jun. 5, 2003 685-688 38.

Ambros, V. MicroRNA pathways in flies and worms: growth, death, fat, stress, and timing Cell Jun. 13, 2003 673-676 113.

Moss, E. G. and L. Tang. Conservation of the heterochronic regulator Lin-28, its developmental expression and microRNA complementary sites Dev Biol Jun. 15, 2003 432-442 258.

Smalheiser, N. R. EST analyses predict the existence of a population of chimeric microRNA precursor-mRNA transcripts expressed in normal human and mouse tissues Genome Biol Epub 2003 Jun. 18, 2003 403 4.

Kawasaki, H. and K. Taira. Hes1 is a target of microRNA-23 during retinoic-acid-induced neuronal differentiation of NT2 cells Nature Jun. 19, 2003 838-842 423.

Lai, E. C., P. Tomancak, R. W. Williams and G. M. Rubin. Computational identification of *Drosophila* microRNA genes Genome Biol Epub 2003 Jun. 30, 2003 R42 4.

No author listed. Whither RNAi? Nat Cell Biol Jun. 2003 489-490 5.

Bartel, B. and D. P. Bartel. MicroRNAs: at the root of plant development? Plant Physiol Jun. 2003 709-717 132.

Dykxhoorn, D. M., C. D. Novina and P. A. Sharp. Killing the messenger: short RNAs that silence gene expression Nat Rev Mol Cell Biol Jun. 2003 457-467 4.

Saunders, L. R. and G. N. Barber. The dsRNA binding protein family: critical roles, diverse cellular functions Faseb J Jun. 2003 961-983 17.

Steinman, L. and S. Zamvil. Transcriptional analysis of targets in multiple sclerosis Nat Rev Immunol Jun. 2003 483-492 3.

Qi, Y. and B. Ding. Inhibition of cell growth and shoot development by a specific nucleotide sequence in a noncoding viroid RNA Plant Cell Jun. 2003 1360-1374 15.

Jackson, A. L., S. R. Bartz, J. Schelter, S. V. Kobayashi, J. Burchard, M. Mao, B. Li, G. Cavet and P. S. Linsley. Expression profiling reveals off-target gene regulation by RNAi Nat Biotechnol Jun. 2003 635-637 21.

Bashirullah, A., A. E. Pasquinelli, A. A. Kiger, N. Perrimon, G. Ruvkun and C. S. Thummel. Coordinate regulation of small temporal RNAs at the onset of *Drosophila* metamorphosis Dev Biol Jul. 1, 2003 1-8 259.

Sempere, L. F., N. S. Sokol, E. B. Dubrovsky, E. M. Berger and V. Ambros. Temporal regulation of microRNA expression in *Drosophila melanogaster* mediated by hormonal signals and broad-Complex gene activity Dev Biol Jul. 1, 2003 9-18 259.

Heetebrij, R. J., E. G. Talman, M. A. V Velzen, R. P. Van Gijlswijk, S. S. Snoeijers, M. Schalk, J. Wiegant, F. V D Rijke, R. M. Kerkhoven, A. K. Raap, H. J. Tanke, J. Reedijk and H. J. Houthoff. Platinum(II)-based coordination compounds as nucleic acid labeling reagents: synthesis, reactivity, and applications in hybridization assays Chembiochem Jul. 7, 2003 573-583 4.

Borodina, T. A., H. Lehrach and A. V. Soldatov. Ligation-based synthesis of oligonucleotides with block structure Anal Biochem Jul. 15, 2003 309-313 318.

Johnson, S. M., S. Y. Lin and F. J. Slack. The time of appearance of the *C. elegans* let-7 microRNA is transcriptionally controlled utilizing a temporal regulatory element in its promoter Dev Biol Jul. 15, 2003 364-379 259.

Carrington, J. C. and V. Ambros. Role of microRNAs in plant and animal development Science Jul. 18, 2003 336-338 301.

Smale, S. T. The establishment and maintenance of lymphocyte identity through gene silencing Nat Immunol Jul. 2003 607-615 4.

Bridge, A. J., S. Pebernard, A. Ducraux, A. L. Nicoulaz and R. Iggo. Induction of an interferon response by RNAi vectors in mammalian cells Nat Genet Jul. 2003 263-264 34.

Seitz, H., N. Youngson, S. P. Lin, S. Dalbert, M. Paulsen, J. P. Bachellerie, A. C. Ferguson-Smith and J. Cavaille. Imprinted microRNA genes transcribed antisense to a reciprocally imprinted retrotransposon-like gene Nat Genet Jul. 2003 261-262 34.

Zeng, Y., R. Yi and B. R. Cullen. MicroRNAs and small interfering RNAs can inhibit mRNA expression by similar mechanisms Proc Natl Acad Sci U S A Aug. 19, 2003 9779-9784 100.

Schramke, V. and R. Allshire. Hairpin RNAs and retrotransposon LTRs effect RNAi and chromatin-based gene silencing Science Aug. 22, 2003 1069-1074 301.

Wiznerowicz, M. and D. Trono. Conditional suppression of cellular genes: lentivirus vector-mediated drug-inducible RNA interference J Virol Aug. 2003 8957-8961 77.

Lau, N. C. and D. P. Bartel. Censors of the genome Sci Am Aug. 2003 34-41 289.

Houbaviy, H. B., M. F. Murray and P. A. Sharp. Embryonic stem cell-specific MicroRNAs Dev Cell Aug. 2003 351-358 5.

Aravin, A. A., M. Lagos-Quintana, A. Yalcin, M. Zavolan, D. Marks, B. Snyder, T. Gaasterland, J. Meyer and T. Tuschl. The small RNA profile during *Drosophila melanogaster* development Dev Cell Aug. 2003 337-350 5.

McManus, M. T. MicroRNAs and cancer Semin Cancer Biol Aug. 2003 253-258 13.

Baner, J., A. Isaksson, E. Waldenstrom, J. Jarvius, U. Landegren and M. Nilsson. Parallel gene analysis with allele-specific padlock probes and tag microarrays Nucleic Acids Res Sep. 1, 2003 e103 31.

Boutla, A., C. Delidakis and M. Tabler. Developmental defects by antisense-mediated inactivation of micro-RNAs 2 and 13 in *Drosophila* and the identification of putative target genes Nucleic Acids Res Sep. 1, 2003 4973-4980 31.

Palatnik, J. F., E. Allen, X. Wu, C. Schommer, R. Schwab, J. C. Carrington and D. Weigel. Control of leaf morphogenesis by microRNAs Nature Sep. 18, 2003 257-263 425.

Klein, R. J. and S. R. Eddy. Rsearch: finding homologs of single structured RNA sequences BMC Bioinformatics Sep. 22, 2003 44 4.

Caudy, A. A., R. F. Ketting, S. M. Hammond, A. M. Denli, A. M. Bathoorn, B. B. Tops, J. M. Silva, M. M. Myers, G. J. Hannon and R. H. Plasterk. A micrococcal nuclease homologue in RNAi effector complexes Nature Sep. 25, 2003 411-414 425.

Lee, Y., C. Ahn, J. Han, H. Choi, J. Kim, J. Yim, J. Lee, P. Provost, O. Radmark, S. Kim and V. N. Kim. The nuclear RNase III Drosha initiates microRNA processing Nature Sep. 25, 2003 415-419 425.

Sledz, C. A., M. Holko, M. J. De Veer, R. H. Silverman and B. R. Williams. Activation of the interferon system by short-interfering RNAs Nat Cell Biol Sep. 2003 834-839 5.

Bergmann, A. and M. E. Lane. HIDden targets of microRNAs for growth control Trends Biochem Sci Sep. 2003 461-463 28.

Khvorova, A., A. Reynolds and S. D. Jayasena. Functional siRNAs and miRNAs exhibit strand bias Cell Oct. 17, 2003 209-216 115.

Schwarz, D. S., G. Hutvagner, T. Du, Z. Xu, N. Aronin and P. D. Zamore. Asymmetry in the assembly of the RNAi enzyme complex Cell Oct. 17, 2003 199-208 115.

Abbott, A. L. Heterochronic genes Curr Biol Oct. 28, 2003 R824-825 13.

Hake, S. MicroRNAs: a role in plant development Curr Biol Oct. 28, 2003 R851-852 13.

Carthew, R. W. Making and breaking with nucleases and small RNAs Nat Struct Biol Oct. 2003 776-777 10.

Krichevsky, A. M., K. S. King, C. P. Donahue, K. Khrapko and K. S. Kosik. A microRNA array reveals extensive regulation of microRNAs during brain development Rna Oct. 2003 1274-1281 9.

Mattick, J. S. Challenging the dogma: the hidden layer of non-protein-coding RNAs in complex organisms Bioessays Oct. 2003 930-939 25.

Nelson, P., M. Kiriakidou, A. Sharma, E. Maniataki and Z. Mourelatos. The microRNA world: small is mighty Trends Biochem Sci Oct. 2003 534-540 28.

Michael, M. Z., O. C. SM, N. G. Van Holst Pellekaan, G. P. Young and R. J. James. Reduced accumulation of specific microRNAs in colorectal neoplasia Mol Cancer Res Oct. 2003 882-891 1.

Allinson, T. M., E. T. Parkin, A. J. Turner and N. M. Hooper. Adams family members as amyloid precursor protein alpha-secretases J Neurosci Res Nov. 1, 2003 342-352 74.

Kawasaki, H. and K. Taira. Retraction: Hes1 is a target of microRNA-23 during retinoic-acid-induced neuronal differentiation of NT2 cells Nature Nov. 6, 2003 100 426.

Saxena, S., Z. O. Jonsson and A. Dutta. Small RNAs with imperfect match to endogenous mRNA repress translation. Implications for off-target activity of small inhibitory RNA in mammalian cells J Biol Chem Nov. 7, 2003 44312-44319 278.

Basyuk, E., F. Suavet, A. Doglio, R. Bordonne and E. Bertrand. Human let-7 stem-loop precursors harbor features of RNase III cleavage products Nucleic Acids Res Nov. 15, 2003 6593-6597 31.

Stevenson, M. Dissecting HIV-1 through RNA interference Nat Rev Immunol Nov. 2003 851-858 3.

Wienholds, E., M. J. Koudijs, F. J. Van Eeden, E. Cuppen and R. H. Plasterk. The microRNA-producing enzyme Dicer1 is essential for zebrafish development Nat Genet Nov. 2003 217-218 35.

Gibbs, W. W. The unseen genome: gems among the junk Sci Am Nov. 2003 26-33 289.

Chang, J., P. Provost and J. M. Taylor. Resistance of human hepatitis delta virus RNAs to dicer activity J Virol Nov. 2003 11910-11917 77.

Wang, D., A. Urisman, Y. T. Liu, M. Springer, T. G. Ksiazek, D. D. Erdman, E. R. Mardis, M. Hickenbotham, V. Magrini, J. Eldred, J. P. Latreille, R. K. Wilson, D. Ganem and J. L. Derisi. Viral discovery and sequence recovery using DNA microarrays PLoS Biol Nov. 2003 E2 1.

Aukerman, M. J. and H. Sakai. Regulation of flowering time and floral organ identity by a MicroRNA and its APETALA2-like target genes Plant Cell Nov. 2003 2730-2741 15.

Finnegan, E. J. and M. A. Matzke. The small RNA world J Cell Sci Dec. 1, 2003 4689-4693 116.

Enright, A. J., B. John, U. Gaul, T. Tuschl, C. Sander and D. S. Marks. MicroRNA targets in *Drosophila* Genome Biol Epub 2003 Dec. 12, 2003 R1 5.

Rosok, O. and M. Sioud. Systematic identification of sense-antisense transcripts in mammalian cells Nat Biotechnol Jan (Epub Dec. 14, 2003) 2004 104-108 22.

Yi, R., Y. Qin, I. G. Macara and B. R. Cullen. Exportin-5 mediates the nuclear export of pre-microRNAs and short hairpin RNAs Genes Dev Dec. 15, 2003 3011-3016 17.

Cao, X., W. Aufsatz, D. Zilberman, M. F. Mette, M. S. Huang, M. Matzke and S. E. Jacobsen. Role of the DRM and CMT3 methyltransferases in RNA-directed DNA methylation Curr Biol Dec. 16, 2003 2212-2217 13.

Ye, K., L. Malinina and D. J. Patel. Recognition of small interfering RNA by a viral suppressor of RNA silencing Nature Dec. 18, 2003 874-878 426.

Johnston, R. J. and O. Hobert. A microRNA controlling left/right neuronal asymmetry in *Caenorhabditis elegans* Nature Dec. 18, 2003 845-849 426.

Xayaphoummine, A., T. Bucher, F. Thalmann and H. Isambert. Prediction and statistics of pseudoknots in RNA structures using exactly clustered stochastic simulations Proc Natl Acad Sci U S A Dec. 23, 2003 15310-15315 100.

Lewis, B. P., I. H. Shih, M. W. Jones-Rhoades, D. P. Bartel and C. B. Burge. Prediction of mammalian microRNA targets Cell Dec. 26, 2003 787-798 115.

Robinson, W. H., P. J. Utz and L. Steinman. Genomic and proteomic analysis of multiple sclerosis. Opinion Curr Opin Immunol Dec. 2003 660-667 15.

Gibbs, W. W. The unseen genome: beyond DNA Sci Am Dec. 2003 106-113 289.

Stark, A., J. Brennecke, R. B. Russell and S. M. Cohen. Identification of *Drosophila* MicroRNA targets PLoS Biol Dec. 2003 E60 1.

Stein, T. D. and J. A. Johnson. Genetic programming by the proteolytic fragments of the amyloid precursor protein: somewhere between confusion and clarity Rev Neurosci *no date in pubmed* 2003 317-341 14.

Szymanski, M., M. Z. Barciszewska, M. Zywicki and J. Barciszewski. Noncoding RNA transcripts J Appl Genet *No Datein Pubmed* 2003 1-19 44.

Griffiths-Jones, S. The microRNA Registry Nucleic Acids Res Jan. 1, 2004 D109-111 32.

Chen, C. Z., L. Li, H. F. Lodish and D. P. Bartel. MicroRNAs modulate hematopoietic lineage differentiation Science Jan. 2, 2004 83-86 303.

Kim, J., A. Krichevsky, Y. Grad, G. D. Hayes, K. S. Kosik, G. M. Church and G. Ruvkun. Identification of many microRNAs that copurify with polyribosomes in mammalian neurons Proc Natl Acad Sci U S A Jan. 6, 2004 360-365 101.

Ohno, M., E. A. Sametsky, L. H. Younkin, H. Oakley, S. G. Younkin, M. Citron, R. Vassar and J. F. Disterhoft. BACE1 deficiency rescues memory deficits and cholinergic dysfunction in a mouse model of Alzheimer's disease Neuron Jan. 8, 2004 27-33 41.

Vella, M. C., E. Y. Choi, S. Y. Lin, K. Reinert and F. J. Slack. The C. elegans microRNA let-7 binds to imperfect let-7 complementary sites from the lin-41 3'UTR Genes Dev Jan. 15, 2004 132-137 18.

Kao, S. C., A. M. Krichevsky, K. S. Kosik and L. H. Tsai. BACE1 suppression by RNA interference in primary cortical neurons J Biol Chem Jan. 16, 2004 1942-1949 279.

Hofacker, I. L., B. Priwitzer and P. F. Stadler. Prediction of locally stable RNA secondary structures for genome-wide surveys Bioinformatics Jan. 22, 2004 186-190 20.

Ruvkun, G., B. Wightman and I. Ha. The 20.years it took to recognize the importance of tiny RNAs Cell Jan. 23, 2004 S93-96, 92 p following S96 116.

Bartel, D. P. MicroRNAs: genomics, biogenesis, mechanism, and function Cell Jan. 23, 2004 281-297 116.

Han, M. H., S. Goud, L. Song and N. Fedoroff. The Arabidopsis double-stranded RNA-binding protein HYL1 plays a role in microRNA-mediated gene regulation Proc Natl Acad Sci U S A Jan. 27, 2004 1093-1098 101.

Hartig, J. S., I. Grune, S. H. Najafi-Shoushtari and M. Famulok. Sequence-specific detection of MicroRNAs by signal-amplifying ribozymes J Am Chem Soc Jan. 28, 2004 722-723 126.

Nishitsuji, H., T. Ikeda, H. Miyoshi, T. Ohashi, M. Kannagi and T. Masuda. Expression of small hairpin RNA by lentivirus-based vector confers efficient and stable gene-suppression of HIV-1 on human cells including primary non-dividing cells Microbes Infect Jan. 2004 76-85 6.

Ota, T., Y. Suzuki, T. Nishikawa, T. Otsuki, T. Sugiyama, R. Irie, A., et al. Complete sequencing and characterization of 21,243 full-length human cDNAs Nat Genet Jan. 2004 40-45 36.

Colciaghi, F., E. Marcello, B. Borroni, M. Zimmermann, C. Caltagirone, F. Cattabeni, A. Padovani and M. Di Luca. Platelet APP, ADAM 10 and BACE alterations in the early stages of Alzheimer disease Neurology Feb. 10, 2004 498-501 62.

Boden, D., O. Pusch, R. Silbermann, F. Lee, L. Tucker and B. Ramratnam. Enhanced gene silencing of HIV-1 specific siRNA using microRNA designed hairpins Nucleic Acids Res Feb. 13, 2004 1154-1158 32.

Sempere, L. F., S. Freemantle, I. Pitha-Rowe, E. Moss, E. Dmitrovsky and V. Ambros. Expression profiling of mammalian microRNAs uncovers a subset of brain-expressed microRNAs with possible roles in murine and human neuronal differentiation Genome Biol Epub 2004 Feb. 16, 2004 R13 5.

Scacheri, P. C., O. Rozenblatt-Rosen, N. J. Caplen, T. G. Wolfsberg, L. Umayam, J. C. Lee, C. M. Hughes, K. S. Shanmugam, A. Bhattacharjee, M. Meyerson and F. S. Collins. Short interfering RNAs can induce unexpected and divergent changes in the levels of untargeted proteins in mammalian cells Proc Natl Acad Sci U S A Feb. 17, 2004 1892-1897 101.

Xie, Z., L. K. Johansen, A. M. Gustafson, K. D. Kasschau, A. D. Lellis, D. Zilberman, S. E. Jacobsen and J. C. Carrington. Genetic and functional diversification of small RNA pathways in plants PLoS Biol May (Epub Feb. 18, 2004) 2004 E104 2.

Cawley, S., S. Bekiranov, H. H. Ng, P. Kapranov, E. A. Sekinger, D. Kampa, A. Piccolboni, V. Sementchenko, J. Cheng, A. J. Williams, R. Wheeler, B. Wong, J. Drenkow, M. Yamanaka, S. Patel, S. Brubaker, H. Tammana, G. Helt, K. Struhl and T. R. Gingeras. Unbiased mapping of transcription factor binding sites along human chromosomes 21 and 22 points to widespread regulation of noncoding RNAs Cell Feb. 20, 2004 499-509 116.

Dandekar, D. H., K. N. Ganesh and D. Mitra. HIV-1 Tat directly binds to NFkappaB enhancer sequence: role in viral and cellular gene expression Nucleic Acids Res Feb. 23, 2004 1270-1278 32.

Hutvagner, G., M. J. Simard, C. C. Mello and P. D. Zamore. Sequence-specific inhibition of small RNA function PLoS Biol Apr (Epub Feb. 24, 2004) 2004 E98 2.

Schmittgen, T. D., J. Jiang, Q. Liu and L. Yang. A high-throughput method to monitor the expression of microRNA precursors Nucleic Acids Res. Feb. 25, 2004 e43 32.

Stremlau, M., C. M. Owens, M. J. Perron, M. Kiessling, P. Autissier and J. Sodroski. The cytoplasmic body component TRIM5alpha restricts HIV-1 infection in Old World monkeys Nature Feb. 26, 2004 848-853 427.

Bohnsack, M. T., K. Czaplinski and D. Gorlich. Exportin 5 is a RanGTP-dependent dsRNA-binding protein that mediates nuclear export of pre-miRNAs Rna Feb. 2004 185-191 10.

Demidov, V. V. and M. D. Frank-Kamenetskii. Two sides of the coin: affinity and specificity of nucleic acid interactions Trends Biochem Sci Feb. 2004 62-71 29.

Maquat, L. E. Nonsense-mediated mRNA decay: splicing, translation and mRNP dynamics Nat Rev Mol Cell Biol Feb. 2004 89-99 5.

Nijholt, I., N. Farchi, M. Kye, E. H. Sklan, S. Shoham, B. Verbeure, D. Owen, B. Hochner, J. Spiess, H. Soreq and T. Blank. Stress-induced alternative splicing of acetylcholinesterase results in enhanced fear memory and long-term potentiation Mol Psychiatry Feb. 2004 174-183 9.

Sengupta, P. Taking sides in the nervous system with miRNA Nat Neurosci Feb. 2004 100-102 7.

Zerhouni, B., J. A. Nelson and K. Saha. Isolation of CD4-independent primary human immunodeficiency virus type 1 isolates that are syncytium inducing and acutely cytopathic for CD8+ lymphocytes J Virol Feb. 2004 1243-1255 78.

Jin, P., D. C. Zarnescu, S. Ceman, M. Nakamoto, J. Mowrey, T. A. Jongens, D. L. Nelson, K. Moses and S. T. Warren. Biochemical and genetic interaction between the fragile X mental retardation protein and the microRNA pathway Nat Neurosci Feb. 2004 113-117 7.

Lai, E. C., C. Wiel and G. M. Rubin. Complementary miRNA pairs suggest a regulatory role for miRNA:miRNA duplexes Rna Feb. 2004 171-175 10.

Metzler, M., M. Wilda, K. Busch, S. Viehmann and A. Borkhardt. High expression of precursor microRNA-155/BIC RNA in children with Burkitt lymphoma Genes Chromosomes Cancer Feb. 2004 167-169 39.

Doench, J. G. and P. A. Sharp. Specificity of microRNA target selection in translational repression Genes Dev Mar. 1, 2004 504-511 18.

Liang, X. S., J. O. Lian, Y. X. Zhou and M. B. Wan. Inhibitor RNA blocks the protein translation mediated by hepatitis C virus internal ribosome entry site in vivo World J Gastroenterol Mar. 1, 2004 664-667 10.

Calin, G. A., C. Sevignani, C. D. Dumitru, T. Hyslop, E. Noch, S. Yendamuri, M. Shimizu, S. Rattan, F. Bullrich, M. Negrini and C. M. Croce. Human microRNA genes are frequently located at fragile sites and genomic regions involved in cancers Proc Natl Acad Sci U S A Mar. 2, 2004 2999-3004 101.

Juarez, M. T., J. S. Kui, J. Thomas, B. A. Heller and M. C. Timmermans. microRNA-mediated repression of rolled leaf1 specifies maize leaf polarity Nature Mar. 4, 2004 84-88 428.

Kidner, C. A. and R. A. Martienssen. Spatially restricted microRNA directs leaf polarity through ARGONAUTE1 Nature Mar. 4, 2004 81-84 428.

Zamore, P. D. Plant RNAi: How a viral silencing suppressor inactivates siRNA Curr Biol Mar. 9, 2004 R198-200 14.

Wang, J. F., H. Zhou, Y. Q. Chen, Q. J. Luo and L. H. Qu. Identification of 20 microRNAs from Oryza sativa Nucleic Acids Res Mar. 12, 2004 1688-1695 32.

Jack, T. Molecular and genetic mechanisms of floral control Plant Cell Epub 2004 Mar. 12, 2004 S1-17 16 Suppl.

Roth, M. E., L. Feng, K. J. McConnell, P. J. Schaffer, C. E. Guerra, J. P. Affourtit, K. R. Piper, L. Guccione, J. Hariharan, M. J. Ford, S. W. Powell, H. Krishnaswamy, J. Lane, L. Guccione, G. Intrieri, J. S.

Merkel, C. Perbost, A. Valerio, B. Zolla, C. D. Graham, J. Hnath, C. Michaelson, R. Wang, B. Ying, C. Halling, C. E. Parman, D. Raha, B. Orr, B. Jedrzkiewicz, J. Liao, a. Tevelev, M. J. Mattessich, D. M. Kranz, M. Lacey, J. C. Kaufman, J. Kim, D. R. Latimer and P. M. Lizardi. Expression profiling using a hexamer-based universal microarray Nat Biotechnol Apr (Epub Mar. 14, 2004) 2004 418-426 22.

Rajewsky, N. and N. D. Socci. Computational identification of microRNA targets Dev Biol Mar. 15, 2004 529-535 267.

Winkler, W. C., A. Nahvi, A. Roth, J. A. Collins and R. R. Breaker. Control of gene expression by a natural metabolite-responsive ribozyme Nature Mar. 18, 2004 281-286 428.

Kuwabara, T., J. Hsieh, K. Nakashima, K. Taira and F. H. Gage. A small modulatory dsRNA specifies the fate of adult neural stem cells Cell Mar. 19, 2004 779-793 116.

Chen, X. A microRNA as a translational repressor of APETALA2 in Arabidopsis flower development Science Mar. 26, 2004 2022-2025 303.

Carmell, M. A. and G. J. Hannon. RNase III enzymes and the initiation of gene silencing Nat Struct Mol Biol Mar. 2004 214-218 11.

Davidson, B. L. and H. L. Paulson. Molecular medicine for the brain: silencing of disease genes with RNA interference Lancet Neurol Mar. 2004 145-149 3.

Kawasaki, H., R. Wadhwa and K. Taira. World of small RNAs: from ribozymes to siRNA and miRNA Differentiation Mar. 2004 58-64 72.

Meister, G., M. Landthaler, Y. Dorsett and T. Tuschl. Sequence-specific inhibition of microRNA- and siRNA-induced RNA silencing Rna Mar. 2004 544-550 10.

Nelson, P. T., A. G. Hatzigeorgiou and Z. Mourelatos. miRNP:mRNA association in polyribosomes in a human neuronal cell line Rna Mar. 2004 387-394 10.

Floyd, S. K. and J. L. Bowman. Gene regulation: ancient microRNA target sequences in plants Nature Apr. 1, 2004 485-486 428.

Dorsett, Y. and T. Tuschl. siRNAs: applications in functional genomics and potential as therapeutics Nat Rev Drug Discov Apr. 2004 318-329 3.

Mallory, A. C. and H. Vaucheret. MicroRNAs: something important between the genes Curr Opin Plant Biol Apr. 2004 120-125 7.

Ogita, S., H. Uefuji, M. Morimoto and H. Sano. Application of RNAi to confirm theobromine as the major intermediate for caffeine biosynthesis in coffee plants with potential for construction of decaffeinated varieties Plant Mol Biol Apr. 2004 931-941 54.

Storz, G., J. A. Opdyke and A. Zhang. Controlling mRNA stability and translation with small, noncoding RNAs Curr Opin Microbiol Apr. 2004 140-144 7.

Kim, V. N. MicroRNA precursors in motion: exportin-5 mediates their nuclear export Trends Cell Biol Apr. 2004 156-159 14.

Jabri, E. RISCy business Nat Struct Mol Biol Apr. 2004 300 11.

Nakahara, K. and R. W. Carthew. Expanding roles for miRNAs and siRNAs in cell regulation Curr Opin Cell Biol Apr. 2004 127-133 16.

Harley VR et al. Endocrine Reviews 2003;24(4):466-487.

Brennecke J. PLoS Biology 2005;3(3):e85.

Doench JG and Sharp PA. Genes Dev, 2004;18(5):504-11.

Enright AJ. Genome Biology 2003;5:R1.

Lai EC. Nature Genetics 2002;30:363-4.

Lai EC. Genome Biology 2004;5:115.

Lewis BP. Cell 2003;115:787-98.

Stark A. PLoS Biology 2003;1(3):397-409.

Vella MC. Chemistry & Biology 2004;11:1619-23.

Wagner CK et al. Endocrinology 2004;145(3):1046-9.

\* cited by examiner

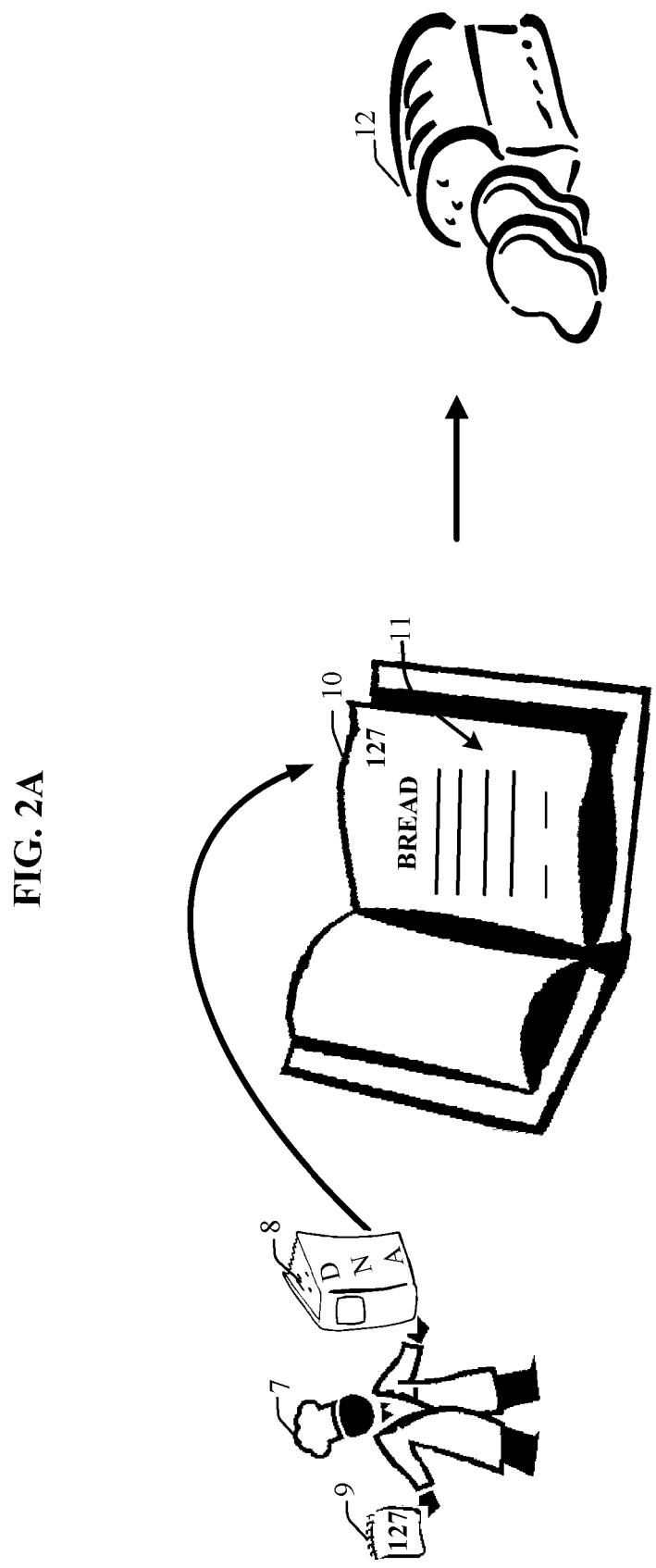

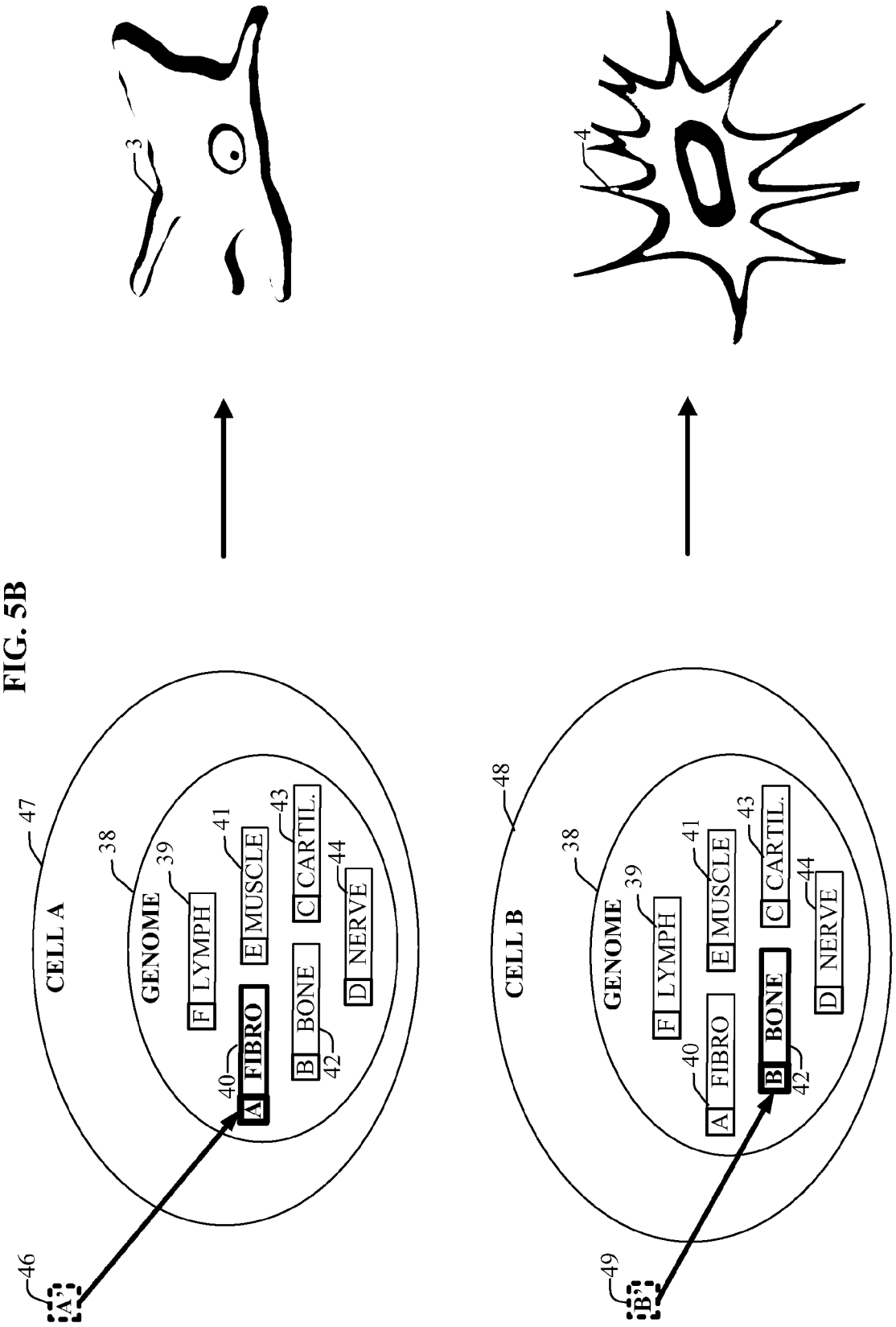

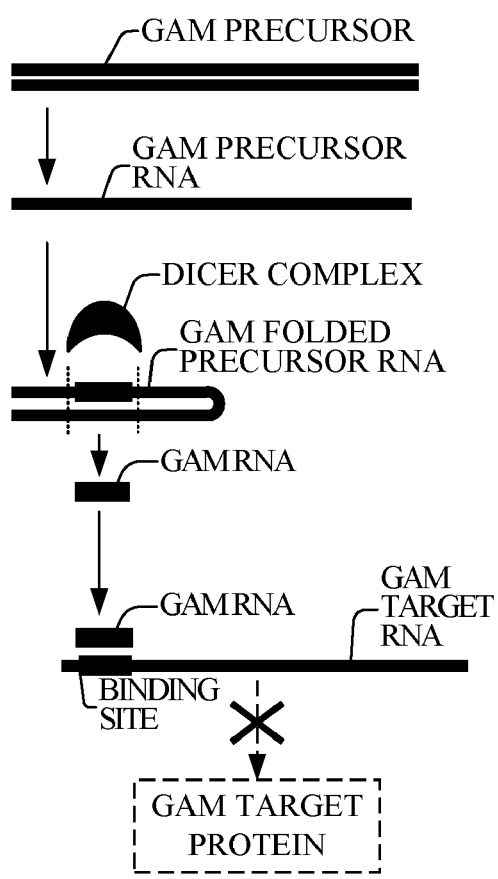
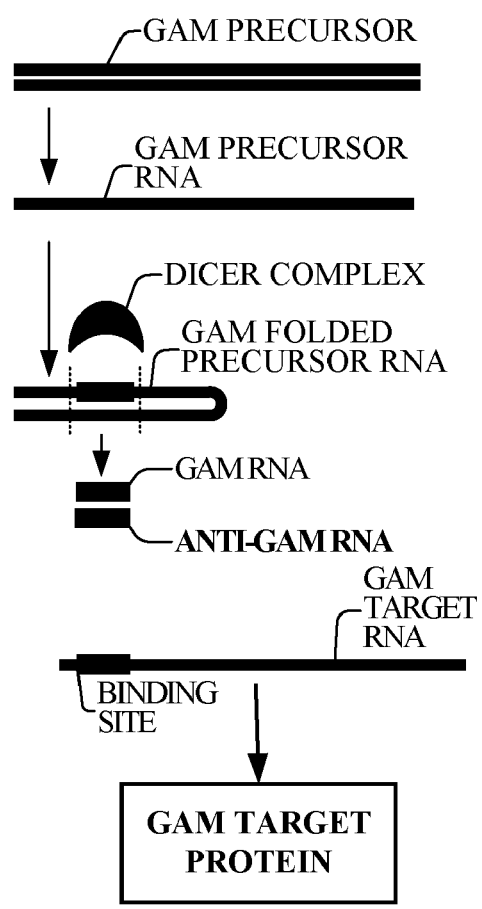
FIG. 20A
FIG. 20B

FIG. 21B

| GAM Detection Group | Published Hairpins Detection | Background Hairpins Filtering | Lab Validation of Human GAMs | | |
|---|---|---|---|---|---|
| | | | Sent | Positive | % Success |
| A | 382 | ~2850000 (95 %) | 101 | 37 | 37% |
| Overall | 440 | ~3000000 | 168 | 52 | 31% |

FIG.22B

| NUMBER | NAME | SEQ ID NO | SEQUENCE (5 TO 3) | SEQUENCED |
|---|---|---|---|---|
| 1 | has-miR-21 | 2254511 | TAGCTTATCAGACTGATGTTGA | + |
| 2 | has-miR-27b | 2254512 | TTCACAGTGGCTAAGTTCTGCA | + |
| 3 | has-miR-186 | 2254513 | AAAGAATTCTCCTTTTGGGCTT | + |
| 4 | has-miR-93 | 2254514 | AAGTGCTGTTCGTGCAGGTAGT | + |
| 5 | has-miR-26a | 2254515 | TCAAGTAATCCAGGATAGGCTG | + |
| 6 | has-miR-191 | 2254516 | AACGGAATCCCAAAAGCAGCTG | + |
| 7 | has-miR-31 | 2254517 | GGCAAGATGCTGGCATAGCTGT | + |
| 8 | has-miR-92 | 2254518 | TATTGCACTTGTCCCGGCCTGT | + |
| 9 | GAM3418-A | 2254519 | ATCACATTGCCAGGGATTACCA | + |
| 10 | GAM26-A | 2254520 | GAAGTTTGAAGCCTGTTGTTCA | + |
| 11 | GAM281-A | 2254521 | CACTGCACTCCAGCCTGGGCAA | |
| 12 | GAM7553-A | 2254522 | TAGGTAGTTTCCTGTTGTTGGG | + |
| 13 | GAM5385-A | 2254523 | TCACAGTGAACCGGTCTCTTTC | + |
| 14 | GAM2608-A | 2254524 | TAAGGTGCATCTAGTGCAGTTA | |
| 15 | GAM1032-A | 2254525 | CTAGACTGAAGCTCCTTGAGGA | + |
| 16 | GAM3431-A | 2254526 | TAATACTGCCGGGTAATGATGG | |
| 17 | GAM7933-A | 2254527 | TAGCAGCACATAATGGTTTGAA | |
| 18 | GAM3298-A | 2254528 | AAAGTGCTCATAGTGCAGGTAG | + |
| 19 | GAM7080-A | 2254529 | TTTCCACAGCGGCCAATTCTTC | + |
| 20 | GAM895-A | 2254530 | AGCTGCCAGTTGAAGAACATTT | |
| 21 | GAM3770-A | 2254531 | AAGTTAAGAGCTCCCAGGCCTG | |
| 22 | GAM337162-A | 2254532 | ACTGCACTCCAGCCTGGGCAAC | + |
| 23 | GAM8678-A | 2254533 | GTGTTCCAGGAAGTCGTCTTGA | |
| 24 | GAM2033-A | 2254534 | TCAAGCTCATTCCTCTAACCTC | |
| 25 | GAM7776-A | 2254535 | CATTGCACTCCAGCCTGGGCAA | + |
| 26 | GAM145-A | 2254536 | ACATGATCTCCTCACTCTAGGA | |
| 27 | GAM25-A | 2254537 | AATTGCTTGAACCCAGGAAGTG | + |
| 28 | GAM7352-A | 2254538 | TGTTTAAGTAGCTTATTTATCT | |
| 29 | GAM337624-A | 2254539 | TCTAAGAGAAAGGAAGTTCAGA | + |
| 30 | GAM1479-A | 2254540 | GAAGGCAGTAGGTTGTATAGTT | + |
| 31 | GAM2270-A | 2254541 | ATCACATTGCCAGTGATTACCC | + |
| 32 | GAM7591A | 2254542 | TTGGAGTAATTCAGTATAGGTT | + |
| 33 | GAM8285-A | 2254543 | AGTAGACAGTGGCAACATAGTC | |
| 34 | GAM6773-A | 2254544 | CTAGCCTGTTTGTCCTCACCCC | + |
| 35 | GAM336818-A | 2254545 | TGAGGTGGGATCCCGAGGCC | + |
| 36 | GAM336487-A | 2254546 | TGGCTAGGTAAGGGAAG | + |
| 37 | GAM337620-A | 2254547 | AATCATCATTATTTTGAAGTTTA | + |
| 38 | GAM336809-A | 2254548 | TAAGGCATTTTTATGGT | + |
| 39 | GAM5346-A | 2254549 | GCTGTTGTTAAGGGCACTTGGG | |
| 40 | GAM8554-A | 2254550 | TTCATGGGAGCAGGTGGTACAG | |
| 41 | GAM2701-A | 2254551 | ACTGCACTCCAGTCTGGGTGAC | |
| 42 | GAM7957-A | 2254552 | TCACTGCAACCTCTGCCTCCCG | |
| 43 | GAM391-A | 2254553 | CAGATCACATCCATCCGTCACC | |
| 44 | GAM6633-A | 2254554 | GCACTCAAGCCTGGGTTACAGA | |
| 45 | GAM19 | 2254555 | AGAGAGTGGCAGGTCTGTTCCT | |
| 46 | GAM8358-A | 2254556 | GATGAGGCAGCACTTGGG | |
| 47 | GAM3229-A | 2254557 | TGAGGTGGGAGAATTGCTTGAA | |
| 48 | GAM7052-A | 2254558 | CATGTAATCCCAGCTACTCAGG | |
| 49 | GAM3027-A (mmu-miR-29c) | 2254559 | TAGCACCATTTGAAATCGGTTA | + |
| 50 | GAM21 (mmui-miR-130b) | 2254560 | CAGTGCAATGATGAAAGGGCAT | + |
| 51 | GAM oligonucleotide (mmu-miR 30e) | 2254561 | TGTAAACATCCTTGACTGGAAG | + |

FIG. 24A

EST72223 (705 nt.)

Chr.X

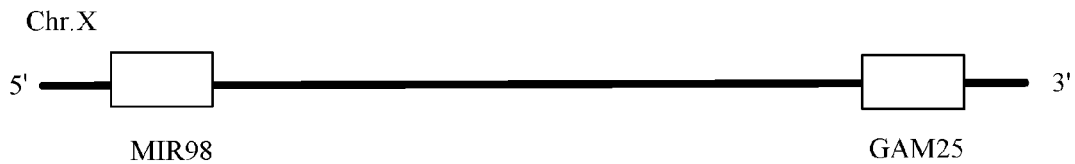

EST72223 sequence:

CCCTTATTAGAGGATTCTGCTCATGCCAGGGTGAGGTAGTAAGTTGTATTG
TTGTGGGGTAGGGATATTAGGCCCCAATTAGAAGATAACTATACAACT   MIR98
TACTACTTTCCCTGGTGTGTGGCATATTCACACTTAGTCTTAGCAGTGTTGCC
TCCATCAGACAAAGTTGTAGATGTTCCTTGGATAATTTGGACTGGAAGAAAAGA
GACATGGAAGGGGACAGATGGTGTTTAGGGTGAGGCAGATGTCATTATAAAGT
GACTTGTCTTTCATTAATTGGAGCATATAATTATTTTACCTTTGGGCATGAACTC
ATTTTGCTATTCTTCAACTGTGTAATGATTGCATTTTATTAGTAATAGAACAGGA
ATGTGTGCAAGGGAATGGAAAGCATACTTTAAGAATTTTGGGCCAGGCGCGGT
GGTTCATGCCTGTAATCCCAGCATTTTTGGGAGGCCGAGGCGGGTGGATCAC
CTGAGGTCAGGAGTTCGAGACCAACCTGGCCAACACGGCGAAACCCCGCCTC
TACTCAAATACAAAAATTAGCCAGGCTTGGTGACACTCGCCTGTGGTCCCAGC
TACTCAGGAGGCTGAGGCAGGAGAATTGCTTGAACCCAGGAAGTGGAG  GAM25
GCTTCAGTGAGCTGAGAACACGCCACTGCACTCCAGTCCTGGGCAAC
AGAGCAAGACTCTGTCTCAGGAAAAAAAAAG

FIG. 24B

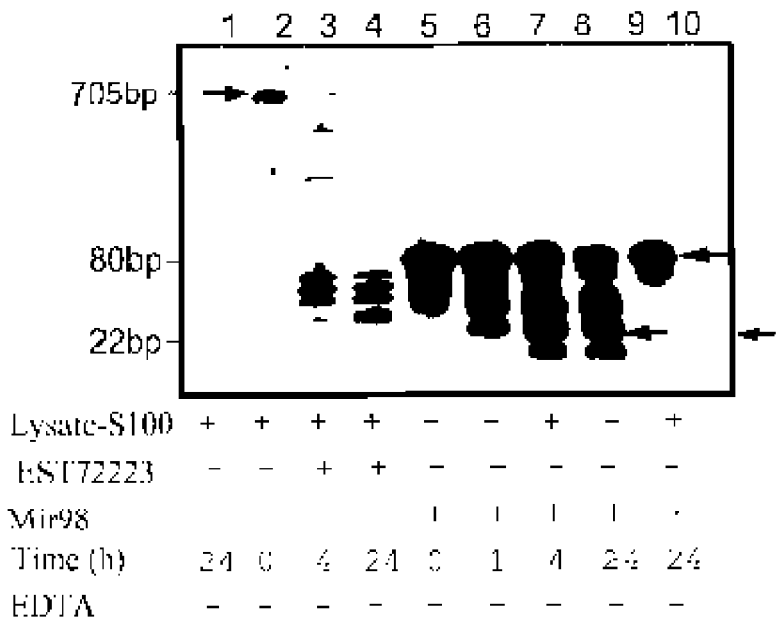

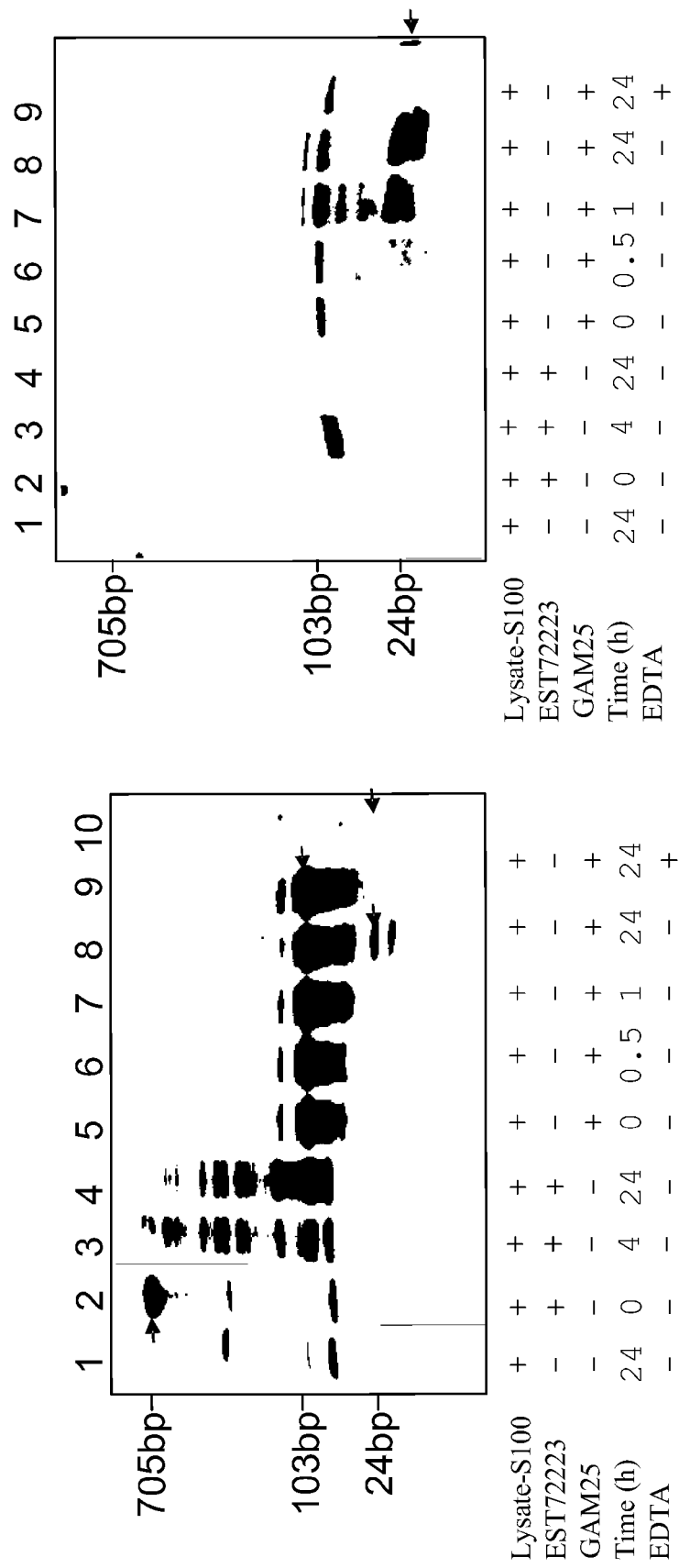

BIOINFORMATICALLY DETECTABLE GROUP OF NOVEL REGULATORY OLIGONUCLEOTIDES AND USES THEREOF

CROSS REFERENCE TO RELATED APPLICATIONS

The present application is a continuation-in-part of U.S. application Ser. No. 10/708,204, filed Feb. 16, 2004, and a continuation of U.S. application Ser. No. 10/707,980, filed Jan. 29, 2004, and continuation-in-part of U.S. application Ser. No. 10/707,975 now abandoned, filed Jan. 29, 2004, and continuation-in-part of U.S. application Ser. No. 10/707,147, filed Nov. 24, 2003, and continuation-in-part of International Applc. No. PCT/IL2003/000970, filed Nov. 16, 2003, which is a continuation of U.S. application Ser. No. 10/604,985 now abandoned filed Aug. 29, 2003, which is a continuation-in-part of U.S. application Ser. No. 10/651,227 filed Aug. 29, 2003, which is a continuation of U.S. application Ser. No. 10/605,924 filed Aug. 29, 2003; which is a continuation-in-part of U.S. application Ser. No. 10/649,653 filed Aug. 28, 2003; which is a continuation of U.S. application Ser. No. 10/605,923 filed Aug. 28, 2003; which is a continuation-in-part of U.S. application Ser. No. 10/604,926 filed Aug. 27, 2003; which is a continuation of U.S. application Ser. No. 10/345,201 filed Jan. 16, 2003, which is a continuation-in-part of U.S. application Ser. No. 10/321,503 filed Dec. 18, 2002, which is a continuation-in-part of U.S. application Ser. No. 10/310,914 filed Dec. 6, 2002, which is a continuation-in-part of U.S. application Ser. No. 10/293,338 filed Nov. 14, 2002, which is a continuation of U.S. application Ser. No. 10/604,727 filed Aug. 13, 2003. U.S. application Ser. No. 10/293,338 is also a continuation of U.S. application Ser. No. 10/604,726 filed Aug. 13, 2003. U.S. application Ser. No. 10/604,985 claims the benefit of U.S. Provisional Applc. Ser. No. 60/468,251 filed May 7, 2003. Each of these applications is incorporated herein by reference.

REFERENCES CITED

Altschul, S. F., Gish, W., Miller, W., Myers, E. W., and Lipman, D. J. (1990). Basic local alignment search tool. J. Mol. Biol. 215, 403-410.

Ambros, V., Lee, R. C., Lavanway, A., Williams, P. T., and Jewell, D. (2003). MicroRNAs and Other Tiny Endogenous RNAs in C. elegans 1. Curr. Biol. 13, 807-818.

Dan Gusfield, Algorithms on strings, trees, and sequences: computer science and computational biology, Cambridge University Press, 1997.

Elbashir, S. M., Lendeckel, W., and Tuschl, T. (2001). RNA interference is mediated by 21- and 22-nucleotide RNAs. Genes Dev. 15, 188-200.

Gibbs, W. W. (2003). The unseen genome: gems among the junk. Sci. Am. 289, 46-53.

Gussow, D. and Clackson, T. (1989). Direct clone characterization from plaques and colonies by the polymerase chain reaction. Nucleic Acids Res. 17, 4000.

Hamosh A, Scott A F, Amberger J, Bocchini C, Valle D and McKusick V A. (2002). Online Mendelian Inheritance in Man (OMIM), a knowledgebase of human genes and genetic disorders. Nucleic Acids Res. 30: 52-55.

Jenuth, J. P. (2000). The NCBI. Publicly available tools and resources on the Web. Methods Mol. Biol. 132, 301-312.

Kirkness, E. F. and Kerlavage, A. R. (1997). The TIGR human cDNA database. Methods Mol. Biol. 69, 261-268.

Lagos-Quintana, M., Rauhut, R., Lendeckel, W., and Tuschl, T. (2001). Identification of novel genes coding for small expressed RNAs. Science 294, 853-858.

Lau, N. C., Lim, L. P., Weinstein, E. G., and Bartel, D. P. (2001). An abundant class of tiny RNAs with probable regulatory roles in Caenorhabditis elegans. Science 294, 858-862.

Lau, N. C. and Bartel, D. P. (2003). Censors of the genome. Sci. Am. 289, 34-41.

Lim, L. P., Glasner, M. E., Yekta, S., Burge, C. B., and Bartel, D. P. (2003). Vertebrate microRNA genes. Science 299, 1540.

Mathews, D. H., Sabina, J., Zuker, M., and Turner, D. H. (1999). Expanded sequence dependence of thermodynamic parameters improves prediction of RNA secondary structure. J. Mol. Biol. 288, 911-940.

Reinhart, B. J., Slack, F. J., Basson, M., Pasquinelli, A. E., Bettinger, J. C., Rougvie, A. E., Horvitz, H. R., and Ruvkun, G. (2000). The 21-nucleotide let-7 RNA regulates developmental timing in Caenorhabditis elegans. Nature 403, 901-906.

Southern, E. M. (1992). Detection of specific sequences among DNA fragments separated by gel electrophoresis. 1975. Biotechnology 24, 122-139.

Tom M. Mitchell, Machine Learning, McGraw Hill, 1997.

Wightman, B., Ha, I., and Ruvkun, G. (1993). Posttranscriptional regulation of the heterochronic gene lin-14 by lin-4 mediates temporal pattern formation in C. elegans. Cell 75, 855-862.

Zhang, H., Kolb, F. A., Brondani, V., Billy, E., and Filipowicz, W. (2002). Human Dicer preferentially cleaves dsRNAs at their termini without a requirement for ATP. EMBO J. 21, 5875-5885.

Zuker, M. (2003). Mfold web server for nucleic acid folding and hybridization prediction. Nucleic Acids Res. 31, 3406-3415.

BACKGROUND OF THE INVENTION

1. Field of the Invention

The present invention relates to a group of bioinformatically detectable novel human oligonucleotides, here identified as Genomic Address Messenger or GAM oligonucleotides.

All of which are believed to be related to the micro RNA (miRNA) group of oligonucleotides.

2. Description of Prior Art

Micro RNAs (miRNA), are short ~22 nt non-coding regulatory RNA oligonucleotides, found in a wide range of species, believed to function as specific gene translation repressors, sometimes involved in cell-differentiation.

The ability to detect novel miRNAs is limited by the methodologies used to detect such oligonucleotides. All miRNAs identified so far either present a visibly discernable whole body phenotype, as do Lin-4 and Let-7 (Wightman, B., Ha, I., and Ruvkun, G., Cell 75:855-862 (1993); Reinhart et al. Nature 403: 901-906 (2000)), or produce sufficient quantities of RNA so as to be detected by the standard molecular biological techniques.

Studies reporting miRNAs (Lau et al., Science 294:858-862 (2001), Lagos-Quintana et al., Science 294: 853-858 (2001)) discovered 93 miRNAs in several species, by sequencing a limited number of clones (300 by Lau and 100 by Lagos-Quintana) of small segments (i.e. size fractionated) RNA. MiRNAs detected in these studies therefore, represent the more prevalent among the miRNA oligonucleotide family, and can not be much rarer than 1% of all small ~20 nt-long RNA oligonucleotides.

The aforesaid studies provide no basis for detection of miRNA oligonucleotides which either do not present a visually discernable whole body phenotype, or are rare (e.g. rarer than 0.1% of all size fractionated ~20 nt-long RNA segments expressed in the tissues examined), and therefore do not produce significant enough quantities of RNA so as to be detected by standard biological techniques.

Reference is made to the sequence listing submitted herewith. The sequence listing consists of a file named "SequenceListing.txt" (342,255 KB, Jul. 15, 2009), and is hereby incorporated by reference herein.

Brief Description of Sequence Listing, Large Tables and Computer Program Listing A sequence listing is attached to the present invention, comprising 2254510 genomic sequences, is contained in a file named SEQ_LIST.txt (342238 KB, 31 Mar. 2004), and is hereby incorporated by reference herein.

Large tables relating to genomic sequences are attached to the present application, appear in 11 table files (size, creation date), incorporated herein: TABLE__1.txt (35,428 KB, Mar. 31, 2004); TABLE__2.txt (165,249 KB, Mar. 31, 2004); TABLE__3.txt (2,837 KB, Mar. 31, 2004); TABLE__4.txt (8,105 KB, Mar. 31, 2004); TABLE__5.txt (3,048 KB, Mar. 31, 2004); TABLE__6.txt (169,488 KB, Mar. 31, 2004); TABLE__7.txt (268,106 KB, Mar. 31, 2004); TABLE__8__1.txt (378,907 KB, Oct. 25, 2005); TABLE__8__2.txt (374,279 KB, Oct. 25, 2005); TABLE__9__1.txt (419,922 KB, Oct. 25, 2005); TABLE__9__2.txt (415,145 KB, Oct. 25, 2005); TABLE__10.txt (4,315 KB, Mar. 31, 2004) and TABLE__11.txt (36 KB, Mar. 31, 2004), all of which are incorporated by reference herein.

A computer program listing of a computer program constructed and operative in accordance with a preferred embodiment of the present invention is enclosed on an electronic medium in computer readable form, and is hereby incorporated by reference herein. The computer program listing is contained in 6 files, the name, sizes and creation date of which are as follows: AUXILARY_FILES.txt (117K, 14-Nov-03); EDIT_DISTANCE.txt (144K, 24-Nov-03); FIRST-K.txt (96K, 24-Nov-03); HAIRPIN_PREDICTION.txt (19K, 25-Mar-04); TWO_PHASED_SIDE_SELECTOR.txt (4K, 14-Nov-03); and TWO_PHASED_PREDICTOR.txt (74K, 14-Nov-03).

SUMMARY OF THE INVENTION

The present invention discloses over a thousand novel human regulatory microRNA-like (miRNA) oligonucleotides referred to here as Genomic Address Messenger (GAM) oligonucleotides, which GAM oligonucleotides are detectable using a novel bioinformatic approach, and go undetected by conventional molecular biology methods. Each GAM oligonucleotide specifically inhibits translation of one of more target genes by hybridization of an RNA transcript encoded by the GAM, to a site located in an untranslated region (UTR) of the mRNA of one or more of the target genes.

Accordingly, the invention provides several substantially pure nucleic acids (e.g., genomic DNA, cDNA or synthetic DNA) each comprising a novel human GAM oligonucleotide, vectors comprising the DNAs, probes comprising the DNAs, a method and system for selectively modulating translation of known target genes utilizing the vectors, and a method and system utilizing the GAM probes to modulate expression of target genes.

The present invention represents a scientific breakthrough, disclosing novel miRNA-like oligonucleotides the number of which is dramatically larger than previously believed existed. Prior-art studies reporting miRNAs ((Lau et al., Science 294: 858-862 (2001), Lagos-Quintana et al., Science 294: 853-858 (2001)) discovered 93 miRNAs in several species, including 21 in human, using conventional molecular biology methods, such as cloning and sequencing.

Molecular biology methodologies employed by these studies are limited in their ability to detect rare miRNA oligonucleotides, since these studies relied on sequencing of a limited number of clones (300 clones by Lau and 100 clones by Lagos-Quintana) of small segments (i.e. size fractionated) of RNA. MicroRNAs detected in these studies therefore, represent the more prevalent among the miRNA oligonucleotide family, and are typically not be much rarer than 1% of all small ~20 nt-long RNA oligonucleotides present in the tissue from the RNA was extracted.

Recent studies state the number of miRNA oligonucleotides to be limited, and describe the limited sensitivity of available methods for detection of miRNA: The estimate of 255 human miRNA oligonucleotides is an upper bound implying that no more than 40 miRNA oligonucleotides remain to be identified in mammals (Lim et al., Science, 299:1540 (2003)); Estimates place the total number of vertebrate miRNA genes at about 200-250 (Ambros et al. Curr. Biol. 13:807-818 (2003)); and Confirmation of very low abundance miRNAs awaits the application of detection methods more sensitive than Northern blots (Ambros et al. Curr. Biol. 13:807-818 (2003)).

The oligonucleotides of the present invention represent a revolutionary new dimension of genomics and of biology: a dimension comprising a huge number of non-protein coding oligonucleotides which modulate expression of thousands of proteins and are associated with numerous major diseases. This new dimension disclosed by the present invention dismantles a central dogma that has dominated life-sciences during the past 50 years, a dogma which has emphasized the importance of protein coding regions of the genome, holding non-protein coding regions to be of little consequence, often dubbing them junk DNA.

Indeed, only in November, 2003 has this long held belief as to the low importance of non-protein coding regions been vocally challenged. As an example, an article titled The Unseen Genome—Gems in the Junk (Gibbs, W. W. Sci. Am. 289:46-53 (2003)) asserts that the failure to recognize the importance of non-protein-coding regions may well go down as one of the biggest mistakes in the history of molecular biology. Gibbs further asserts that what was dammned as junk because it was not understood, may in fact turn out to be the very basis of human complexity. The present invention provides a dramatic leap in understanding specific important roles of non-protein coding regions.

An additional scientific breakthrough of the present invention is a novel conceptual model disclosed by the present invention, which conceptual model is preferably used to encode in a genome the determination of cell-differentiation, utilizing oligonucleotides and polynucleotides of the present invention.

In various preferred embodiments, the present invention seeks to provide an improved method and system for specific modulation of the expression of specific target genes involved in significant human diseases. It also provides an improved method and system for detection of the expression of novel oligonucleotides of the present invention, which modulate these target genes. In many cases the target genes may be known and fully characterized, however in alternative embodiments of the present invention, unknown or less well characterized genes may be targeted.

A Nucleic acid is defined as a ribonucleic acid (RNA) molecule, or a deoxyribonucleic acid (DNA) molecule, or complementary deoxyribonucleic acid (cDNA), comprising either naturally occurring nucleotides or non-naturally occurring nucleotides.

Substantially pure nucleic acid, Isolated Nucleic Acid, Isolated Oligoucleotide and Isolated Polynucleotide are defined as a nucleic acid that is free of the genome of the organism from which the nucleic acid is derived, and include, for example, a recombinant nucleic acid which is incorporated into a vector, into an autonomously replicating plasmid or virus, or into the genomic nucleic acid of a prokaryote or eukaryote at a site other than its natural site; or which exists as a separate molecule (e.g., a cDNA or a genomic or cDNA fragment produced by PCR or restriction endonuclease digestion) independent of other nucleic acids.

An Oligonucleotide is defined as a nucleic acid comprising 2-139 nucleotides, or preferably 16-120 nucleotides. A Polynucleotide is defined as a nucleic acid comprising 140-5000 nucleotides, or preferably 140-1000 nucleotides.

A Complementary sequence is defined as a first nucleotide sequence which reverses complementary of a second nucleotide sequence: the first nucleotide sequence is reversed relative to a second nucleotide sequence, and wherein each nucleotide in the first nucleotide sequence is complementary to a corresponding nucleotide in the second nucleotide sequence (e.g. ATGGC is the complementary sequence of GCCAT).

Hybridization, Binding and Annealing are defined as hybridization, under in-vivo physiologic conditions, of a first nucleic acid to a second nucleic acid, which second nucleic acid is at least partially complementary to the first nucleic acid.

A Hairpin Structure is defined as an oligonucleotide having a nucleotide sequence that is 50-140 nucleotides in length, the first half of which nucleotide sequence is at least partially complementary to the second part thereof, thereby causing the nucleic acid to fold onto itself, forming a secondary hairpin structure.

A Hairpin Shaped Precursor is defined as a Hairpin Structure which is processed by a Dicer enzyme complex, yielding an oligonucleotide which is about 19 to about 24 nucleotides in length.

"Inhibiting translation" is defined as the ability to prevent synthesis of a specific protein encoded by a respective gene by means of inhibiting the translation of the mRNA of this gene. For example, inhibiting translation may include the following steps: (1) a DNA segment encodes an RNA, the first half of whose sequence is partially complementary to the second half thereof; (2) the precursor folds onto itself forming a hairpin-shaped precursor; (3) a Dicer enzyme complex cuts the hairpin shaped precursor yielding an oligonucleotide that is approximately 22 nt in length; (4) the oligonucleotide binds complementarily to at least one binding site, having a nucleotide sequence that is at least partially complementary to the oligonucleotide, which binding site is located in the mRNA of a target gene, preferably in the untranslated region (UTR) of a target gene, such that the binding inhibits translation of the target protein.

A "Translation inhibitor site" is defined as the minimal nucleotide sequence sufficient to inhibit translation.

There is thus provided in accordance with a preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the oligonucleotide has at least 80% sequence identity with a nucleotide sequence selected from the group consisting of SEQ ID NOs: 1-14676.

There is further provided in accordance with another preferred embodiment of the present invention a bioinformatically detectable isolated oligonucleotide which is endogenously processed from a hairpin-shaped precursor, and anneals to a portion of a mRNA transcript of a target gene selected from the group consisting of genes shown in Table 11, Row 1, wherein binding of the oligonucleotide to the mRNA transcript represses expression of the target gene, and wherein the oligonucleotide has at least 80% sequence identity with a nucleotide sequence selected from the group consisting of SEQ ID NOs: 1-14676.

There is still further provided in accordance with another preferred embodiment of the present invention a bioinformatically detectable isolated oligonucleotide having a nucleotide sequence selected from the group consisting of SEQ ID NOs: 1-14676.

There is additionally provided in accordance with another preferred embodiment of the present invention a bioinformatically detectable first oligonucleotide which is a portion of a mRNA transcript of a target gene, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs: 1-14676.

There is moreover provided in accordance with another preferred embodiment of the present invention a bioinformatically detectable first oligonucleotide which is a portion of a mRNA transcript of a target gene selected from the group consisting of genes shown in Table 11 row 1, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs: 1-14676.

There is further provided in accordance with another preferred embodiment of the present invention a bioinformatically detectable oligonucleotide having a nucleotide sequence selected from the group consisting of SEQ ID NOs: 1-14676.

There is still further provided in accordance with another preferred embodiment of the present invention a bioinformatically detectable isolated oligonucleotide which anneals to a portion of a mRNA transcript of a target gene associated with Addisons disease, which target gene is selected from the group consisting of genes shown in Table 11, row 2, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3 and 14677-15272, and (b) the complement of a sequence selected from the group consisting of SEQ ID NOs: 378232 and 377922-378929.

There is additionally provided in accordance with another preferred embodiment of the present invention a bioinformatically detectable first oligonucleotide which is a portion of a mRNA transcript of a target gene selected from the group consisting of genes shown in Table 11 row 2, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3 and 14677-15272.

There is moreover provided in accordance with another preferred embodiment of the present invention a bioinformatically detectable isolated oligonucleotide which anneals to a portion of a mRNA transcript of a target gene associated with Adenovirus, which target gene is selected from the group consisting of genes shown in Table 11, row 3, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 4 and 15273-15329, and (b) the complement of a sequence selected from the group consisting of SEQ ID NOs: 378982 and 378930-379029.

There is further provided in accordance with another preferred embodiment of the present invention a bioinformatically detectable first oligonucleotide which is a portion of a mRNA transcript of a target gene selected from the group consisting of genes shown in Table 11 row 3, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:4 and 15273-15329.

There is still further provided in accordance with another preferred embodiment of the present invention a bioinformatically detectable isolated oligonucleotide which anneals to a portion of a mRNA transcript of a target gene associated with Adrenal cortical carcinoma, which target gene is selected from the group consisting of genes shown in Table 11, row 4, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4 and 15330-16657, and (b) the complement of a sequence selected from the group consisting of SEQ ID NOs: 379943, 380776 and 379030-381893.

There is additionally provided in accordance with another preferred embodiment of the present invention a bioinformatically detectable first oligonucleotide which is a portion of a mRNA transcript of a target gene selected from the group consisting of genes shown in Table 11 row 4, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4 and 15330-16657.

There is moreover provided in accordance with another preferred embodiment of the present invention a bioinformatically detectable isolated oligonucleotide which anneals to a portion of a mRNA transcript of a target gene associated with Aids, which target gene is selected from the group consisting of genes shown in Table 11, row 5, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 6, 7, 8, 9 and 16658-22991, and (b) the complement of a sequence selected from the group consisting of SEQ ID NOs: 383072, 383073, 384083, 384982, 395441, 396067, 397674, 398184 and 381894-400528.

There is further provided in accordance with another preferred embodiment of the present invention a bioinformatically detectable first oligonucleotide which is a portion of a mRNA transcript of a target gene selected from the group consisting of genes shown in Table 11 row 5, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 6, 7, 8, 9 and 16658-22991.

There is still further provided in accordance with another preferred embodiment of the present invention a bioinformatically detectable isolated oligonucleotide which anneals to a portion of a mRNA transcript of a target gene associated with Alzheimer, which target gene is selected from the group consisting of genes shown in Table 11, row 6, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 6, 7, 8, 9 and 22992-34834, and (b) the complement of a sequence selected from the group consisting of SEQ ID NOs: 404508, 420735, 423944, 435112, 440-497, 441931, 446-451, 450239 and 400529-460892.

There is additionally provided in accordance with another preferred embodiment of the present invention a bioinformatically detectable first oligonucleotide which is a portion of a mRNA transcript of a target gene selected from the group consisting of genes shown in Table 11 row 6, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 6, 7, 8, 9 and 22992-34834.

There is moreover provided in accordance with another preferred embodiment of the present invention a bioinformatically detectable isolated oligonucleotide which anneals to a portion of a mRNA transcript of a target gene associated with Amyloidosis, which target gene is selected from the group consisting of genes shown in Table 11, row 7, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5 and 34835-36785, and (b) the complement of a sequence selected from the group consisting of SEQ ID NOs: 460919, 462509, 463079, 463677, 463827 and 460893-465-427.

There is further provided in accordance with another preferred embodiment of the present invention a bioinformatically detectable first oligonucleotide which is a portion of a mRNA transcript of a target gene selected from the group consisting of genes shown in Table 11 row 7, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5 and 34835-36785.

There is still further provided in accordance with another preferred embodiment of the present invention a bioinformatically detectable isolated oligonucleotide which anneals to a portion of a mRNA transcript of a target gene associated with Amyotrophic Lateral Sclerosis, which target gene is selected from the group consisting of genes shown in Table 11, row 8, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 4, 7 and 36786-39744, and (b) the complement of a sequence selected from the group consisting of SEQ ID NOs: 467837, 470539, 470925 and 465-428-471746.

There is additionally provided in accordance with another preferred embodiment of the present invention a bioinformatically detectable first oligonucleotide which is a portion of a mRNA transcript of a target gene selected from the group consisting of genes shown in Table 11 row 8, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 4, 7 and 36786-39744.

There is moreover provided in accordance with another preferred embodiment of the present invention a bioinformatically detectable isolated oligonucleotide which anneals to a portion of a mRNA transcript of a target gene associated with Anal cancer, which target gene is selected from the group consisting of genes shown in Table 11, row 9, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1 and 39745-39979, and (b) the complement of a sequence selected from the group consisting of SEQ ID NOs: 471800 and 471747-471906.

There is further provided in accordance with another preferred embodiment of the present invention a bioinformatically detectable first oligonucleotide which is a portion of a mRNA transcript of a target gene selected from the group consisting of genes shown in Table 11 row 9, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1 and 39745-39979.

There is still further provided in accordance with another preferred embodiment of the present invention a bioinformatically detectable isolated oligonucleotide which anneals to a portion of a mRNA transcript of a target gene associated with Anorexia Nervosa, which target gene is selected from the group consisting of genes shown in Table 11, row 10, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 4, 8 and 39980-40538, and (b) the complement of a sequence selected from the group consisting of SEQ ID NOs: 472-404, 472-408 and 471907-473060.

There is additionally provided in accordance with another preferred embodiment of the present invention a bioinformatically detectable first oligonucleotide which is a portion of a mRNA transcript of a target gene selected from the group consisting of genes shown in Table 11 row 10, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:4, 8 and 39980-40538.

There is moreover provided in accordance with another preferred embodiment of the present invention a bioinformatically detectable isolated oligonucleotide which anneals to a portion of a mRNA transcript of a target gene associated with Asthma, which target gene is selected from the group consisting of genes shown in Table 11, row 11, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 7, 9 and 40539-44830, and (b) the complement of a sequence selected from the group consisting of SEQ ID NOs: 473069, 474333, 474580, 478106, 481841, 482515 and 473061-483-490.

There is further provided in accordance with another preferred embodiment of the present invention a bioinformatically detectable first oligonucleotide which is a portion of a mRNA transcript of a target gene selected from the group consisting of genes shown in Table 11 row 11, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 7, 9 and 40539-44830.

There is still further provided in accordance with another preferred embodiment of the present invention a bioinformatically detectable isolated oligonucleotide which anneals to a portion of a mRNA transcript of a target gene associated with Atopic dermatitis, which target gene is selected from the group consisting of genes shown in Table 11, row 12, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 7 and 44831-46240, and (b) the complement of a sequence selected from the group consisting of SEQ ID NOs: 483-494, 484-470, 485-473 and 483-491-486113.

There is additionally provided in accordance with another preferred embodiment of the present invention a bioinformatically detectable first oligonucleotide which is a portion of a mRNA transcript of a target gene selected from the group consisting of genes shown in Table 11 row 12, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 7 and 44831-46240.

There is moreover provided in accordance with another preferred embodiment of the present invention a bioinformatically detectable isolated oligonucleotide which anneals to a portion of a mRNA transcript of a target gene associated with Atrial fibrillation, which target gene is selected from the group consisting of genes shown in Table 11, row 13, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1 and 46241-46979, and (b) the complement of a sequence selected from the group consisting of SEQ ID NOs: 486156 and 486114-487523.

There is further provided in accordance with another preferred embodiment of the present invention a bioinformatically detectable first oligonucleotide which is a portion of a mRNA transcript of a target gene selected from the group consisting of genes shown in Table 11 row 13, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1 and 46241-46979.

There is still further provided in accordance with another preferred embodiment of the present invention a bioinformatically detectable isolated oligonucleotide which anneals to a portion of a mRNA transcript of a target gene associated with Autism, which target gene is selected from the group consisting of genes shown in Table 11, row 14, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3, 7, 9 and 46980-50847, and (b) the complement of a sequence selected from the group consisting of SEQ ID NOs: 487792, 489338, 495239 and 487524-497639.

There is additionally provided in accordance with another preferred embodiment of the present invention a bioinformatically detectable first oligonucleotide which is a portion of a mRNA transcript of a target gene selected from the group consisting of genes shown in Table 11 row 14, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3, 7, 9 and 46980-50847.

There is moreover provided in accordance with another preferred embodiment of the present invention a bioinformatically detectable isolated oligonucleotide which anneals to a portion of a mRNA transcript of a target gene associated with Barrett Esophagus, which target gene is selected from the group consisting of genes shown in Table 11, row 15, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 4 and 50848-52075, and (b) the complement of a sequence selected from the group consisting of SEQ ID NOs: 498378 and 497640-500427.

There is further provided in accordance with another preferred embodiment of the present invention a bioinformatically detectable first oligonucleotide which is a portion of a mRNA transcript of a target gene selected from the group consisting of genes shown in Table 11 row 15, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:4 and 50848-52075.

There is still further provided in accordance with another preferred embodiment of the present invention a bioinformatically detectable isolated oligonucleotide which anneals to a portion of a mRNA transcript of a target gene associated with Basal cell carcinoma, which target gene is selected from the group consisting of genes shown in Table 11, row 16, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1 and 52076-54148, and (b) the complement of a sequence selected from the group consisting of SEQ ID NOs: 503527 and 500428-504726.

There is additionally provided in accordance with another preferred embodiment of the present invention a bioinformatically detectable first oligonucleotide which is a portion of a mRNA transcript of a target gene selected from the group consisting of genes shown in Table 11 row 16, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1 and 52076-54148.

There is moreover provided in accordance with another preferred embodiment of the present invention a bioinformatically detectable isolated oligonucleotide which anneals to a portion of a mRNA transcript of a target gene associated with Beta Thalassemia, which target gene is selected from the group consisting of genes shown in Table 11, row 17, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1 and 54149-54833, and (b) the complement of a sequence selected from the group consisting of SEQ ID NOs: 504750 and 504727-505912.

There is further provided in accordance with another preferred embodiment of the present invention a bioinformatically detectable first oligonucleotide which is a portion of a mRNA transcript of a target gene selected from the group consisting of genes shown in Table 11 row 17, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1 and 54149-54833.

There is still further provided in accordance with another preferred embodiment of the present invention a bioinformatically detectable isolated oligonucleotide which anneals to a portion of a mRNA transcript of a target gene associated with Bipolar Disorder, which target gene is selected from the group consisting of genes shown in Table 11, row 18, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 6, 9 and 54834-59154, and (b) the complement of a sequence selected from the group consisting of SEQ ID NOs: 508649, 509702, 511790, 512551, 513055 and 505913-516790.

There is additionally provided in accordance with another preferred embodiment of the present invention a bioinformatically detectable first oligonucleotide which is a portion of a mRNA transcript of a target gene selected from the group consisting of genes shown in Table 11 row 18, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 6, 9 and 54834-59154.

There is moreover provided in accordance with another preferred embodiment of the present invention a bioinformatically detectable isolated oligonucleotide which anneals to a portion of a mRNA transcript of a target gene associated with Bladder cancer, which target gene is selected from the group consisting of genes shown in Table 11, row 19, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4, 6, 7 and 59155-64410, and (b) the complement of a sequence selected from the group consisting of SEQ ID NOs: 524632, 524817, 526807, 528540, 529737 and 516791-530989.

There is further provided in accordance with another preferred embodiment of the present invention a bioinformatically detectable first oligonucleotide which is a portion of a mRNA transcript of a target gene selected from the group consisting of genes shown in Table 11 row 19, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4, 6, 7 and 59155-64410.

There is still further provided in accordance with another preferred embodiment of the present invention a bioinformatically detectable isolated oligonucleotide which anneals to a portion of a mRNA transcript of a target gene associated with Breast cancer, which target gene is selected from the group consisting of genes shown in Table 11, row 20, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 8, 9 and 64411-78554, and (b) the complement of a sequence selected from the group consisting of SEQ ID NOs: 537713, 563181, 580355, 582931, 588228, 590654, 596577, 618193, 633000 and 530990-689986.

There is additionally provided in accordance with another preferred embodiment of the present invention a bioinformatically detectable first oligonucleotide which is a portion of a mRNA transcript of a target gene selected from the group consisting of genes shown in Table 11 row 20, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 8, 9 and 64411-78554.

There is moreover provided in accordance with another preferred embodiment of the present invention a bioinformatically detectable isolated oligonucleotide which anneals to a portion of a mRNA transcript of a target gene associated with Burkitt lymphoma, which target gene is selected from the group consisting of genes shown in Table 11, row 21, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5 and 78555-80110, and (b) the complement of a sequence selected from the group consisting of SEQ ID NOs: 690108, 692809, 693052 and 689987-693112.

There is further provided in accordance with another preferred embodiment of the present invention a bioinformatically detectable first oligonucleotide which is a portion of a mRNA transcript of a target gene selected from the group consisting of genes shown in Table 11 row 21, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5 and 78555-80110.

There is still further provided in accordance with another preferred embodiment of the present invention a bioinformatically detectable isolated oligonucleotide which anneals to a portion of a mRNA transcript of a target gene associated with Carcinoid, which target gene is selected from the group consisting of genes shown in Table 11, row 22, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 7 and 80111-80708, and (b) the complement of a sequence selected from the group consisting of SEQ ID NOs: 693404 and 693113-694254.

There is additionally provided in accordance with another preferred embodiment of the present invention a bioinformatically detectable first oligonucleotide which is a portion of a mRNA transcript of a target gene selected from the group consisting of genes shown in Table 11 row 22, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:7 and 80111-80708.

There is moreover provided in accordance with another preferred embodiment of the present invention a bioinformatically detectable isolated oligonucleotide which anneals to a portion of a mRNA transcript of a target gene associated with Cerebrovascular Accident, which target gene is selected from the group consisting of genes shown in Table 11, row 23, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5 and 80709-81325, and (b) the complement of a sequence selected from the group consisting of SEQ ID NOs: 694366, 695294 and 694255-695530.

There is further provided in accordance with another preferred embodiment of the present invention a bioinformatically detectable first oligonucleotide which is a portion of a mRNA transcript of a target gene selected from the group consisting of genes shown in Table 11 row 23, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5 and 80709-81325.

There is still further provided in accordance with another preferred embodiment of the present invention a bioinformatically detectable isolated oligonucleotide which anneals to a portion of a mRNA transcript of a target gene associated with Cervical cancer, which target gene is selected from the group consisting of genes shown in Table 11, row 24, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 7, 8 and 81326-86234, and (b) the complement of a sequence selected from the group consisting of SEQ ID NOs: 698866, 699633, 700140, 703176, 706969 and 695531-707027.

There is additionally provided in accordance with another preferred embodiment of the present invention a bioinformatically detectable first oligonucleotide which is a portion of a mRNA transcript of a target gene selected from the group consisting of genes shown in Table 11 row 24, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 7, 8 and 81326-86234.

There is moreover provided in accordance with another preferred embodiment of the present invention a bioinformatically detectable isolated oligonucleotide which anneals to a portion of a mRNA transcript of a target gene associated with Cholestasis, which target gene is selected from the group consisting of genes shown in Table 11, row 25, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2 and 86235-86695, and (b) the complement of a sequence selected from the group consisting of SEQ ID NOs: 707553 and 707028-707756.

There is further provided in accordance with another preferred embodiment of the present invention a bioinformatically detectable first oligonucleotide which is a portion of a mRNA transcript of a target gene selected from the group consisting of genes shown in Table 11 row 25, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2 and 86235-86695.

There is still further provided in accordance with another preferred embodiment of the present invention a bioinformatically detectable isolated oligonucleotide which anneals to a portion of a mRNA transcript of a target gene associated with Chronic obstructive pulmonary disease, which target gene is selected from the group consisting of genes shown in Table 11, row 26, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 9 and 86696-87220, and (b) the complement of a sequence selected from the group consisting of SEQ ID NOs: 708469 and 707757-708943.

There is additionally provided in accordance with another preferred embodiment of the present invention a bioinformatically detectable first oligonucleotide which is a portion of a mRNA transcript of a target gene selected from the group consisting of genes shown in Table 11 row 26, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:9 and 86696-87220.

There is moreover provided in accordance with another preferred embodiment of the present invention a bioinformatically detectable isolated oligonucleotide which anneals to a portion of a mRNA transcript of a target gene associated with Cirrhosis, which target gene is selected from the group consisting of genes shown in Table 11, row 27, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 8 and 87221-90071, and (b) the complement of a sequence selected from the group consisting of SEQ ID NOs: 712312, 714322, 714659 and 708944-715262.

There is further provided in accordance with another preferred embodiment of the present invention a bioinformatically detectable first oligonucleotide which is a portion of a mRNA transcript of a target gene selected from the group consisting of genes shown in Table 11 row 27, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 8 and 87221-90071.

There is still further provided in accordance with another preferred embodiment of the present invention a bioinformatically detectable isolated oligonucleotide which anneals to a portion of a mRNA transcript of a target gene associated with Colorectal cancer, which target gene is selected from the group consisting of genes shown in Table 11, row 28, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 8, 9 and 90072-103599, and (b) the complement of a sequence selected from the group consisting of SEQ ID NOs: 727396, 728779, 751651, 754078, 762029, 775468, 783181, 801412, 804645 and 715263-825119.

There is additionally provided in accordance with another preferred embodiment of the present invention a bioinformatically detectable first oligonucleotide which is a portion of a mRNA transcript of a target gene selected from the group consisting of genes shown in Table 11 row 28, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 8, 9 and 90072-103599.

There is moreover provided in accordance with another preferred embodiment of the present invention a bioinformatically detectable isolated oligonucleotide which anneals to a portion of a mRNA transcript of a target gene associated with Coronary artery disease, which target gene is selected from the group consisting of genes shown in Table 11, row 29, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5, 8 and 103600-104724, and (b) the complement of a sequence selected from the group consisting of SEQ ID NOs: 825764, 826087, 827311 and 825120-827584.

There is further provided in accordance with another preferred embodiment of the present invention a bioinformatically detectable first oligonucleotide which is a portion of a mRNA transcript of a target gene selected from the group consisting of genes shown in Table 11 row 29, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5, 8 and 103600-104724.

There is still further provided in accordance with another preferred embodiment of the present invention a bioinformatically detectable isolated oligonucleotide which anneals to a portion of a mRNA transcript of a target gene associated with Coronary disease, which target gene is selected from the group consisting of genes shown in Table 11, row 30, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5 and 104725-106952, and (b) the complement of a sequence selected from the group consisting of SEQ ID NOs: 828298, 828430, 830870 and 827585-832456.

There is additionally provided in accordance with another preferred embodiment of the present invention a bioinformatically detectable first oligonucleotide which is a portion of a mRNA transcript of a target gene selected from the group consisting of genes shown in Table 11 row 30, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5 and 104725-106952.

There is moreover provided in accordance with another preferred embodiment of the present invention a bioinformatically detectable isolated oligonucleotide which anneals to a portion of a mRNA transcript of a target gene associated with Crohn disease, which target gene is selected from the group consisting of genes shown in Table 11, row 31, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4, 9 and 106953-109974, and (b) the complement of a sequence selected from the group consisting of SEQ ID NOs: 834114, 834946, 835661, 837892 and 832457-839285.

There is further provided in accordance with another preferred embodiment of the present invention a bioinformatically detectable first oligonucleotide which is a portion of a mRNA transcript of a target gene selected from the group consisting of genes shown in Table 11 row 31, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4, 9 and 106953-109974.

There is still further provided in accordance with another preferred embodiment of the present invention a bioinformatically detectable isolated oligonucleotide which anneals to a portion of a mRNA transcript of a target gene associated with Cushing Syndrome, which target gene is selected from the group consisting of genes shown in Table 11, row 32, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3 and 109975-111300, and (b) the complement of a sequence selected from the group consisting of SEQ ID NOs: 840315 and 839286-842219.

There is additionally provided in accordance with another preferred embodiment of the present invention a bioinformatically detectable first oligonucleotide which is a portion of a mRNA transcript of a target gene selected from the group consisting of genes shown in Table 11 row 32, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3 and 109975-111300.

There is moreover provided in accordance with another preferred embodiment of the present invention a bioinformatically detectable isolated oligonucleotide which anneals to a portion of a mRNA transcript of a target gene associated with Cystic fibrosis, which target gene is selected from the group consisting of genes shown in Table 11, row 33, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 3, 7 and 111301-112941, and (b) the complement of a sequence selected from the group consisting of SEQ ID NOs: 842289, 843698, 844210 and 842220-845733.

There is further provided in accordance with another preferred embodiment of the present invention a bioinformatically detectable first oligonucleotide which is a portion of a mRNA transcript of a target gene selected from the group consisting of genes shown in Table 11 row 33, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 3, 7 and 111301-112941.

There is still further provided in accordance with another preferred embodiment of the present invention a bioinformatically detectable isolated oligonucleotide which anneals to a portion of a mRNA transcript of a target gene associated with Cytomegalovirus, which target gene is selected from the group consisting of genes shown in Table 11, row 34, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3 and 112942-113819, and (b) the complement of a sequence selected from the group consisting of SEQ ID NOs: 846249 and 845734-847315.

There is additionally provided in accordance with another preferred embodiment of the present invention a bioinformatically detectable first oligonucleotide which is a portion of a mRNA transcript of a target gene selected from the group consisting of genes shown in Table 11 row 34, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3 and 112942-113819.

There is moreover provided in accordance with another preferred embodiment of the present invention a bioinformatically detectable isolated oligonucleotide which anneals to a portion of a mRNA transcript of a target gene associated with Deafness, which target gene is selected from the group consisting of genes shown in Table 11, row 35, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5 and 113820-118195, and (b) the complement of a sequence selected from the group consisting of SEQ ID NOs: 848649, 852182, 852375, 853644, 855958 and 847316-857712.

There is further provided in accordance with another preferred embodiment of the present invention a bioinformatically detectable first oligonucleotide which is a portion of a mRNA transcript of a target gene selected from the group consisting of genes shown in Table 11 row 35, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5 and 113820-118195.

There is still further provided in accordance with another preferred embodiment of the present invention a bioinformatically detectable isolated oligonucleotide which anneals to a portion of a mRNA transcript of a target gene associated with Dementia, which target gene is selected from the group consisting of genes shown in Table 11, row 36, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 8 and 118196-121289, and (b) the complement of a sequence selected from the group consisting of SEQ ID NOs: 857749 and 857713-865105.

There is additionally provided in accordance with another preferred embodiment of the present invention a bioinformatically detectable first oligonucleotide which is a portion of a mRNA transcript of a target gene selected from the group consisting of genes shown in Table 11 row 36, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:8 and 118196-121289.

There is moreover provided in accordance with another preferred embodiment of the present invention a bioinformatically detectable isolated oligonucleotide which anneals to a portion of a mRNA transcript of a target gene associated with Depressive Disorder, which target gene is selected from the group consisting of genes shown in Table 11, row 37, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4, 9 and 121290-122885, and (b) the complement of a sequence selected from the group consisting of SEQ ID NOs: 865184, 865199, 865494, 868209 and 865106-868820.

There is further provided in accordance with another preferred embodiment of the present invention a bioinformatically detectable first oligonucleotide which is a portion of a mRNA transcript of a target gene selected from the group consisting of genes shown in Table 11 row 37, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4, 9 and 121290-122885.

There is still further provided in accordance with another preferred embodiment of the present invention a bioinformatically detectable isolated oligonucleotide which anneals to a portion of a mRNA transcript of a target gene associated with Diabetes Mellitus, which target gene is selected from the group consisting of genes shown in Table 11, row 38, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 8, 9 and 122886-133924, and (b) the complement of a sequence selected from the group consisting of SEQ ID NOs: 873495, 876489, 890935, 905639, 907865, 912792, 912900, 914377, 914914 and 868821-917960.

There is additionally provided in accordance with another preferred embodiment of the present invention a bioinformatically detectable first oligonucleotide which is a portion of a mRNA transcript of a target gene selected from the group consisting of genes shown in Table 11 row 38, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 8, 9 and 122886-133924.

There is moreover provided in accordance with another preferred embodiment of the present invention a bioinformatically detectable isolated oligonucleotide which anneals to a portion of a mRNA transcript of a target gene associated with Diabetic Neuropathies, which target gene is selected from the group consisting of genes shown in Table 11, row 39, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 9 and 133925-134125, and (b) the complement of a sequence selected from the group consisting of SEQ ID NOs: 918115 and 917961-918306.

There is further provided in accordance with another preferred embodiment of the present invention a bioinformatically detectable first oligonucleotide which is a portion of a mRNA transcript of a target gene selected from the group consisting of genes shown in Table 11 row 39, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:9 and 133925-134125.

There is still further provided in accordance with another preferred embodiment of the present invention a bioinformatically detectable isolated oligonucleotide which anneals to a portion of a mRNA transcript of a target gene associated with Down Syndrome, which target gene is selected from the group consisting of genes shown in Table 11, row 40, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 8, 9 and 134126-138186, and (b) the complement of a sequence selected from the group consisting of SEQ ID NOs: 918604, 918827, 923948, 924864, 928441, 928497 and 918307-929194.

There is additionally provided in accordance with another preferred embodiment of the present invention a bioinformatically detectable first oligonucleotide which is a portion of a mRNA transcript of a target gene selected from the group consisting of genes shown in Table 11 row 40, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 8, 9 and 134126-138186.

There is moreover provided in accordance with another preferred embodiment of the present invention a bioinformatically detectable isolated oligonucleotide which anneals to a portion of a mRNA transcript of a target gene associated with *E. coli*, which target gene is selected from the group consisting of genes shown in Table 11, row 41, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 7 and 138187-138875, and (b) the complement of a sequence selected from the group consisting of SEQ ID NOs: 930567 and 929195-930609.

There is further provided in accordance with another preferred embodiment of the present invention a bioinformatically detectable first oligonucleotide which is a portion of a mRNA transcript of a target gene selected from the group consisting of genes shown in Table 11 row 41, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:7 and 138187-138875.

There is still further provided in accordance with another preferred embodiment of the present invention a bioinformatically detectable isolated oligonucleotide which anneals to a portion of a mRNA transcript of a target gene associated with EBV, which target gene is selected from the group consisting of genes shown in Table 11, row 42, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4 and 138876-140216, and (b) the complement of a sequence selected from the group consisting of SEQ ID NOs: 930864, 930991 and 930610-932977.

There is additionally provided in accordance with another preferred embodiment of the present invention a bioinformatically detectable first oligonucleotide which is a portion of a mRNA transcript of a target gene selected from the group consisting of genes shown in Table 11 row 42, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4 and 138876-140216.

There is moreover provided in accordance with another preferred embodiment of the present invention a bioinformatically detectable isolated oligonucleotide which anneals to a portion of a mRNA transcript of a target gene associated with Encephalitis, which target gene is selected from the group consisting of genes shown in Table 11, row 43, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5 and 140217-141989, and (b) the complement of a sequence selected from the group consisting of SEQ ID NOs: 934591, 935231, 935922, 936660 and 932978-937142.

There is further provided in accordance with another preferred embodiment of the present invention a bioinformatically detectable first oligonucleotide which is a portion of a mRNA transcript of a target gene selected from the group consisting of genes shown in Table 11 row 43, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5 and 140217-141989.

There is still further provided in accordance with another preferred embodiment of the present invention a bioinformatically detectable isolated oligonucleotide which anneals to a portion of a mRNA transcript of a target gene associated with Endometrial carcinoma, which target gene is selected from the group consisting of genes shown in Table 11, row 44, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4, 5 and 141990-146429, and (b) the complement of a sequence selected from the group consisting of SEQ ID NOs: 937700, 945056, 945576 and 937143-947495.

There is additionally provided in accordance with another preferred embodiment of the present invention a bioinformatically detectable first oligonucleotide which is a portion of a mRNA transcript of a target gene selected from the group consisting of genes shown in Table 11 row 44, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4, 5 and 141990-146429.

There is moreover provided in accordance with another preferred embodiment of the present invention a bioinformatically detectable isolated oligonucleotide which anneals to a portion of a mRNA transcript of a target gene associated with Epilepsy, which target gene is selected from the group consisting of genes shown in Table 11, row 45, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 4, 6, 7, 8, 9 and 146430-150366, and (b) the complement of a sequence selected from the group consisting of SEQ ID NOs: 948495, 948823, 950041, 957222, 957491 and 947496-958361.

There is further provided in accordance with another preferred embodiment of the present invention a bioinformatically detectable first oligonucleotide which is a portion of a mRNA transcript of a target gene selected from the group consisting of genes shown in Table 11 row 45, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:4, 6, 7, 8, 9 and 146430-150366.

There is still further provided in accordance with another preferred embodiment of the present invention a bioinformatically detectable isolated oligonucleotide which anneals to a portion of a mRNA transcript of a target gene associated with Esophageal cancer, which target gene is selected from the group consisting of genes shown in Table 11, row 46, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5 and 150367-157081, and (b) the complement of a sequence selected from the group consisting of SEQ ID NOs: 965109, 965621, 967984 and 958362-977920.

There is additionally provided in accordance with another preferred embodiment of the present invention a bioinformatically detectable first oligonucleotide which is a portion of a mRNA transcript of a target gene selected from the group consisting of genes shown in Table 11 row 46, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5 and 150367-157081.

There is moreover provided in accordance with another preferred embodiment of the present invention a bioinformatically detectable isolated oligonucleotide which anneals to a portion of a mRNA transcript of a target gene associated with Gestational Diabetes, which target gene is selected from the group consisting of genes shown in Table 11, row 47, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 4 and 157082-157975, and (b) the complement of a sequence selected from the group consisting of SEQ ID NOs: 978234 and 977921-979856.

There is further provided in accordance with another preferred embodiment of the present invention a bioinformatically detectable first oligonucleotide which is a portion of a mRNA transcript of a target gene selected from the group consisting of genes shown in Table 11 row 47, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:4 and 157082-157975.

There is still further provided in accordance with another preferred embodiment of the present invention a bioinformatically detectable isolated oligonucleotide which anneals to a portion of a mRNA transcript of a target gene associated with Hemolytic anemia, which target gene is selected from the group consisting of genes shown in Table 11, row 48, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 5 and 157976-159408, and (b) the complement of a sequence selected from the group consisting of SEQ ID NOs: 980916 and 979857-982618.

There is additionally provided in accordance with another preferred embodiment of the present invention a bioinformatically detectable first oligonucleotide which is a portion of a mRNA transcript of a target gene selected from the group consisting of genes shown in Table 11 row 48, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:5 and 157976-159408.

There is moreover provided in accordance with another preferred embodiment of the present invention a bioinformatically detectable isolated oligonucleotide which anneals to a portion of a mRNA transcript of a target gene associated with Hepatitis, which target gene is selected from the group consisting of genes shown in Table 11, row 49, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4 and 159409-162998, and (b) the complement of a sequence selected from the group consisting of SEQ ID NOs: 982753, 987503, 989853 and 982619-990063.

There is further provided in accordance with another preferred embodiment of the present invention a bioinformatically detectable first oligonucleotide which is a portion of a mRNA transcript of a target gene selected from the group consisting of genes shown in Table 11 row 49, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4 and 159409-162998.

There is still further provided in accordance with another preferred embodiment of the present invention a bioinformatically detectable isolated oligonucleotide which anneals to a portion of a mRNA transcript of a target gene associated with Hepatocellular carcinoma, which target gene is selected from the group consisting of genes shown in Table 11, row 50, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5, 6, 8, 9 and 162999-169899, and (b) the complement of a sequence selected from the group consisting of SEQ ID NOs: 993716, 993916, 1005318, 1007352, 1007621, 1009512 and 990064-1010372.

There is additionally provided in accordance with another preferred embodiment of the present invention a bioinformatically detectable first oligonucleotide which is a portion of a mRNA transcript of a target gene selected from the group consisting of genes shown in Table 11 row 50, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5, 6, 8, 9 and 162999-169899.

There is moreover provided in accordance with another preferred embodiment of the present invention a bioinformatically detectable isolated oligonucleotide which anneals to a portion of a mRNA transcript of a target gene associated with Herpes, which target gene is selected from the group consisting of genes shown in Table 11, row 51, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5 and 169900-170780, and (b) the complement of a sequence selected from the group consisting of SEQ ID NOs: 1010547, 1011819 and 1010373-1012009.

There is further provided in accordance with another preferred embodiment of the present invention a bioinformatically detectable first oligonucleotide which is a portion of a mRNA transcript of a target gene selected from the group consisting of genes shown in Table 11 row 51, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5 and 169900-170780.

There is still further provided in accordance with another preferred embodiment of the present invention a bioinformatically detectable isolated oligonucleotide which anneals to a portion of a mRNA transcript of a target gene associated with HIV, which target gene is selected from the group consisting of genes shown in Table 11, row 52, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 6, 7, 8, 9 and 170781-182163, and (b) the complement of a sequence selected from the group consisting of SEQ ID NOs: 1016403, 1020340, 1021892, 1025469, 1034095, 1036559, 1039213, 1059225 and 1012010-1066060.

There is additionally provided in accordance with another preferred embodiment of the present invention a bioinformatically detectable first oligonucleotide which is a portion of a mRNA transcript of a target gene selected from the group consisting of genes shown in Table 11 row 52, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 6, 7, 8, 9 and 170781-182163.

There is moreover provided in accordance with another preferred embodiment of the present invention a bioinformatically detectable isolated oligonucleotide which anneals to a portion of a mRNA transcript of a target gene associated with Hodgkin Disease, which target gene is selected from the group consisting of genes shown in Table 11, row 53, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 4, 7 and 182164-184872, and (b) the complement of a sequence selected from the group consisting of SEQ ID NOs: 1070393, 1070600 and 1066061-1072255.

There is further provided in accordance with another preferred embodiment of the present invention a bioinformatically detectable first oligonucleotide which is a portion of a mRNA transcript of a target gene selected from the group consisting of genes shown in Table 11 row 53, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:4, 7 and 182164-184872.

There is still further provided in accordance with another preferred embodiment of the present invention a bioinformatically detectable isolated oligonucleotide which anneals to a portion of a mRNA transcript of a target gene associated with HTLV, which target gene is selected from the group consisting of genes shown in Table 11, row 54, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3 and 184873-185735, and (b) the complement of a sequence selected from the group consisting of SEQ ID NOs: 1073162 and 1072256-1073988.

There is additionally provided in accordance with another preferred embodiment of the present invention a bioinformatically detectable first oligonucleotide which is a portion of a mRNA transcript of a target gene selected from the group consisting of genes shown in Table 11 row 54, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3 and 184873-185735.

There is moreover provided in accordance with another preferred embodiment of the present invention a bioinformatically detectable isolated oligonucleotide which anneals to a portion of a mRNA transcript of a target gene associated with Hypercholesterolemia, which target gene is selected from the group consisting of genes shown in Table 11, row 55, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 6, 9 and 185736-187896, and (b) the complement of a sequence selected from the group consisting of SEQ ID NOs: 1074582, 1074720, 1075037, 1075126, 1075843, 1078670 and 1073989-1078934.

There is further provided in accordance with another preferred embodiment of the present invention a bioinformatically detectable first oligonucleotide which is a portion of a mRNA transcript of a target gene selected from the group consisting of genes shown in Table 11 row 55, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 6, 9 and 185736-187896.

There is still further provided in accordance with another preferred embodiment of the present invention a bioinformatically detectable isolated oligonucleotide which anneals to a portion of a mRNA transcript of a target gene associated with Hyperlipidemia, which target gene is selected from the group consisting of genes shown in Table 11, row 56, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 6 and 187897-188796, and (b) the complement of a sequence selected from the group consisting of SEQ ID NOs: 1080228 and 1078935-1080845.

There is additionally provided in accordance with another preferred embodiment of the present invention a bioinformatically detectable first oligonucleotide which is a portion of a mRNA transcript of a target gene selected from the group consisting of genes shown in Table 11 row 56, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:6 and 187897-188796.

There is moreover provided in accordance with another preferred embodiment of the present invention a bioinformatically detectable isolated oligonucleotide which anneals to a portion of a mRNA transcript of a target gene associated with Hypertension, which target gene is selected from the group consisting of genes shown in Table 11, row 57, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 6 and 188797-192961, and (b) the complement of a sequence selected from the group consisting of SEQ ID NOs: 1085210, 1085664, 1087844, 1089045, 1089716 and 1080846-1091130.

There is further provided in accordance with another preferred embodiment of the present invention a bioinformatically detectable first oligonucleotide which is a portion of a mRNA transcript of a target gene selected from the group consisting of genes shown in Table 11 row 57, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 6 and 188797-192961.

There is still further provided in accordance with another preferred embodiment of the present invention a bioinformatically detectable isolated oligonucleotide which anneals to a portion of a mRNA transcript of a target gene associated with Hypertrophic cardiomyopathy, which target gene is selected from the group consisting of genes shown in Table 11, row 58, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 8 and 192962-193617, and (b) the complement of a sequence selected from the group consisting of SEQ ID NOs: 1091710, 1091785 and 1091131-1092040.

There is additionally provided in accordance with another preferred embodiment of the present invention a bioinformatically detectable first oligonucleotide which is a portion of a mRNA transcript of a target gene selected from the group consisting of genes shown in Table 11 row 58, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 8 and 192962-193617.

There is moreover provided in accordance with another preferred embodiment of the present invention a bioinformatically detectable isolated oligonucleotide which anneals to a portion of a mRNA transcript of a target gene associated with Infertility, which target gene is selected from the group consisting of genes shown in Table 11, row 59, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4 and 193618-195919, and (b) the complement of a sequence selected from the group consisting of SEQ ID NOs: 1092671, 1093478, 1093837, 1095824 and 1092041-1096852.

There is further provided in accordance with another preferred embodiment of the present invention a bioinformatically detectable first oligonucleotide which is a portion of a mRNA transcript of a target gene selected from the group consisting of genes shown in Table 11 row 59, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4 and 193618-195919.

There is still further provided in accordance with another preferred embodiment of the present invention a bioinformatically detectable isolated oligonucleotide which anneals to a portion of a mRNA transcript of a target gene associated with Insulin-Dependent Diabetes Mellitus, which target gene is selected from the group consisting of genes shown in Table 11, row 60, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 8, 9 and 195920-203885, and (b) the complement of a sequence selected from the group consisting of SEQ ID NOs: 1099174, 1100156, 1102360, 1104859, 1106580, 1108401, 1109682, 1111400, 1116325 and 1096853-1121723.

There is additionally provided in accordance with another preferred embodiment of the present invention a bioinformatically detectable first oligonucleotide which is a portion of a mRNA transcript of a target gene selected from the group consisting of genes shown in Table 11 row 60, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 8, 9 and 195920-203885.

There is moreover provided in accordance with another preferred embodiment of the present invention a bioinformatically detectable isolated oligonucleotide which anneals to a portion of a mRNA transcript of a target gene associated with Intestinal Neoplasms, which target gene is selected from the group consisting of genes shown in Table 11, row 61, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3, 8 and 203886-206003, and (b) the complement of a sequence selected from the group consisting of SEQ ID NOs: 1123085, 1126105 and 1121724-1126428.

There is further provided in accordance with another preferred embodiment of the present invention a bioinformatically detectable first oligonucleotide which is a portion of a mRNA transcript of a target gene selected from the group consisting of genes shown in Table 11 row 61, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3, 8 and 203886-206003.

There is still further provided in accordance with another preferred embodiment of the present invention a bioinformatically detectable isolated oligonucleotide which anneals to a portion of a mRNA transcript of a target gene associated with Kidney Failure, which target gene is selected from the group consisting of genes shown in Table 11, row 62, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 3, 4, 8 and 206004-207959, and (b) the complement of a sequence selected from the group consisting of SEQ ID NOs: 1127252, 1128714, 1130019, 1130111 and 1126429-1130552.

There is additionally provided in accordance with another preferred embodiment of the present invention a bioinformatically detectable first oligonucleotide which is a portion of a mRNA transcript of a target gene selected from the group consisting of genes shown in Table 11 row 62, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 3, 4, 8 and 206004-207959.

There is moreover provided in accordance with another preferred embodiment of the present invention a bioinformatically detectable isolated oligonucleotide which anneals to a portion of a mRNA transcript of a target gene associated with Leukemia, which target gene is selected from the group consisting of genes shown in Table 11, row 63, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 8, 9 and 207960-219782, and (b) the complement of a sequence selected from the group consisting of SEQ ID NOs: 1139319, 1143895, 1148321, 1152010, 1167196, 1176875, 1179489, 1188269, 1190430 and 1130553-1192133.

There is further provided in accordance with another preferred embodiment of the present invention a bioinformatically detectable first oligonucleotide which is a portion of a mRNA transcript of a target gene selected from the group consisting of genes shown in Table 11 row 63, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 8, 9 and 207960-219782.

There is still further provided in accordance with another preferred embodiment of the present invention a bioinformatically detectable isolated oligonucleotide which anneals to a portion of a mRNA transcript of a target gene associated with Lung cancer, which target gene is selected from the group consisting of genes shown in Table 11, row 64, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 8, 9 and 219783-233017, and (b) the complement of a sequence selected from the group consisting of SEQ ID NOs: 1192848, 1206194, 1212204, 1231034, 1237185, 1254223, 1265270, 1275904, 1278916 and 1192134-1281827.

There is additionally provided in accordance with another preferred embodiment of the present invention a bioinformatically detectable first oligonucleotide which is a portion of a mRNA transcript of a target gene selected from the group consisting of genes shown in Table 11 row 64, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 8, 9 and 219783-233017.

There is moreover provided in accordance with another preferred embodiment of the present invention a bioinformatically detectable isolated oligonucleotide which anneals to a portion of a mRNA transcript of a target gene associated with Lupus Erythematosus, which target gene is selected from the group consisting of genes shown in Table 11, row 65, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5 and 233018-236892, and (b) the complement of a sequence selected from the group consisting of SEQ ID NOs: 1282550, 1286608, 1289906 and 1281828-1290763.

There is further provided in accordance with another preferred embodiment of the present invention a bioinformatically detectable first oligonucleotide which is a portion of a mRNA transcript of a target gene selected from the group consisting of genes shown in Table 11 row 65, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5 and 233018-236892.

There is still further provided in accordance with another preferred embodiment of the present invention a bioinformatically detectable isolated oligonucleotide which anneals to a portion of a mRNA transcript of a target gene associated with Lymphoma, which target gene is selected from the group consisting of genes shown in Table 11, row 66, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 8, 9 and 236893-245820, and (b) the complement of a sequence selected from the group consisting of SEQ ID NOs: 1294513, 1296922, 1299883, 1305370, 1307574, 1310857, 1313187 and 1290764-1323487.

There is additionally provided in accordance with another preferred embodiment of the present invention a bioinformatically detectable first oligonucleotide which is a portion of a mRNA transcript of a target gene selected from the group consisting of genes shown in Table 11 row 66, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 8, 9 and 236893-245820.

There is moreover provided in accordance with another preferred embodiment of the present invention a bioinformatically detectable isolated oligonucleotide which anneals to a portion of a mRNA transcript of a target gene associated with Megaloblastic anemia, which target gene is selected from the group consisting of genes shown in Table 11, row 67, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3 and 245821-246395, and (b) the complement of a sequence selected from the group consisting of SEQ ID NOs: 1323625 and 1323488-1324618.

There is further provided in accordance with another preferred embodiment of the present invention a bioinformatically detectable first oligonucleotide which is a portion of a mRNA transcript of a target gene selected from the group consisting of genes shown in Table 11 row 67, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3 and 245821-246395.

There is still further provided in accordance with another preferred embodiment of the present invention a bioinformatically detectable isolated oligonucleotide which anneals to a portion of a mRNA transcript of a target gene associated with Melanoma, which target gene is selected from the group consisting of genes shown in Table 11, row 68, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 8, 9 and 246396-255510, and (b) the complement of a sequence selected from the group consisting of SEQ ID NOs: 1325755, 1329827, 1344554, 1344822, 1346246, 1347255, 1350673 and 1324619-1355010.

There is additionally provided in accordance with another preferred embodiment of the present invention a bioinformatically detectable first oligonucleotide which is a portion of a mRNA transcript of a target gene selected from the group consisting of genes shown in Table 11 row 68, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 8, 9 and 246396-255510.

There is moreover provided in accordance with another preferred embodiment of the present invention a bioinformatically detectable isolated oligonucleotide which anneals to a portion of a mRNA transcript of a target gene associated with Multiple Myeloma, which target gene is selected from the group consisting of genes shown in Table 11, row 69, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 7, 9 and 255511-260801, and (b) the complement of a sequence selected from the group consisting of SEQ ID NOs: 1356299, 1357626, 1358102, 1359792, 1363307, 1364428 and 1355011-1369725.

There is further provided in accordance with another preferred embodiment of the present invention a bioinformatically detectable first oligonucleotide which is a portion of a mRNA transcript of a target gene selected from the group consisting of genes shown in Table 11 row 69, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 7, 9 and 255511-260801.

There is still further provided in accordance with another preferred embodiment of the present invention a bioinformatically detectable isolated oligonucleotide which anneals to a portion of a mRNA transcript of a target gene associated with Multiple Sclerosis, which target gene is selected from the group consisting of genes shown in Table 11, row 70, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 6, 7 and 260802-270006, and (b) the complement of a sequence selected from the group consisting of SEQ ID NOs: 1373644, 1376311, 1380037, 1386570, 1401556, 1402175 and 1369726-1402294.

There is additionally provided in accordance with another preferred embodiment of the present invention a bioinformatically detectable first oligonucleotide which is a portion of a mRNA transcript of a target gene selected from the group consisting of genes shown in Table 11 row 70, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 6, 7 and 260802-270006.

There is moreover provided in accordance with another preferred embodiment of the present invention a bioinformatically detectable isolated oligonucleotide which anneals to a portion of a mRNA transcript of a target gene associated with *Mycoplasma*, which target gene is selected from the group consisting of genes shown in Table 11, row 71, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 7 and 270007-270127, and (b) the complement of a sequence selected from the group consisting of SEQ ID NOs: 1402440 and 1402295-1402560.

There is further provided in accordance with another preferred embodiment of the present invention a bioinformatically detectable first oligonucleotide which is a portion of a mRNA transcript of a target gene selected from the group consisting of genes shown in Table 11 row 71, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:7 and 270007-270127.

There is still further provided in accordance with another preferred embodiment of the present invention a bioinformatically detectable isolated oligonucleotide which anneals to a portion of a mRNA transcript of a target gene associated with Myocardial Infarction, which target gene is selected from the group consisting of genes shown in Table 11, row 72, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5, 9 and 270128-273123, and (b) the complement of a sequence selected from the group consisting of SEQ ID NOs: 1402767, 1404818, 1409126 and 1402561-1409743.

There is additionally provided in accordance with another preferred embodiment of the present invention a bioinformatically detectable first oligonucleotide which is a portion of a mRNA transcript of a target gene selected from the group consisting of genes shown in Table 11 row 72, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5, 9 and 270128-273123.

There is moreover provided in accordance with another preferred embodiment of the present invention a bioinformatically detectable isolated oligonucleotide which anneals to a portion of a mRNA transcript of a target gene associated with Myopathy, which target gene is selected from the group consisting of genes shown in Table 11, row 73, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 3, 4, 5, 8 and 273124-277208, and (b) the complement of a sequence selected from the group consisting of SEQ ID NOs: 1411884, 1415279, 1416040, 1416101, 1416399 and 1409744-1418387.

There is further provided in accordance with another preferred embodiment of the present invention a bioinformatically detectable first oligonucleotide which is a portion of a mRNA transcript of a target gene selected from the group consisting of genes shown in Table 11 row 73, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 3, 4, 5, 8 and 273124-277208.

There is still further provided in accordance with another preferred embodiment of the present invention a bioinformatically detectable isolated oligonucleotide which anneals to a portion of a mRNA transcript of a target gene associated with Non-Insulin-Dependent Diabetes Mellitus, which target gene is selected from the group consisting of genes shown in Table 11, row 74, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 7, 9 and 277209-286107, and (b) the complement of a sequence selected from the group consisting of SEQ ID NOs: 1422612, 1428492, 1429976, 1431402, 1437363, 1441110, 1444472 and 1418388-1449420.

There is additionally provided in accordance with another preferred embodiment of the present invention a bioinformatically detectable first oligonucleotide which is a portion of a mRNA transcript of a target gene selected from the group consisting of genes shown in Table 11 row 74, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 7, 9 and 277209-286107.

There is moreover provided in accordance with another preferred embodiment of the present invention a bioinformatically detectable isolated oligonucleotide which anneals to a portion of a mRNA transcript of a target gene associated with Nonsmall cell lung cancer, which target gene is selected from the group consisting of genes shown in Table 11, row 75, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 7, 8, 9 and 286108-297453, and (b) the complement of a sequence selected from the group consisting of SEQ ID NOs: 1449455, 1462227, 1466142, 1479753, 1481270, 1492650, 1501017 and 1449421-1503474.

There is further provided in accordance with another preferred embodiment of the present invention a bioinformatically detectable first oligonucleotide which is a portion of a mRNA transcript of a target gene selected from the group consisting of genes shown in Table 11 row 75, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 7, 8, 9 and 286108-297453.

There is still further provided in accordance with another preferred embodiment of the present invention a bioinformatically detectable isolated oligonucleotide which anneals to a portion of a mRNA transcript of a target gene associated with Obesity, which target gene is selected from the group consisting of genes shown in Table 11, row 76, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 8 and 297454-302887, and (b) the complement of a sequence selected from the group consisting of SEQ ID NOs: 1504767, 1511905, 1512173, 1513271, 1513396, 1515436, 1516295 and 1503475-1518557.

There is additionally provided in accordance with another preferred embodiment of the present invention a bioinformatically detectable first oligonucleotide which is a portion of a mRNA transcript of a target gene selected from the group consisting of genes shown in Table 11 row 76, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 8 and 297454-302887.

There is moreover provided in accordance with another preferred embodiment of the present invention a bioinformatically detectable isolated oligonucleotide which anneals to a portion of a mRNA transcript of a target gene associated with Osteoarthritis, which target gene is selected from the group consisting of genes shown in Table 11, row 77, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5, 7 and 302888-304404, and (b) the complement of a sequence selected from the group consisting of SEQ ID NOs: 1520245, 1520246, 1521185 and 1518558-1521862.

There is further provided in accordance with another preferred embodiment of the present invention a bioinformatically detectable first oligonucleotide which is a portion of a mRNA transcript of a target gene selected from the group consisting of genes shown in Table 11 row 77, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5, 7 and 302888-304404.

There is still further provided in accordance with another preferred embodiment of the present invention a bioinformatically detectable isolated oligonucleotide which anneals to a portion of a mRNA transcript of a target gene associated with Osteoporosis, which target gene is selected from the group consisting of genes shown in Table 11, row 78, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2 and 304405-306066, and (b) the complement of a sequence selected from the group consisting of SEQ ID NOs: 1524207, 1525522 and 1521863-1525625.

There is additionally provided in accordance with another preferred embodiment of the present invention a bioinformatically detectable first oligonucleotide which is a portion of a mRNA transcript of a target gene selected from the group consisting of genes shown in Table 11 row 78, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2 and 304405-306066.

There is moreover provided in accordance with another preferred embodiment of the present invention a bioinformatically detectable isolated oligonucleotide which anneals to a portion of a mRNA transcript of a target gene associated with Ovarian cancer, which target gene is selected from the group consisting of genes shown in Table 11, row 79, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3, 4 and 306067-306673, and (b) the complement of a sequence selected from the group consisting of SEQ ID NOs: 1525926, 1526754 and 1525626-1526881.

There is further provided in accordance with another preferred embodiment of the present invention a bioinformatically detectable first oligonucleotide which is a portion of a mRNA transcript of a target gene selected from the group consisting of genes shown in Table 11 row 79, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3, 4 and 306067-306673.

There is still further provided in accordance with another preferred embodiment of the present invention a bioinformatically detectable isolated oligonucleotide which anneals to a portion of a mRNA transcript of a target gene associated with Pagets Disease, which target gene is selected from the group consisting of genes shown in Table 11, row 80, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5 and 306674-307098, and (b) the complement of a sequence selected from the group consisting of SEQ ID NOs: 1527098, 1527099 and 1526882-1527691.

There is additionally provided in accordance with another preferred embodiment of the present invention a bioinformatically detectable first oligonucleotide which is a portion of a mRNA transcript of a target gene selected from the group consisting of genes shown in Table 11 row 80, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5 and 306674-307098.

There is moreover provided in accordance with another preferred embodiment of the present invention a bioinformatically detectable isolated oligonucleotide which anneals to a portion of a mRNA transcript of a target gene associated with Pancreatic cancer, which target gene is selected from the group consisting of genes shown in Table 11, row 81, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4 and 307099-308722, and (b) the complement of a sequence selected from the group consisting of SEQ ID NOs: 1529097, 1529673 and 1527692-1531107.

There is further provided in accordance with another preferred embodiment of the present invention a bioinformatically detectable first oligonucleotide which is a portion of a mRNA transcript of a target gene selected from the group consisting of genes shown in Table 11 row 81, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4 and 307099-308722.

There is still further provided in accordance with another preferred embodiment of the present invention a bioinformatically detectable isolated oligonucleotide which anneals to a portion of a mRNA transcript of a target gene associated with Pancreatitis, which target gene is selected from the group consisting of genes shown in Table 11, row 82, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4 and 308723-310671, and (b) the complement of a sequence selected from the group consisting of SEQ ID NOs: 1533367, 1533459, 1533900 and 1531108-1534150.

There is additionally provided in accordance with another preferred embodiment of the present invention a bioinformatically detectable first oligonucleotide which is a portion of a mRNA transcript of a target gene selected from the group consisting of genes shown in Table 11 row 82, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4 and 308723-310671.

There is moreover provided in accordance with another preferred embodiment of the present invention a bioinformatically detectable isolated oligonucleotide which anneals to a portion of a mRNA transcript of a target gene associated with Parkinson, which target gene is selected from the group consisting of genes shown in Table 11, row 83, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4, 5, 8 and 310672-315566, and (b) the complement of a sequence selected from the group consisting of SEQ ID NOs: 1538745, 1540648, 1542324, 1543008 and 1534151-1546112.

There is further provided in accordance with another preferred embodiment of the present invention a bioinformatically detectable first oligonucleotide which is a portion of a mRNA transcript of a target gene selected from the group consisting of genes shown in Table 11 row 83, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4, 5, 8 and 310672-315566.

There is still further provided in accordance with another preferred embodiment of the present invention a bioinformatically detectable isolated oligonucleotide which anneals to a portion of a mRNA transcript of a target gene associated with Pituitary tumor, which target gene is selected from the group consisting of genes shown in Table 11, row 84, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 4 and 315567-318091, and (b) the complement of a sequence selected from the group consisting of SEQ ID NOs: 1548490 and 1546113-1551863.

There is additionally provided in accordance with another preferred embodiment of the present invention a bioinformatically detectable first oligonucleotide which is a portion of a mRNA transcript of a target gene selected from the group consisting of genes shown in Table 11 row 84, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:4 and 315567-318091.

There is moreover provided in accordance with another preferred embodiment of the present invention a bioinformatically detectable isolated oligonucleotide which anneals to a portion of a mRNA transcript of a target gene associated with Polyposis coli, which target gene is selected from the group consisting of genes shown in Table 11, row 85, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1 and 318092-319885, and (b) the complement of a sequence selected from the group consisting of SEQ ID NOs: 1552495 and 1551864-1555475.

There is further provided in accordance with another preferred embodiment of the present invention a bioinformatically detectable first oligonucleotide which is a portion of a mRNA transcript of a target gene selected from the group consisting of genes shown in Table 11 row 85, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1 and 318092-319885.

There is still further provided in accordance with another preferred embodiment of the present invention a bioinformatically detectable isolated oligonucleotide which anneals to a portion of a mRNA transcript of a target gene associated with Prostate cancer, which target gene is selected from the group consisting of genes shown in Table 11, row 86, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 8, 9 and 319886-331776, and (b) the complement of a sequence selected from the group consisting of SEQ ID NOs: 1560176, 1567745, 1567746, 1570725, 1572754, 1585351, 1586318, 1590104, 1601618 and 1555476-1616125.

There is additionally provided in accordance with another preferred embodiment of the present invention a bioinformatically detectable first oligonucleotide which is a portion of a mRNA transcript of a target gene selected from the group consisting of genes shown in Table 11 row 86, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 8, 9 and 319886-331776.

There is moreover provided in accordance with another preferred embodiment of the present invention a bioinformatically detectable isolated oligonucleotide which anneals to a portion of a mRNA transcript of a target gene associated with Renal cell carcinoma, which target gene is selected from the group consisting of genes shown in Table 11, row 87, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4, 5, 6, 8, 9 and 331777-339379, and (b) the complement of a sequence selected from the group consisting of SEQ ID NOs: 1623084, 1624645, 1630149, 1631365, 1632279, 1632601, 1634960 and 1616126-1638267.

There is further provided in accordance with another preferred embodiment of the present invention a bioinformatically detectable first oligonucleotide which is a portion of a mRNA transcript of a target gene selected from the group consisting of genes shown in Table 11 row 87, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4, 5, 6, 8, 9 and 331777-339379.

There is still further provided in accordance with another preferred embodiment of the present invention a bioinformatically detectable isolated oligonucleotide which anneals to a portion of a mRNA transcript of a target gene associated with Rheumatoid arthritis, which target gene is selected from the group consisting of genes shown in Table 11, row 88, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 7, 8 and 339380-345777, and (b) the complement of a sequence selected from the group consisting of SEQ ID NOs: 1647854, 1648450, 1652438, 1652821, 1654347, 1655395 and 1638268-1656864.

There is additionally provided in accordance with another preferred embodiment of the present invention a bioinformatically detectable first oligonucleotide which is a portion of a mRNA transcript of a target gene selected from the group consisting of genes shown in Table 11 row 88, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 7, 8 and 339380-345777.

There is moreover provided in accordance with another preferred embodiment of the present invention a bioinformatically detectable isolated oligonucleotide which anneals to a portion of a mRNA transcript of a target gene associated with Schizophrenia, which target gene is selected from the group consisting of genes shown in Table 11, row 89, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 6, 7, 9 and 345778-353664, and (b) the complement of a sequence selected from the group consisting of SEQ ID NOs: 1661647, 1664279, 1666399, 1671735, 1676144, 1676419, 1677821 and 1656865-1680643.

There is further provided in accordance with another preferred embodiment of the present invention a bioinformatically detectable first oligonucleotide which is a portion of a mRNA transcript of a target gene selected from the group consisting of genes shown in Table 11 row 89, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 6, 7, 9 and 345778-353664.

There is still further provided in accordance with another preferred embodiment of the present invention a bioinformatically detectable isolated oligonucleotide which anneals to a portion of a mRNA transcript of a target gene associated with Sickle cell anemia, which target gene is selected from the group consisting of genes shown in Table 11, row 90, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1 and 353665-353965, and (b) the complement of a sequence selected from the group consisting of SEQ ID NOs: 1680710 and 1680644-1681178.

There is additionally provided in accordance with another preferred embodiment of the present invention a bioinformatically detectable first oligonucleotide which is a portion of a mRNA transcript of a target gene selected from the group consisting of genes shown in Table 11 row 90, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1 and 353665-353965.

There is moreover provided in accordance with another preferred embodiment of the present invention a bioinformatically detectable isolated oligonucleotide which anneals to a portion of a mRNA transcript of a target gene associated with Skin Neoplasms, which target gene is selected from the group consisting of genes shown in Table 11, row 91, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5, 8 and 353966-357211, and (b) the complement of a sequence selected from the group consisting of SEQ ID NOs: 1682122, 1682809, 1685015, 1688065, 1688674 and 1681179-1689188.

There is further provided in accordance with another preferred embodiment of the present invention a bioinformatically detectable first oligonucleotide which is a portion of a mRNA transcript of a target gene selected from the group consisting of genes shown in Table 11 row 91, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5, 8 and 353966-357211.

There is still further provided in accordance with another preferred embodiment of the present invention a bioinformatically detectable isolated oligonucleotide which anneals to a portion of a mRNA transcript of a target gene associated with Small cell carcinoma, which target gene is selected from the group consisting of genes shown in Table 11, row 92, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 3, 4, 5, 6, 7, 8, 9 and 357212-366028, and (b) the complement of a sequence selected from the group consisting of SEQ ID NOs: 1691592, 1695929, 1698522, 1704710, 1711184, 1712841, 1713491, 1713961 and 1689189-1718935.

There is additionally provided in accordance with another preferred embodiment of the present invention a bioinformatically detectable first oligonucleotide which is a portion of a mRNA transcript of a target gene selected from the group consisting of genes shown in Table 11 row 92, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 3, 4, 5, 6, 7, 8, 9 and 357212-366028.

There is moreover provided in accordance with another preferred embodiment of the present invention a bioinformatically detectable isolated oligonucleotide which anneals to a portion of a mRNA transcript of a target gene associated with Stroke, which target gene is selected from the group consisting of genes shown in Table 11, row 93, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 9 and 366029-366240, and (b) the complement of a sequence selected from the group consisting of SEQ ID NOs: 1719291 and 1718936-1719322.

There is further provided in accordance with another preferred embodiment of the present invention a bioinformatically detectable first oligonucleotide which is a portion of a mRNA transcript of a target gene selected from the group consisting of genes shown in Table 11 row 93, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:9 and 366029-366240.

There is still further provided in accordance with another preferred embodiment of the present invention a bioinformatically detectable isolated oligonucleotide which anneals to a portion of a mRNA transcript of a target gene associated with Thrombocytopenia, which target gene is selected from the group consisting of genes shown in Table 11, row 94, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 5 and 366241-367479, and (b) the complement of a sequence selected from the group consisting of SEQ ID NOs: 1720002, 1720143 and 1719323-1721893.

There is additionally provided in accordance with another preferred embodiment of the present invention a bioinformatically detectable first oligonucleotide which is a portion of a mRNA transcript of a target gene selected from the group consisting of genes shown in Table 11 row 94, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 5 and 366241-367479.

There is moreover provided in accordance with another preferred embodiment of the present invention a bioinformatically detectable isolated oligonucleotide which anneals to a portion of a mRNA transcript of a target gene associated with Thrombosis, which target gene is selected from the group consisting of genes shown in Table 11, row 95, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3 and 367480-368957, and (b) the complement of a sequence selected from the group consisting of SEQ ID NOs: 1722618 and 1721894-1724998.

There is further provided in accordance with another preferred embodiment of the present invention a bioinformatically detectable first oligonucleotide which is a portion of a mRNA transcript of a target gene selected from the group consisting of genes shown in Table 11 row 95, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3 and 367480-368957.

There is still further provided in accordance with another preferred embodiment of the present invention a bioinformatically detectable isolated oligonucleotide which anneals to a portion of a mRNA transcript of a target gene associated with Thyroid carcinoma, which target gene is selected from the group consisting of genes shown in Table 11, row 96, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4 and 368958-370099, and (b) the complement of a sequence selected from the group consisting of SEQ ID NOs: 1726360, 1727668 and 1724999-1727777.

There is additionally provided in accordance with another preferred embodiment of the present invention a bioinformatically detectable first oligonucleotide which is a portion of a mRNA transcript of a target gene selected from the group consisting of genes shown in Table 11 row 96, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4 and 368958-370099.

There is moreover provided in accordance with another preferred embodiment of the present invention a bioinformatically detectable isolated oligonucleotide which anneals to a portion of a mRNA transcript of a target gene associated with Thyroiditis, which target gene is selected from the group consisting of genes shown in Table 11, row 97, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 3, 9 and 370100-371570, and (b) the complement of a sequence selected from the group consisting of SEQ ID NOs: 1728962, 1729375 and 1727778-1730405.

There is further provided in accordance with another preferred embodiment of the present invention a bioinformatically detectable first oligonucleotide which is a portion of a mRNA transcript of a target gene selected from the group consisting of genes shown in Table 11 row 97, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:3, 9 and 370100-371570.

There is still further provided in accordance with another preferred embodiment of the present invention a bioinformatically detectable isolated oligonucleotide which anneals to a portion of a mRNA transcript of a target gene associated with Transitional cell carcinoma, which target gene is selected from the group consisting of genes shown in Table 11, row 98, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1 and 371571-372890, and (b) the complement of a sequence selected from the group consisting of SEQ ID NOs: 1732939 and 1730406-1733000.

There is additionally provided in accordance with another preferred embodiment of the present invention a bioinformatically detectable first oligonucleotide which is a portion of a mRNA transcript of a target gene selected from the group consisting of genes shown in Table 11 row 98, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1 and 371571-372890.

There is moreover provided in accordance with another preferred embodiment of the present invention a bioinformatically detectable isolated oligonucleotide which anneals to a portion of a mRNA transcript of a target gene associated with Tuberculosis, which target gene is selected from the group consisting of genes shown in Table 11, row 99, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 3, 4, 5 and 372891-373841, and (b) the complement of a sequence selected from the group consisting of SEQ ID NOs: 1733202, 1733678, 1733814, 1734089, 1734449 and 1733001-1734692.

There is further provided in accordance with another preferred embodiment of the present invention a bioinformatically detectable first oligonucleotide which is a portion of a mRNA transcript of a target gene selected from the group consisting of genes shown in Table 11 row 99, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 3, 4, 5 and 372891-373841.

There is still further provided in accordance with another preferred embodiment of the present invention a bioinformatically detectable isolated oligonucleotide which anneals to a portion of a mRNA transcript of a target gene associated with Turner Syndrome, which target gene is selected from the group consisting of genes shown in Table 11, row 100, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2 and 373842-373977, and (b) the complement of a sequence selected from the group consisting of SEQ ID NOs: 1734716 and 1734693-1734755.

There is additionally provided in accordance with another preferred embodiment of the present invention a bioinformatically detectable first oligonucleotide which is a portion of a mRNA transcript of a target gene selected from the group consisting of genes shown in Table 11 row 100, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2 and 373842-373977.

There is moreover provided in accordance with another preferred embodiment of the present invention a bioinformatically detectable isolated oligonucleotide which anneals to a portion of a mRNA transcript of a target gene associated with Ulcerative colitis, which target gene is selected from the group consisting of genes shown in Table 11, row 101, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 1, 2, 4 and 373978-376540, and (b) the complement of a sequence selected from the group consisting of SEQ ID NOs: 1735019, 1735846, 1736563 and 1734756-1739752.

There is further provided in accordance with another preferred embodiment of the present invention a bioinformatically detectable first oligonucleotide which is a portion of a mRNA transcript of a target gene selected from the group consisting of genes shown in Table 11 row 101, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:1, 2, 4 and 373978-376540.

There is still further provided in accordance with another preferred embodiment of the present invention a bioinformatically detectable isolated oligonucleotide which anneals to a portion of a mRNA transcript of a target gene associated with Urinary calculi, which target gene is selected from the group consisting of genes shown in Table 11, row 102, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4 and 376541-376853, and (b) the complement of a sequence selected from the group consisting of SEQ ID NOs: 1739998, 1740265 and 1739753-1740424.

There is additionally provided in accordance with another preferred embodiment of the present invention a bioinformatically detectable first oligonucleotide which is a portion of a mRNA transcript of a target gene selected from the group consisting of genes shown in Table 11 row 102, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4 and 376541-376853.

There is moreover provided in accordance with another preferred embodiment of the present invention a bioinformatically detectable isolated oligonucleotide which anneals to a portion of a mRNA transcript of a target gene associated with Ventricular tachycardia, which target gene is selected from the group consisting of genes shown in Table 11, row 103, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 7, 9 and 376854-377741, and (b) the complement of a sequence selected from the group consisting of SEQ ID NOs: 1740600, 1740700, 1741971 and 1740425-1742188.

There is further provided in accordance with another preferred embodiment of the present invention a bioinformatically detectable first oligonucleotide which is a portion of a mRNA transcript of a target gene selected from the group consisting of genes shown in Table 11 row 103, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 7, 9 and 376854-377741.

There is still further provided in accordance with another preferred embodiment of the present invention a bioinformatically detectable isolated oligonucleotide which anneals to a portion of a mRNA transcript of a target gene associated with Virus Diseases, which target gene is selected from the group consisting of genes shown in Table 11, row 104, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOs: 2, 4, 5 and 377742-377921, and (b) the complement of a sequence selected from the group consisting of SEQ ID NOs: 1742226, 1742388 and 1742189-1742399.

There is additionally provided in accordance with another preferred embodiment of the present invention a bioinformatically detectable first oligonucleotide which is a portion of a mRNA transcript of a target gene selected from the group consisting of genes shown in Table 11 row 104, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs:2, 4, 5 and 377742-377921.

There is moreover provided in accordance with another preferred embodiment of the present invention a method for bioinformatic detection of microRNA oligonucleotides, the method including: bioinformatically detecting a hairpin shaped precursor oligonucleotide, bioinformatically detecting an oligonucleotide which is endogenously processed from the hairpin shaped precursor oligonucleotide, and bioinformatically detecting a target gene of the oligonucleotide wherein the oligonucleotide anneals to at least one portion of a mRNA transcript of the target gene, and wherein the binding represses expression of the target gene, and the target gene is associated with a disease.

BRIEF DESCRIPTION OF DRAWINGS

FIGS. 5A and 5B are schematic diagrams, which when taken together, illustrate a 'genomic records' concept of the conceptual model of the present invention, addressing the genomic differentiation enigma;

FIGS. 20A and 20B are simplified diagrams, which when taken together illustrate a mode of oligonucleotide therapy applicable to novel oligonucleotides of the present invention;

FIG. 21B is a table summarizing laboratory validation results which validate efficacy of a bioinformatic oligonucleotide detection system constructed and operative in accordance with a preferred embodiment of the present invention;

FIG. 22A and FIG. 22B are a picture and a summary table of laboratory results validating the expression of novel human oligonucleotides detected by a bioinformatic oligonucleotide detection engine constructed and operative in accordance with a preferred embodiment of the present invention, thereby validating the efficacy of the oligonucleotide detection engine of the present invention;

FIG. 24A is an annotated sequence of EST72223 (SEQ ID NO: 225462) comprising known human mRNA oligonucleotide MIR98 and novel human oligonucleotide CAM25 PRECURSOR detected by the oligonucleotide detection system of the present invention. The sequence of EST72223 includes the four marked sequences: the sequence of the miRNA-98 hairpin in bold (SEQ ID NO: 2254589), the sequence of the mature miRNA-98 in bold and underlined (SEQ ID NO: 2254590), the sequence of the GAM25 hairpin in bold (SEQ ID NO: 2254591) and the sequence of the mature miRNA of GAM25 in bold and underlined (SEQ ID NO: 2254592); and FIGS. 24B, 24C and 24D are pictures of laboratory results demonstrating laboratory confirmation of expression of known human oligonucleotide MIR98 and of novel bioinformatically detected human GAM25 RNA respectively, both of FIG. 24A, thus validating the bioinformatic oligonucleotide detection system of the present invention;

BRIEF DESCRIPTION OF SEQUENCES

A Sequence Listing of genomic sequences of the present invention designated SEQ ID NO:1 through SEQ ID: 2254510 is attached to this application, and is hereby incorporated herein. The genomic listing comprises the following nucleotide sequences: nucleotide sequences of 15454 GAM precursors of respective novel oligonucleotides of the present invention; nucleotide sequences of 14676 GAM RNA oligonucleotides of respective novel oligonucleotides of the present invention; and nucleotide sequences of 496883 target gene binding sites of respective novel oligonucleotides of the present invention.

DETAILED DESCRIPTION

Figure 1:
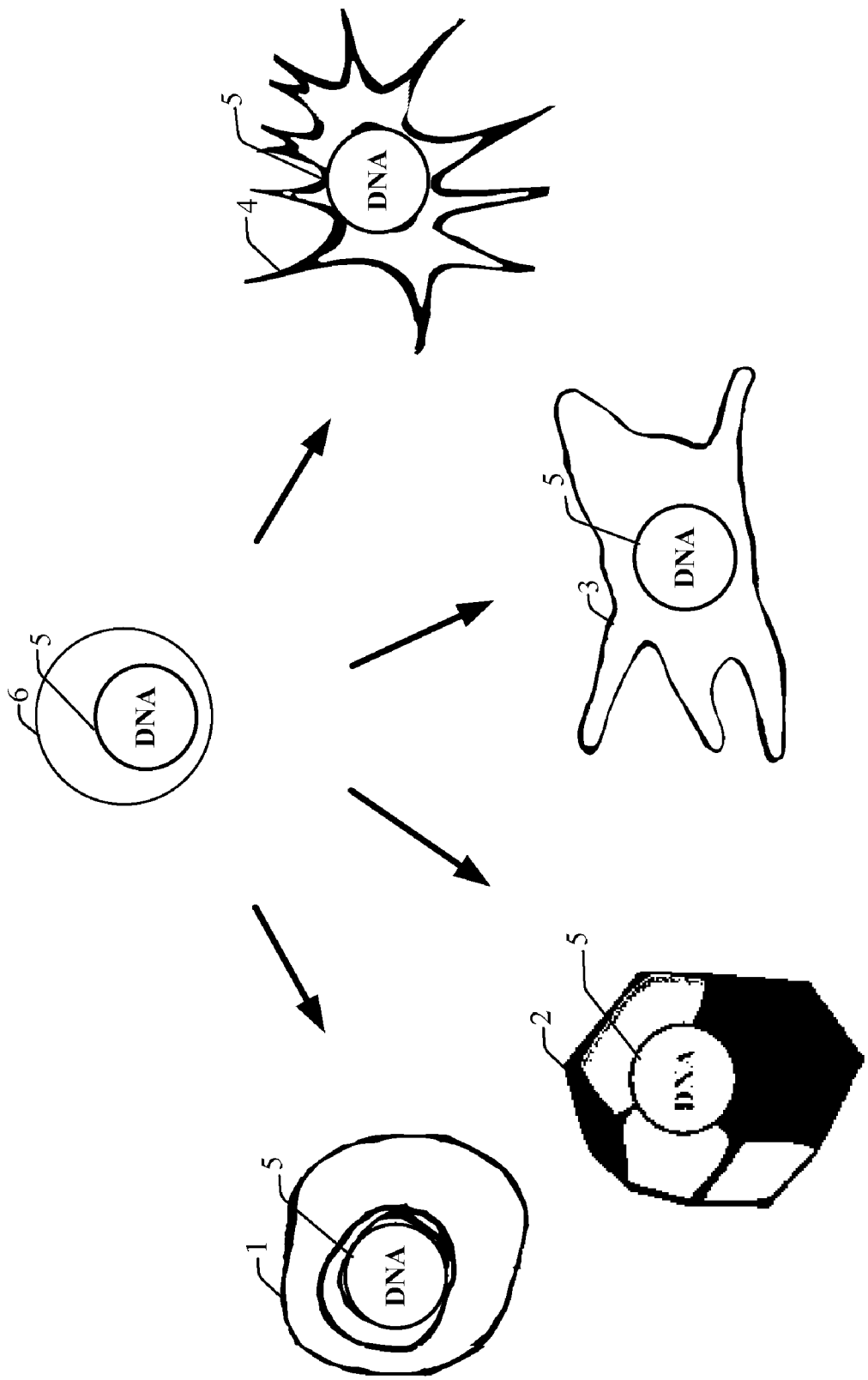
FIG. 1 is a simplified diagram illustrating a genomic differentiation enigma that the present invention addresses.

Reference is now made to FIG. 1 which is a simplified diagram providing a conceptual explanation of a genomic differentiation enigma, which the present invention addresses, inter alia.

FIG. 1 depicts various types of cells in an organism, such as a cartilage cell designated by reference numeral 1, a liver cell designated by reference numeral 2, a fibroblast cell designated by reference numeral 3, and a bone cell designated by reference numeral 4, all containing identical DNA designated by reference numeral 5. Notwithstanding that the various types of cells are all derived from an initial fertilized egg cell designated by reference numeral 6, each of these cells expresses different proteins and accordingly acquire a different shape and function.

The present invention proposes inter alia that the inevitable conclusion from the foregoing is, however, strikingly simple: the genome must contain a modular differentiation coding system. The genome of each cell must include multiple modules or records, possibly a different one for each cell type, as well as a mechanism causing each cell at its inception to be instructed which one of the multiple records governs its behavior.

This modular code concept may be somewhat difficult to grasp, since most persons are accustomed to view things from an external viewpoint. An architect, for example, looks at a plan of a building, which details exactly where each element (block, window, door, electrical switch, etc.) is to be placed relative to all other elements, and, using the plan, instructs builders to place these elements in their designated places. This is an example of an external viewpoint: the architect is external to the plan, which itself is external with respect to the physical building, and with respect to its various elements. The architect may therefore act as an "external organizing agent": seeing the full picture and the relationships between all elements, and being able to instruct from the outside where to place each of them.

According to a preferred embodiment of the present invention, genomic differentiation coding works differently, without any such external organizing agent. It comprises a smart block (the first cell), which is the architect and the plan, and which continuously duplicates itself, somehow knowing when to manifest itself as a block and when as a window, door, or electrical switch.

Reference is now made to FIGS. 2A-4 which are schematic diagrams which, when taken together, provide an analogy that illustrates a conceptual model of the present invention, addressing the genomic differentiation enigma.

Reference is now made to FIG. 2A. An imaginary talented chef, designated by reference numeral 7, is capable of preparing any meal provided that he is given specific written cooking instructions. This chef 7 is equipped with two items: (a) a thick recipe book, designated by reference numeral 8, and (b) a small note, designated by reference numeral 9, having a number scribbled on it. The recipe book 8 comprises multiple pages, each page detailing how to prepare a specific meal. The small note 9 indicates the page to be opened, and therefore the meal to be prepared. The chef looks at the page number written on the note, opens the recipe book to the appropriate page, and prepares the meal according to the written instructions on this page. In the example shown in FIG. 2A, the chef 7 is holding a small note 9 bearing the number 127. He therefore opens the book to page 127, as designated by reference numeral 10. Since this page contains the recipe for preparing bread, the chef 7 prepares a loaf of bread, designated by reference numeral 12. Pages of the book, such as page 10 in the example shown in FIG. 2A, contain additional information, designated by reference numeral 11 which additional data is further elaborated hereinbelow with reference to FIGS. 3 and 4.

Figure 2B:
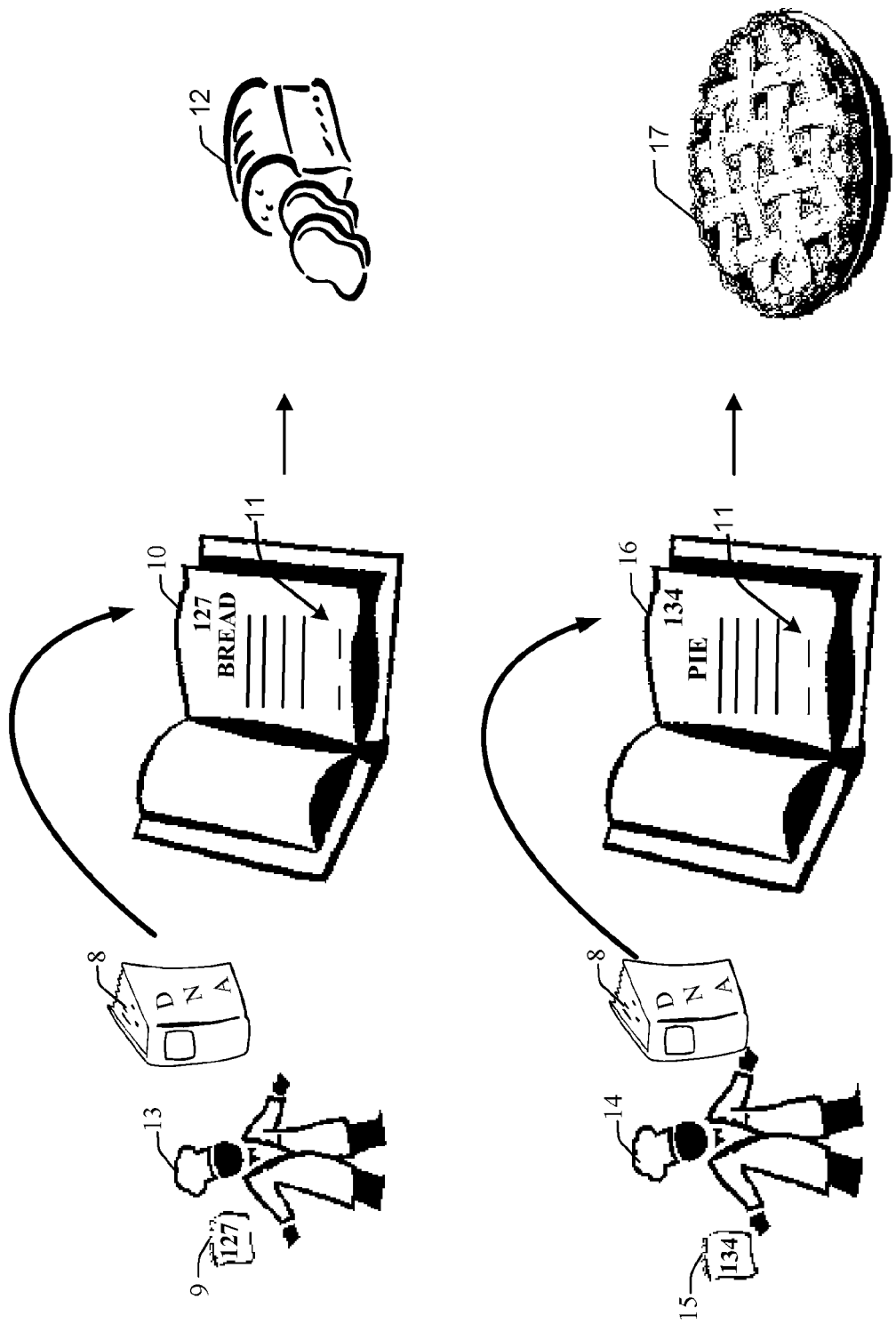
FIGS. 2, 3 and 4 are schematic diagrams which, when taken together, provide an analogy that illustrates a conceptual model of the present invention, addressing the genomic differentiation enigma.

Reference is now made to FIG. 2B, which depicts two identical chefs, a first chef, designated by reference numeral 13, and a second chef, designated by reference numeral 14, both holding an identical recipe book, designated by reference numeral 8. Although the first chef 13 and the second chef 14 are identical, and hold identical recipe books 8, they differ in that they hold different small notes: the first chef 13 holds a small note designated by reference numeral 9, having the number 127 written on it, whereas the second chef 14 holds a small note designated by reference numeral 15, having the number 134 written on it. Accordingly, the first chef 13 opens the book 8 to page 127, as designated by reference numeral 10 and, based on the instructions written on page 127 prepares a loaf of bread, designated by reference numeral 12. The second chef 14 opens the book 8 to page 134, as designated by reference numeral 16 and, based on the instructions written on page 134, prepares a pie, designated by reference numeral 17. Pages in the book, such as pages 10 and 16 in the examples shown in FIG. 2B, contain additional information, designated by reference numeral 11 which additional information is further elaborated hereinbelow with reference to FIGS. 3 and 4.

Figure 3:
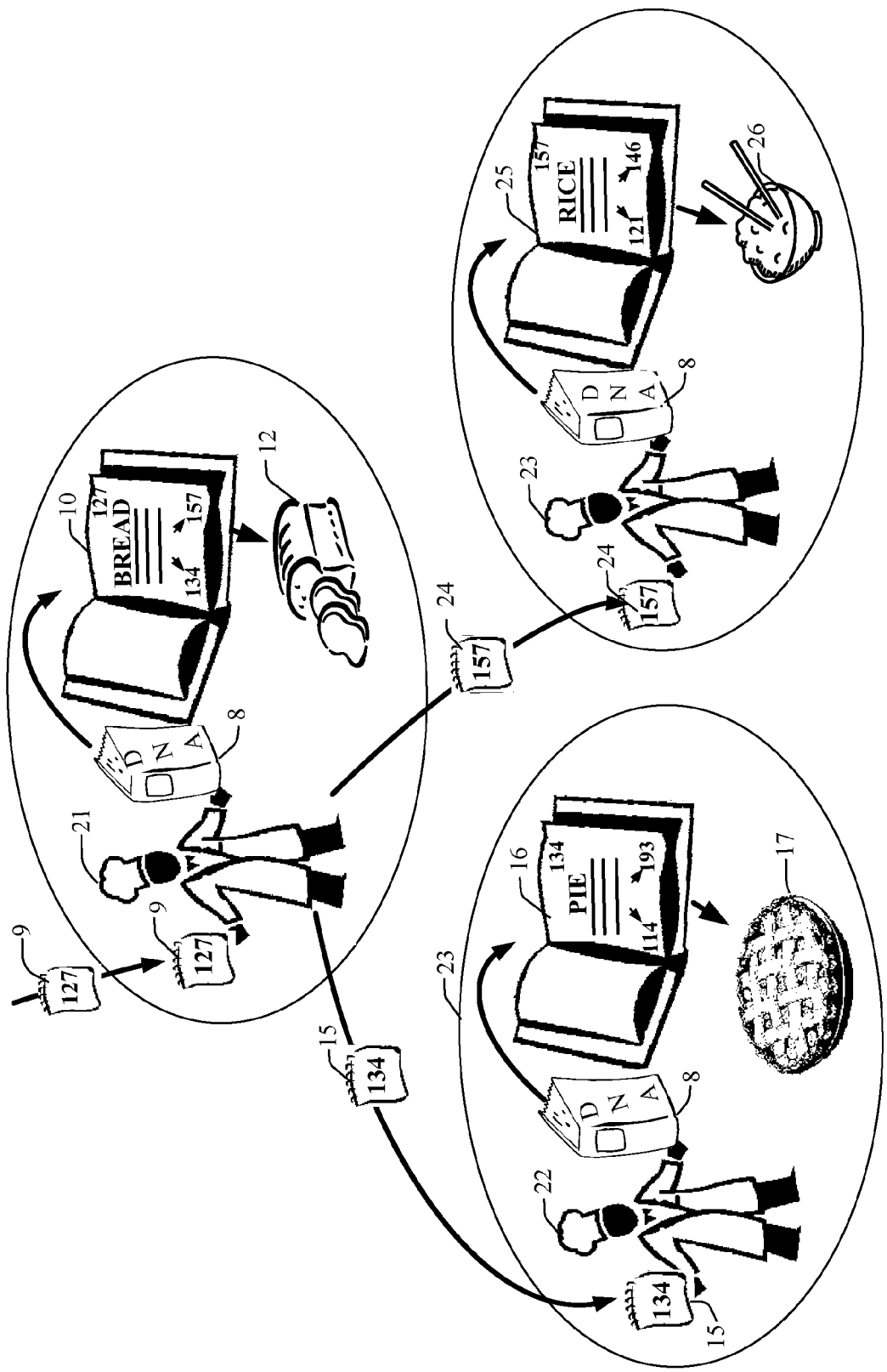

Reference is now made to FIG. 3 which illustrates a mode by which an imaginary chef can duplicate himself yielding two identical chefs, instructing each of the identical duplicate chefs to prepare a different meal. As an example, FIG. 3 shows chef 21 duplicating himself, yielding two duplicate chefs: a first duplicate chef designated by reference numeral 22 and a second duplicate chef designated by reference numeral 23. The duplicate chefs are identical to each other and to chef 21.

Like chefs 7 and 13 (FIGS. 2A and 2B), FIG. 3 shows chef 21 holding a recipe book 8 and receiving a note 9 bearing the number 127. The chef 21 therefore opens the book 8 to page 127, as designated by reference numeral 10, and prepares a loaf of bread 12. However, FIG. 3 also elaborates some of the additional information 11 (FIGS. 2A and 2B) found in page 10: the bottom of page 10, bears two numbers, 134 and 157.

Chef 21 is trained to perform the following three actions when he is finished preparing a meal: (a) Duplicate himself yielding two duplicate chefs, the first duplicate chef 22 and the second duplicate chef 23; (b) Duplicate his recipe book 8, handing an identical copy to each of the duplicate chefs 22 and 23; and (c) Write down the numbers found at the bottom of the page he was instructed to open the book to. In the example of chef 21, since he was instructed to open the book to page 10, he writes the numbers 134 and 157 on two respective notes designated by reference numerals 15 and 24, and hands note 15 bearing the number 134 to the first duplicate chef 22 and note 24 bearing the number 157 to the second duplicate chef 23.

Accordingly, the first duplicate chef 22 receives note 15 bearing the number 134 and therefore opens the recipe book 8 to page 134, as designated by reference numeral 16, and prepares a pie, designated by reference numeral 17. The second duplicate chef 23 receives note 24 bearing the number 157 and therefore opens the recipe book 8 to page 157, as designated by reference numeral 25, and prepares rice, designated by reference numeral 26.

It is appreciated that while chef 21 and duplicate chefs 22 and 23 are identical and hold identical recipe books 8, they each prepare a different meal. It is also appreciated that the meals prepared by the first duplicate chef 22 and the second duplicate chef 23 are determined by chef 21, and are mediated by the differently numbered notes 15 and 24 passed on from chef 21 to duplicate chefs 22 and 23 respectively.

It is further appreciated that the mechanism illustrated by FIG. 3 enables an unlimited lineage of chefs to divide into duplicate, identical chefs and to determine the meals those duplicate chefs would prepare. As an example, since the first duplicate chef 22 is directed to page 134, as designated by reference numeral 16, when he duplicates himself (not shown), he will instruct his two duplicate chefs to prepare meals specified on pages the numbers of which are written at the bottom of page 134, i.e. pages 114 and 193 respectively. Similarly, the second duplicate chef 23 will instruct its duplicate chefs to prepare meals specified on pages 121 and 146 respectively, etc.

Figure 4:
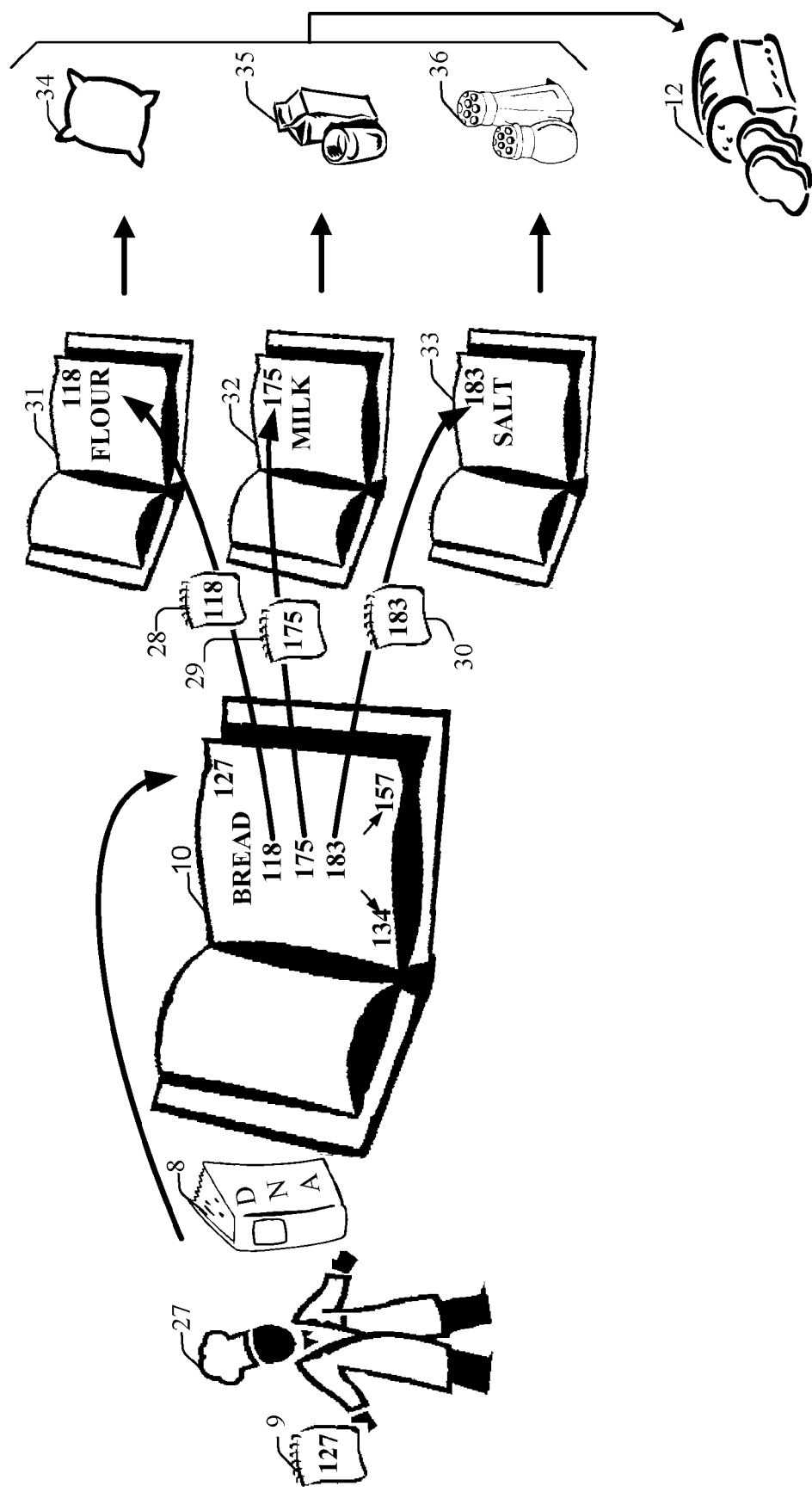

Reference is now made to FIG. 4, which illustrates a mode by which a chef can prepare a meal based on instructions written in a shorthand format: The main meal-page to which a chef is directed by a small note he is given, merely contains a list of numbers which further direct him to other pages, each specifying how to prepare an ingredient of that meal.

To illustrate this shorthand format FIG. 4 shows a chef, designated by reference numeral 27, holding the recipe book 8 and the note 9 which bears the number 127. The chef 27 accordingly opens the recipe book 8 to page 127, as designated by reference numeral 10, and based on instructions on this page prepares bread 12. This is similar to chefs 7, 13 and 21 of FIGS. 2A, 2B and 3 respectively.

However, FIG. 4 also further elaborates some of the additional information 11 (FIGS. 2A and 2B) found in page 10. FIG. 4 shows the cooking "instructions" found on page 10 for making bread 12 written in a shorthand format, comprising only three numbers, 118, 175 and 183. The chef 27 writes these numbers on three respective notes designated by reference numerals 28-30. The notes 28-30 are then used to turn to corresponding pages 31-33 of the book 8, which pages provide instructions for preparation of ingredients required for making bread 12: flour 34, milk 35 and salt 36.

The analogy provided by FIGS. 2A-4 illustrates the conceptual model of the present invention addressing the genomic differentiation enigma, and may be explained as follows: The chefs and duplicate chefs 7, 13, 14, 21-23 and 27 (FIGS. 2A-4) in the given analogy represent cells. The thick recipe book 8 represents the DNA 5 (FIG. 1). Preparing meals such as bread 12, pie 17 or rice 26 (all of FIG. 3) represent the cell manifesting itself as a specific cell-type, such as cartilage cell 1, liver cell 2, fibroblast cell 3, and bone cell 4 (all of FIG. 1). Ingredients of a meal, such as flour 34, milk 35 and salt 36 (all of FIG. 4), represent proteins typically expressed by a cell of a certain cell-type, such as 1-4. Like the different chefs of the analogy, having the same thick recipe book 8 yet preparing different meals, so do different cells in an organism contain the same DNA 5 yet manifest themselves as different cell types, such as 1-4, expressing proteins typical of these respective cell types. Application of analogy of FIGS. 2A-4 to cell-biology is further described hereinbelow with reference to FIGS. 5A-7.

Figure 5A:
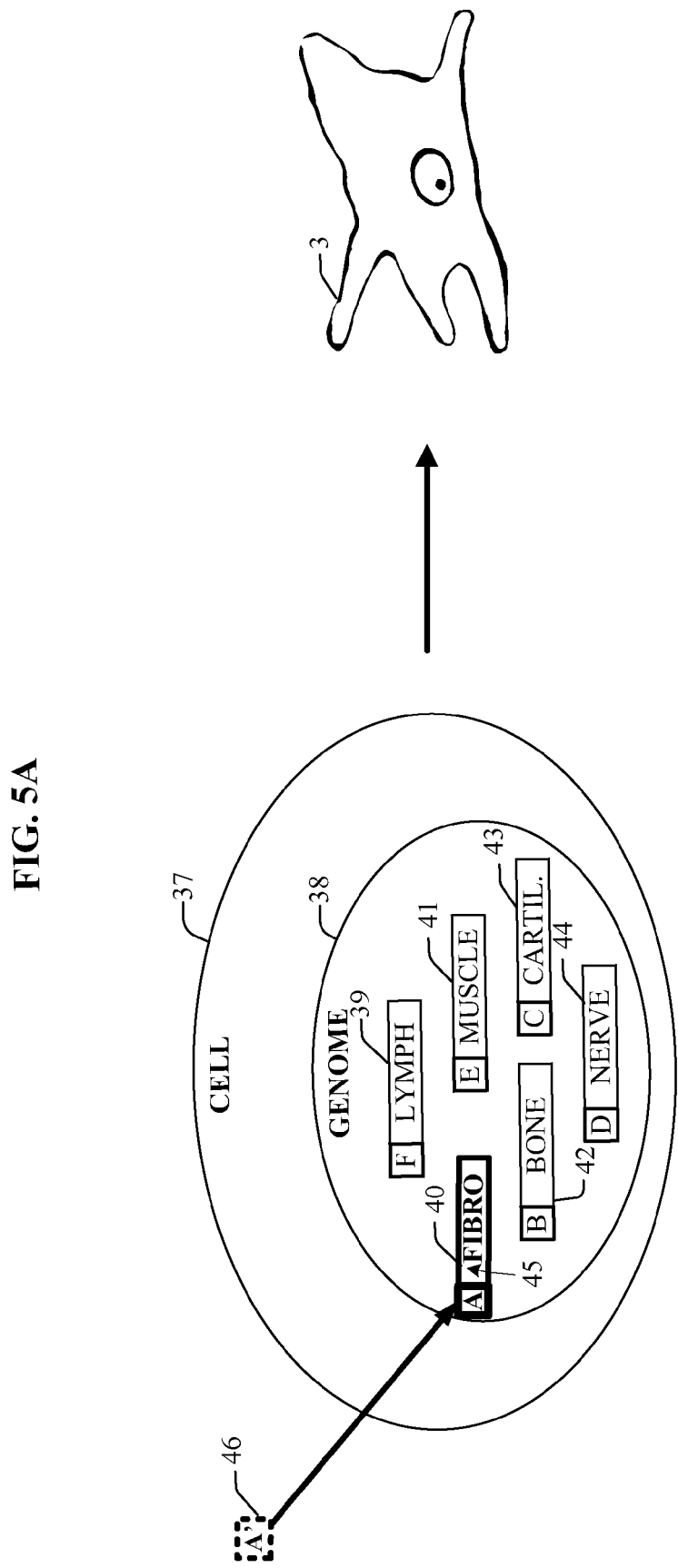

Reference is now made to FIGS. 5A and 5B which are schematic diagrams, which when taken together illustrate a Genomic Records concept of the present invention, addressing the genomic differentiation enigma. FIGS. 5A and 5B correspond to FIGS. 2A and 2B of the chef analogy described hereinabove.

An important aspect of the present invention is the Genomic Records concept. According to a preferred embodiment of the present invention the DNA (the thick recipe book 8 in the illustration) comprises a very large number of Genomic Records (analogous to pages, such as 10, 16 and 25, in the recipe book) containing the instructions for differentiation of a different cell-type, or developmental process. Each Genomic Record comprises a very short genomic sequence which functions as a "Genomic Address" of that Genomic Record (analogous to a page number, such as the numbers 127, 134 and 157 appearing in FIG. 3, in the recipe book). At its inception, in addition to the DNA, each cell also receives a short RNA segment (the scribbled short note, such as 9, 15, 24 of FIG. 3 in the illustration). This short RNA segment binds complementarily to a "Genomic Address" sequence of one of the Genomic Records, thereby modulating expression of that Genomic Record, and accordingly determining the cell's-fate (analogous to opening the recipe book 8 to a page corresponding to a number on the scribbled note, thereby determining the meal to be prepared). A Genomic Record may also comprise multiple short RNA segments each of which binds complementarily to a target protein coding gene, thus modulating expression of this target gene (analogous to the shorthand format whereby a page, such as 10, points to other pages, such as 31-33, encoding various ingredient, such as 34, 35 and 36, all of FIG. 4).

Reference is now made to FIG. 5A. FIG. 5A illustrates a cell 37, having a genome 38. The genome 38 comprises a plurality of Genomic Records, some of which Genomic Records correlate to specific cell-types. As an example, 6 such genomic records are shown, corresponding to 6 cell-types: LYMPH genomic record 39, FIBROBLAST genomic record 40, MUSCLE genomic record 41, BONE genomic record 42, CARTILAGE genomic record 43 and NERVE genomic record 44. Each genomic record comprises genomic instructions on differentiation into a specific cell-type, as further elaborated hereinbelow with reference to FIG. 7. At cell inception, the cell 37 receives a maternal short RNA segment 46, which activates one of the genomic records, causing the cell to differentiate according to the instructions this genomic record comprises. As an example FIG. 5A illustrates reception of a maternal short RNA segment designated 46 having a nucleotide sequence herein symbolically represented by A'.

The FIBROBLAST genomic record 40 contains a binding site having a nucleotide sequence symbolically represented by A, which is complementary to the nucleotide sequence of A', and therefore the short RNA segment 46 binds to the FIBROBLAST genomic record 40. This binding activates the FIBROBLAST genomic record, causing the cell 37 to differentiate into a fibroblast cell-type 3 (FIG. 1). Other genomic records, designated by reference numerals 39 and 41-44, comprise binding sites having nucleotide sequences that are symbolically represented by F, E, B, C and D, which are not complementary of the nucleotide sequence of the short RNA segment 46, and are therefore not activated thereby. Genomic Records, such as the FIBROBLAST genomic record 40 contain additional information, designated by reference numeral 45, which is further elaborated hereinbelow with reference to FIGS. 6 and 7.

Reference is now made to FIG. 5B, which is a simplified schematic diagram, illustrating cellular differentiation mediated by the "Genomic Records" concept. FIG. 5B depicts 2 cells in an organism, CELL A designated by reference numeral 47 and CELL B designated by reference numeral 48, each having a genome 38. It is appreciated that since CELL A 47 and CELL B 48 are cells in the same organism, the genome 38 of cells 47 and 48 is identical. Despite having an identical genome 38, CELL A 47 differentiates differently from CELL B 48, due to activation of different genomic records in these two cells. In CELL A 47 the FIBRO GENOMIC RECORD 40 is activated, causing CELL A 47 to differentiate into a FIBROBLAST CELL 3, whereas in CELL B 48 the BONE GENOMIC RECORD 42 is activated, causing the CELL B 48 to differentiate into a BONE CELL 4 (FIG. 1). The cause for activation of different genomic records in these two cells is the different maternal short RNA which they both received: CELL A 47 received a maternal short RNA segment designated 46 bearing a nucleotide sequence represented by A' activating genomic record FIBRO 40, whereas CELL B 48 received a maternal short RNA segment designated 49 bearing a nucleotide sequence represented by B' activating genomic record BONE 42.

Figure 6:
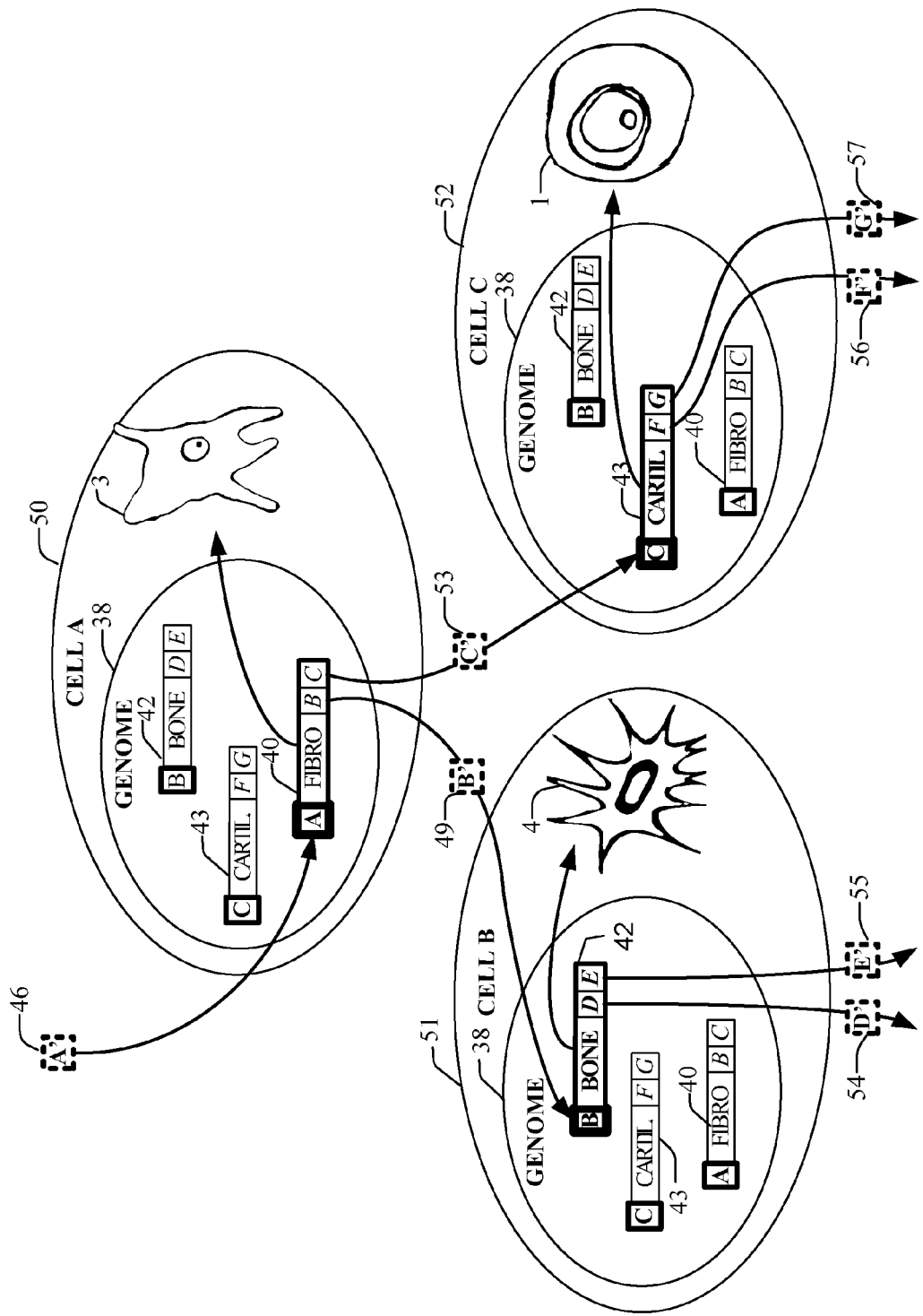
FIG. 6 is a schematic diagram illustrating a 'genomically programmed cell differentiation' concept of the conceptual model of the present invention, addressing the genomic differentiation enigma.

Reference is now made to FIG. 6 which is a schematic diagram illustrating a "genomically programmed cell differentiation" concept of the conceptual model of the present invention, addressing the genomic differentiation enigma.

A cell designated CELL A 50 divides into 2 cells designated CELL B 51 and CELL C 52. CELL A 50, CELL B 51 and CELL C 52, each comprises a GENOME 38. GENOME 38 comprises a plurality of GENOMIC RECORDS, herein exemplified by reference numerals 40, 42 and 43. It is appreciated that since CELL A 50, CELL B 51 and CELL C 52 are cells in the same organism, the GENOME 38 of these cells, and the GENOMIC RECORDS, exemplified by 40, 42 and 43, the genome of these cells comprises, are identical in these cells.

As described above with reference to FIG. 5B, at its inception, CELL A 50 receives a maternal short RNA segment, designated by reference numeral 46, having a nucleotide sequence represented by A' and outlined by a broken line, which activates the FIBRO genomic record 40, thereby causing CELL A 50 to differentiate into a FIBROBLAST CELL 3. However, FIG. 6 elaborates some of the additional information 45 (FIG. 5A) of the genomic records: Genomic record may also comprise two short genomic sequences, referred to here as Daughter Cell Genomic Addresses. Blocks designated B and C are Daughter Cell Genomic Addresses of the FIBRO Genomic Record. At cell division, each parent cell transcribes two short RNA segments, corresponding to the two Daughter Cell Genomic Addresses of the Genomic Record of that parent cell, and transfers one to each of its two daughter cells. CELL A 50 transcribes and transfers to its two daughter cells 51 and 52, two short RNA segments, designated by reference numerals 49 and 53, outlined by a broken line and designated B' and C', corresponding to daughter cell genomic addresses designated B and C comprised in the FIBRO genomic record 40.

CELL B 51 therefore receives the above mentioned maternal short RNA segment designated 49 having a nucleotide sequence represented by B', which binds complementarily to genomic address designated B of the BONE genomic record 42, thereby activating this genomic record, which in turn causes CELL B 51 to differentiate into a BONE CELL 4. Similarly, CELL C 52 receives the above mentioned maternal short RNA segment designated 53 having a nucleotide sequence represented by C', which binds complementarily to genomic address designated C of a CARTILAGE genomic record 43, thereby activating this genomic record, which in turn causes CELL C 52 to differentiate into a CARTILAGE CELL 1 (FIG. 1).

It is appreciated that the mechanism illustrated by FIG. 6 enables an unlimited lineage of cells to divide into daughter cells containing the same DNA 5 (FIG. 1), and to determine the cell-fate of these daughter cells. For example, when CELL B 51 and CELL C 52 divide into their respective daughter cells (not shown), they will transfer short RNA segments designated by reference numerals 54-57, to their respective daughter cells. The cell fate of each of these daughter cells is effected by the identity of the maternal short RNA segments 54-57 they each receive, which in turn determine the genomic record activated.

Figure 7:
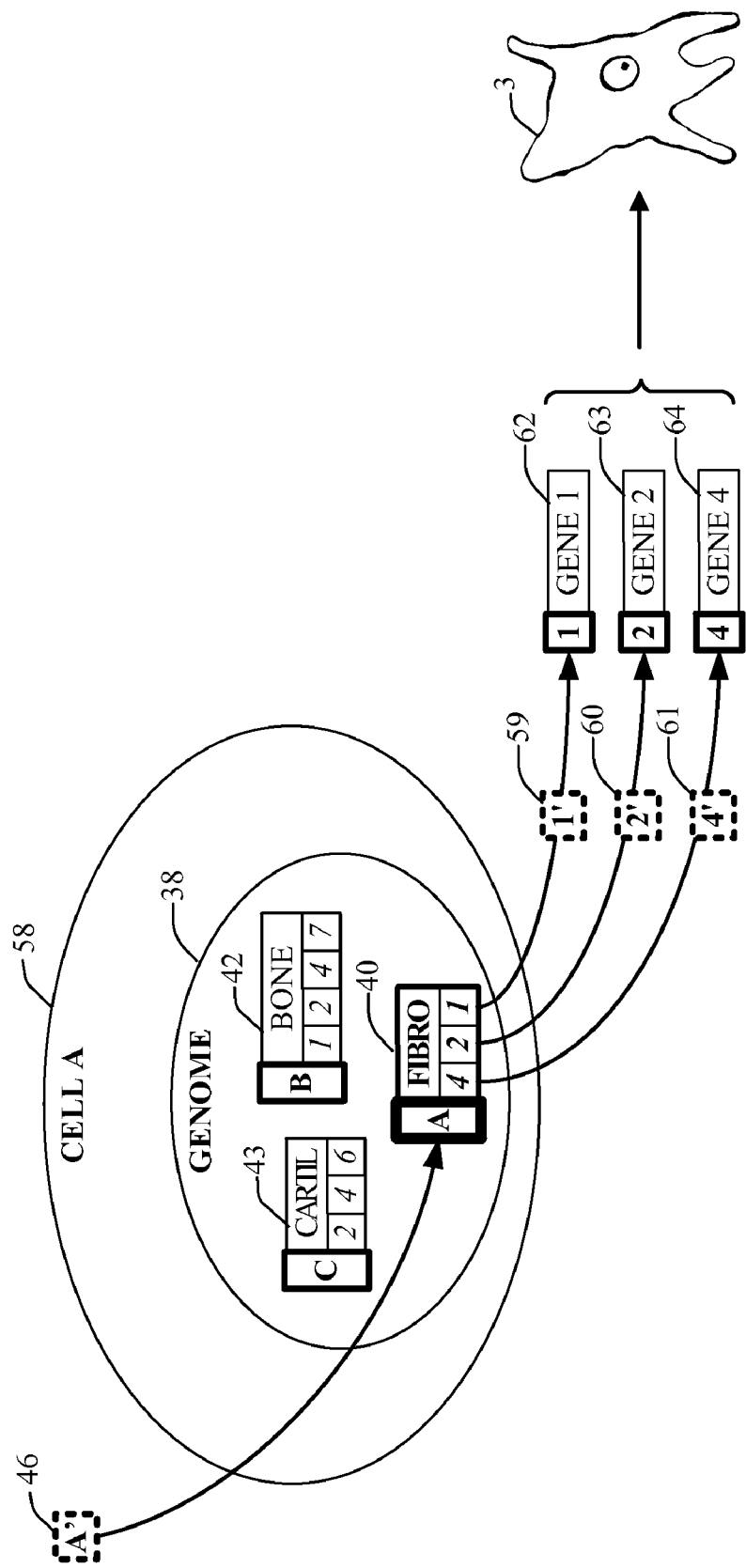
FIG. 7 is a schematic diagram illustrating a 'genomically programmed cell-specific protein expression modulation' concept of the conceptual model of the present invention, addressing the genomic differentiation enigma;>

Reference is now made to FIG. 7 which is a schematic diagram illustrating a "genomically programmed cell-specific protein expression modulation" concept of the conceptual model of the present invention, addressing the genomic differentiation enigma.

Cell A 58 receives a maternal short RNA segment designated 46 having a nucleotide sequence represented by A', which activates the FIBROBLAST genomic record 40, by complementarily binding to a binding site this genomic record comprises, the nucleotide sequence of which binding site is designated A. This is similar to the process shown in FIG. 5A. However, FIG. 7 further elaborates some of the additional information 45 (FIG. 1). The FIBROBLAST genomic record 40 comprises 3 short nucleotide segments, having nucleotide sequences symbolically represented by 1, 2 and 4 respectively, which encode 3 respective short RNA oligonucleotides, designated by reference numerals 59-61. Each of these short RNA oligonucleotides modulates expression of a respective one of the target genes GENE 1, GENE 2 and GENE 4, designated by reference numerals 62-64 respectively, by complementarily binding to a binding site sequence associated with that target gene. In a preferred embodiment of the present invention, the modulation of expression of target genes such as 62-64 comprises translation inhibition of target genes by complementarily binding to binding sites located in untranslated regions of the target genes. Modulation of expression of these genes results in CELL A 58 differentiating into a FIBROBLAST cell-type 3 (FIG. 1).

It is appreciated that the concept of genomic records each comprising a cluster of short RNA segments, which segments modulate expression of target genes thereby modulating differentiation, is compatible with the clusters of miRNA oligonucleotides of the present invention, and their translational inhibition of respective target genes by means of complementarily binding to binding sites located in the untranslated regions of mRNA of these target genes.

Figure 8:
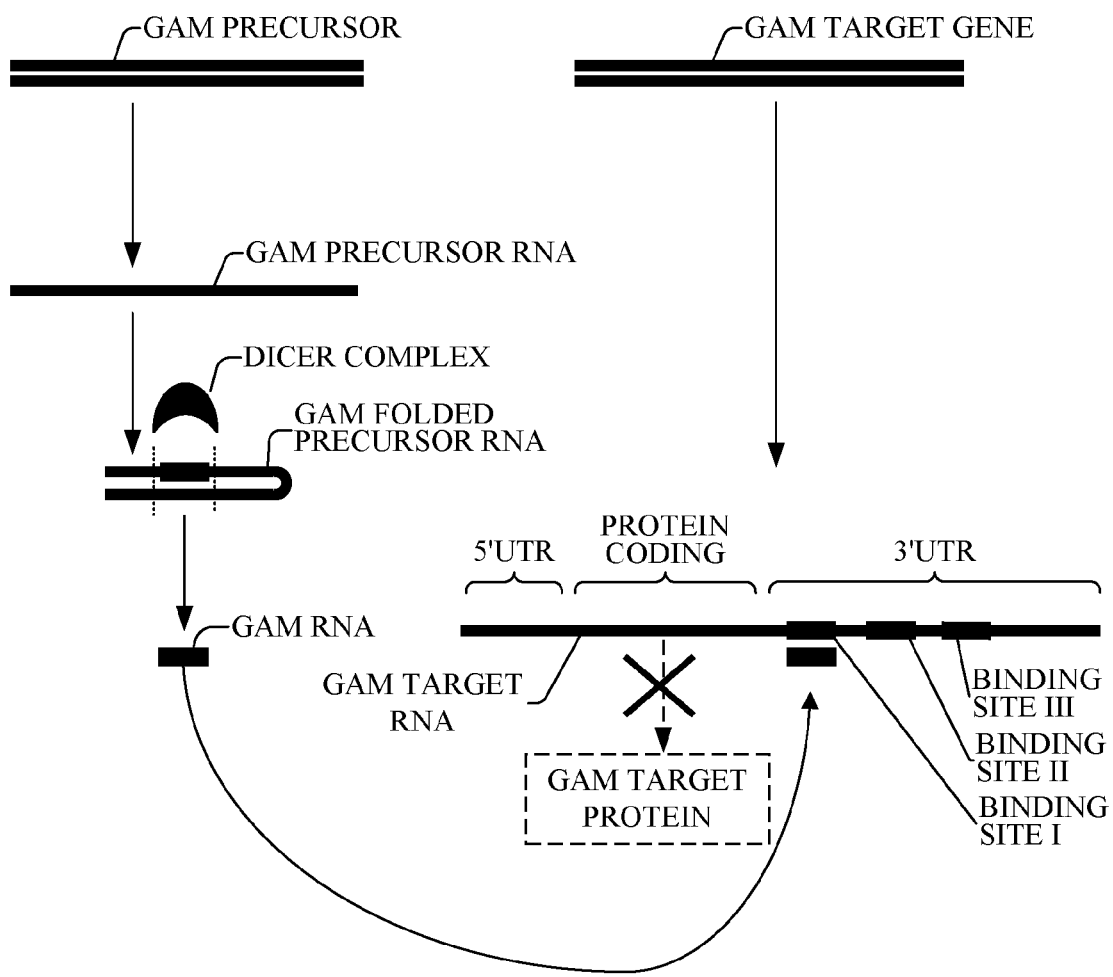
FIG. 8 is a simplified diagram illustrating a mode by which oligonucleotides of a novel group of oligonucleotides of the present invention, modulate expression of known target genes.

Reference is now made to FIG. 8, which is a simplified diagram describing a plurality of novel bioinformatically detected oligonucleotide of the present invention referred to here as Genomic Address Messenger (GAM) oligonucleotide, which modulates expression of respective target genes whose function and utility is known in the art.

GAM is a novel bioinformatically detectable regulatory, non protein coding, microRNA (miRNA)-like oligonucleotide. The method by which GAM is detected is described with additional reference to FIGS. 8-15.

GAM PRECURSOR is encoded by the human genome. GAM TARGET GENE is a gene encoded by the human genome.

GAM PRECURSOR encodes a GAM PRECURSOR RNA. Similar to other miRNA oligonucleotides GAM PRECURSOR RNA does not encode a protein.

GAM PRECURSOR RNA folds onto itself, forming GAM FOLDED PRECURSOR RNA which has a two-dimensional 'hairpin structure'. As is well known in the art, this 'hairpin structure', is typical of RNA encoded by known miRNA oligonucleotides, and is due to the fact that the nucleotide sequence of the first half of the RNA encoded by a miRNA oligonucleotide is a fully or partially complementary sequence of the nucleotide sequence of the second half thereof. By complementary is meant a sequence which is reversed and wherein each nucleotide is replaced by a complementary nucleotide, as is well known in the art (e.g. ATGGC is the complementary sequence of GCCAT). An enzyme complex designated DICER COMPLEX, 'dices' the GAM FOLDED PRECURSOR RNA yielding a GAM RNA in the form of a single stranded ~22 nt long RNA segment. As is known in the art, 'dicing' of a hairpin structured RNA precursor product to yield a short ~22 nt RNA segment is catalyzed by an enzyme complex Dicer RNaseIII together with other necessary proteins.

GAM TARGET GENE encodes a corresponding messenger RNA, GAM TARGET RNA. Each of the GAM TARGET RNAs of the present invention comprises three regions, as is typical of mRNA of a protein coding gene: a 5' untranslated region, a protein coding region and a 3' untranslated region, designated 5'UTR, PROTEIN CODING and 3'UTR respectively.

GAM RNA binds complementarily to one or more target binding sites located in untranslated regions of each of the GAM TARGET RNAs of the present invention. This complementary binding is due to the fact that the nucleotide sequence of GAM RNA is a partial or fully complementary sequence of the nucleotide sequence of each of the target binding sites. As an illustration, FIG. 8 shows three such target binding sites, designated BINDING SITE I, BINDING SITE II and BINDING SITE III respectively. It is appreciated that the number of target binding sites shown in FIG. 8 is only illustrative and that any suitable number of target binding sites may be present. It is further appreciated that although FIG. 8 shows target binding sites only in the 3'UTR region these target binding sites may be located instead in the 5'UTR region or in both 3'UTR and 5'UTR regions.

The complementary binding of GAM RNA to target binding sites on GAM TARGET RNA, such as BINDING SITE I, BINDING SITE II and BINDING SITE III, inhibits translation of each of the GAM TARGET RNAs of the present invention into GAM TARGET PROTEIN, which is shown surrounded by a broken line.

It is appreciated that GAM TARGET GENE in fact represents a plurality of GAM target genes. The mRNA of each one of this plurality of GAM target genes comprises one or more target binding sites, each having a nucleotide sequence which is at least partly complementary to GAM RNA and which when bound by GAM RNA causes inhibition of translation of the GAM target mRNA into a corresponding GAM target protein.

The mechanism of the translational inhibition exerted by GAM RNA on one or more GAM TARGET GENEs may be similar or identical to the known mechanism of translational inhibition exerted by known miRNA oligonucleotides.

Nucleotide sequences of each of a plurality of GAM oligonucleotides described by FIG. 8 and their respective genomic sources and genomic locations are set forth in Tables 1-3, hereby incorporated herein.

Nucleotide sequences of GAM PRECURSOR RNAs, and a schematic representation of a predicted secondary folding of GAM FOLDED PRECURSOR RNAs, of each of a plurality of GAM oligonucleotides described by FIG. 8 are set forth in Table 4, hereby incorporated herein.

Nucleotide sequences of diced' GAM RNAs of each of a plurality of GAM oligonucleotides described by FIG. 8 are set forth in Table 5, hereby incorporated herein.

Nucleotide sequences of target binding sites, such as BINDING SITE I, BINDING SITE II and BINDING SITE III found on GAM TARGET RNAs of each of a plurality of GAM oligonucleotides described by FIG. 8, and a schematic representation of the complementarity of each of these target binding sites to each of a plurality of GAM RNAs described by FIG. 8 are set forth in Tables 6-7, hereby incorporated herein.

It is appreciated that specific functions and accordingly utilities of each of a plurality of GAM oligonucleotides described by FIG. 8 are correlated with, and may be deduced from the identity of the GAM TARGET GENEs inhibited thereby, and whose functions are set forth in Table 8, hereby incorporated herein.

Studies documenting well known correlations between each of a plurality of GAM TARGET GENEs of the GAM oligonucleotides of FIG. 8, and known functions and diseases are listed in Table 9, hereby incorporated herein.

The present invention discloses a novel group of human oligonucleotides, belonging to the miRNA-like oligonucleotides group, here termed GAM oligonucleotides, for which a specific complementary binding has been determined bioinformatically.

Figure 9:
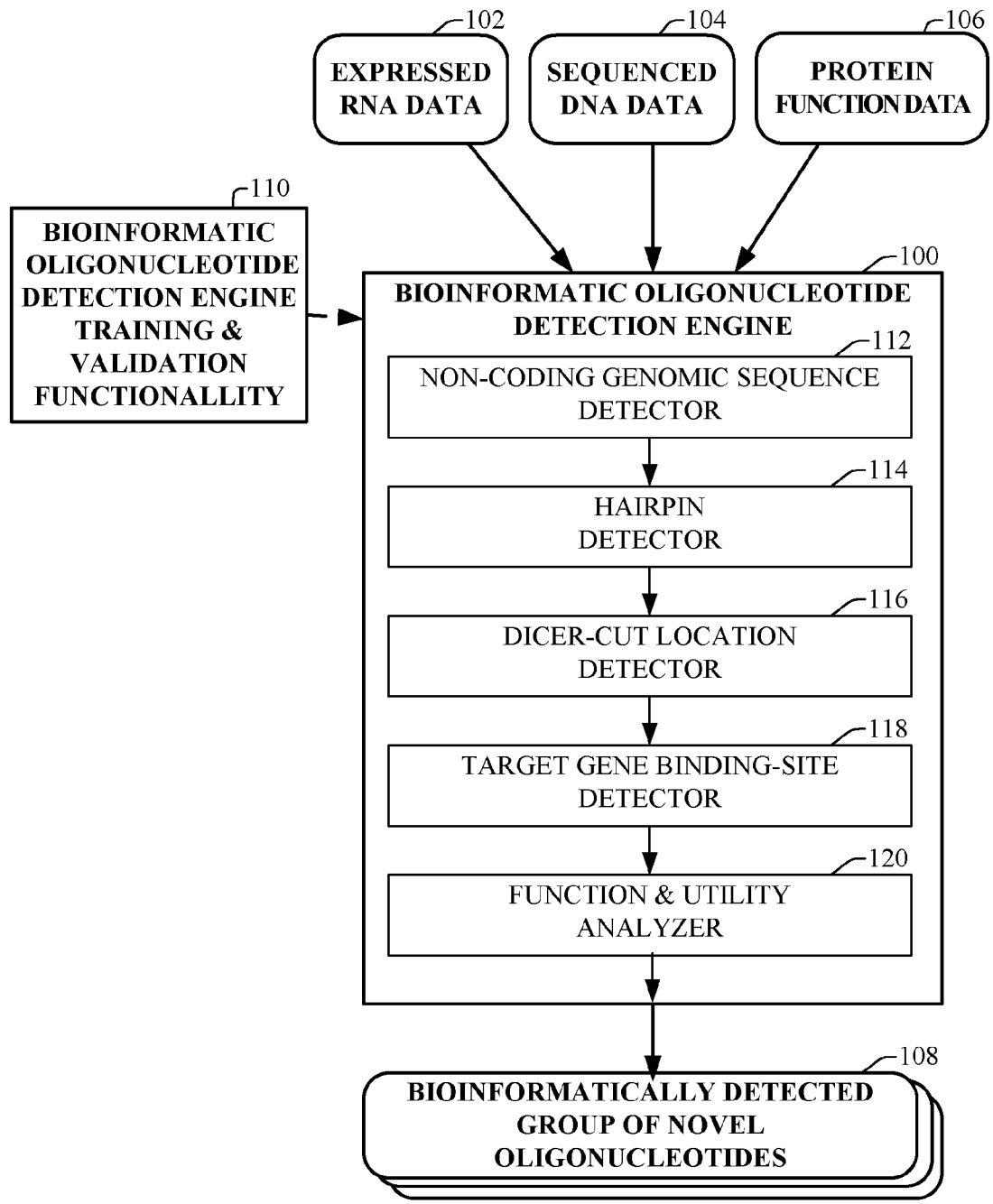
FIG. 9 is a simplified block diagram illustrating a bioinformatic oligonucleotide detection system capable of detecting oligonucleotides of the novel group of oligonucleotides of the present invention, which system is constructed and operative in accordance with a preferred embodiment of the present invention.

Reference is now made to FIG. 9 which is a simplified block diagram illustrating a bioinformatic oligonucleotide detection system and method constructed and operative in accordance with a preferred embodiment of the present invention.

An important feature of the present invention is a BIOINFORMATIC OLIGONUCLEOTIDE DETECTION ENGINE 100, which is capable of bioinformatically detecting oligonucleotides of the present invention.

The functionality of the BIOINFORMATIC OLIGONUCLEOTIDE DETECTION ENGINE 100 includes receiving EXPRESSED RNA DATA 102, SEQUENCED DNA DATA 104, and PROTEIN FUNCTION DATA 106; performing a complex process of analysis of this data as elaborated hereinbelow, and based on this analysis provides information, designated by reference numeral 108, identifying and describing features of novel oligonucleotides.

EXPRESSED RNA DATA 102 comprises published expressed sequence tags (EST) data, published mRNA data, as well as other published RNA data. SEQUENCED DNA DATA 104 comprises alphanumeric data representing genomic sequences and preferably including annotations such as information indicating the location of known protein coding regions relative to the genomic sequences.

PROTEIN FUNCTION DATA 106 comprises information from scientific publications e.g. physiological functions of known proteins and their connection, involvement and possible utility in treatment and diagnosis of various diseases.

EXPRESSED RNA DATA 102 and SEQUENCED DNA DATA 104 may preferably be obtained from data published by the National Center for Biotechnology Information (NCBI) at the National Institute of Health (NIH) (Jenuth, J. P. (2000). Methods Mol. Biol. 132:301-312 (2000), herein incorporated by reference) as well as from various other published data sources. PROTEIN FUNCTION DATA 106 may preferably be obtained from any one of numerous relevant published data sources, such as the Online Mendelian Inherited Disease In Man (OMIM™, Hamosh et al., Nucleic Acids Res. 30: 52-55 (2002)) database developed by John Hopkins University, and also published by NCBI (2000).

Prior to or during actual detection of BIOINFORMATICALLY DETECTED GROUP OF NOVEL OLIGONUCLEOTIDES 108 by the BIOINFORMATIC OLIGONUCLEOTIDE DETECTION ENGINE 100, BIOINFORMATIC OLIGONUCLEOTIDE DETECTION ENGINE TRAINING & VALIDATION FUNCTIONALITY 110 is operative. This functionality uses one or more known miRNA oligonucleotides as a training set to train the BIOINFORMATIC OLIGONUCLEOTIDE DETECTION ENGINE 100 to bioinformatically recognize miRNA-like oligonucleotides, and their respective potential target binding sites. BIOINFORMATIC OLIGONUCLEOTIDE DETECTION ENGINE TRAINING &VALIDATION FUNCTIONALITY 110 is further described hereinbelow with reference to FIG. 10.

The BIOINFORMATIC OLIGONUCLEOTIDE DETECTION ENGINE 100 preferably comprises several modules which are preferably activated sequentially, and are described as follows:

A NON-CODING GENOMIC SEQUENCE DETECTOR 112 operative to bioinformatically detect non-protein coding genomic sequences. The NON-CODING GENOMIC SEQUENCE DETECTOR 112 is further described herein below with reference to FIGS. 11A and 11B.

A HAIRPIN DETECTOR 114 operative to bioinformatically detect genomic 'hairpin-shaped' sequences, similar to GAM FOLDED PRECURSOR RNA (FIG. 8). The HAIRPIN DETECTOR 114 is further described herein below with reference to FIGS. 12A and 12B.

A DICER-CUT LOCATION DETECTOR 116 operative to bioinformatically detect the location on a GAM FOLDED PRECURSOR RNA which is enzymatically cut by DICER COMPLEX (FIG. 8), yielding diced GAM RNA. The DICER-CUT LOCATION DETECTOR 116 is further described herein below with reference to FIGS. 13A-13C.

A TARGET GENE BINDING-SITE DETECTOR 118 operative to bioinformatically detect target genes having binding sites, the nucleotide sequence of which is partially complementary to that of a given genomic sequence, such as a nucleotide sequence cut by DICER COMPLEX. The TARGET GENE BINDING-SITE DETECTOR 118 is further described hereinbelow with reference to FIGS. 14A and 14B.

A FUNCTION & UTILITY ANALYZER 120 operative to analyze the function and utility of target genes in order to identify target genes which have a significant clinical function and utility. The FUNCTION & UTILITY ANALYZER 120 is further described hereinbelow with reference to FIG. 15.

According to a preferred embodiment of the present invention the engine 100 may employ a cluster of 40 PCs (XEON®, 2.8 GHz, with 80 GB storage each), connected by Ethernet to 8 servers (2-CPU, XEON™ 1.2-2.2 GHz, with ~200 GB storage each), combined with an 8-processor server (8-CPU, Xeon 550 Mhz w/8 GB RAM) connected via 2 HBA fiber-channels to an EMC CLARIION™ 100-disks, 3.6 Terabyte storage device. A preferred embodiment of the present invention may also preferably comprise software which utilizes a commercial database software program, such as MICROSOFT™ SQL Server 2000. It is appreciated that the above mentioned hardware configuration is not meant to be limiting, and is given as an illustration only. The present invention may be implemented in a wide variety of hardware and software configurations.

The present invention discloses 15454 novel oligonucleotides of the GAM group of oligonucleotides, which have been detected bioinformatically and 681 novel polynucleotides of the GR group of polynucleotides, which have been detected bioinformatically. Laboratory confirmation of bioinformatically predicted oligonucleotides of the GAM group of oligonucleotides, and several bioinformatically predicted polynucleotides of the GR group of polynucleotides, is described hereinbelow with reference to FIGS. 21-24D.

Figure 10:
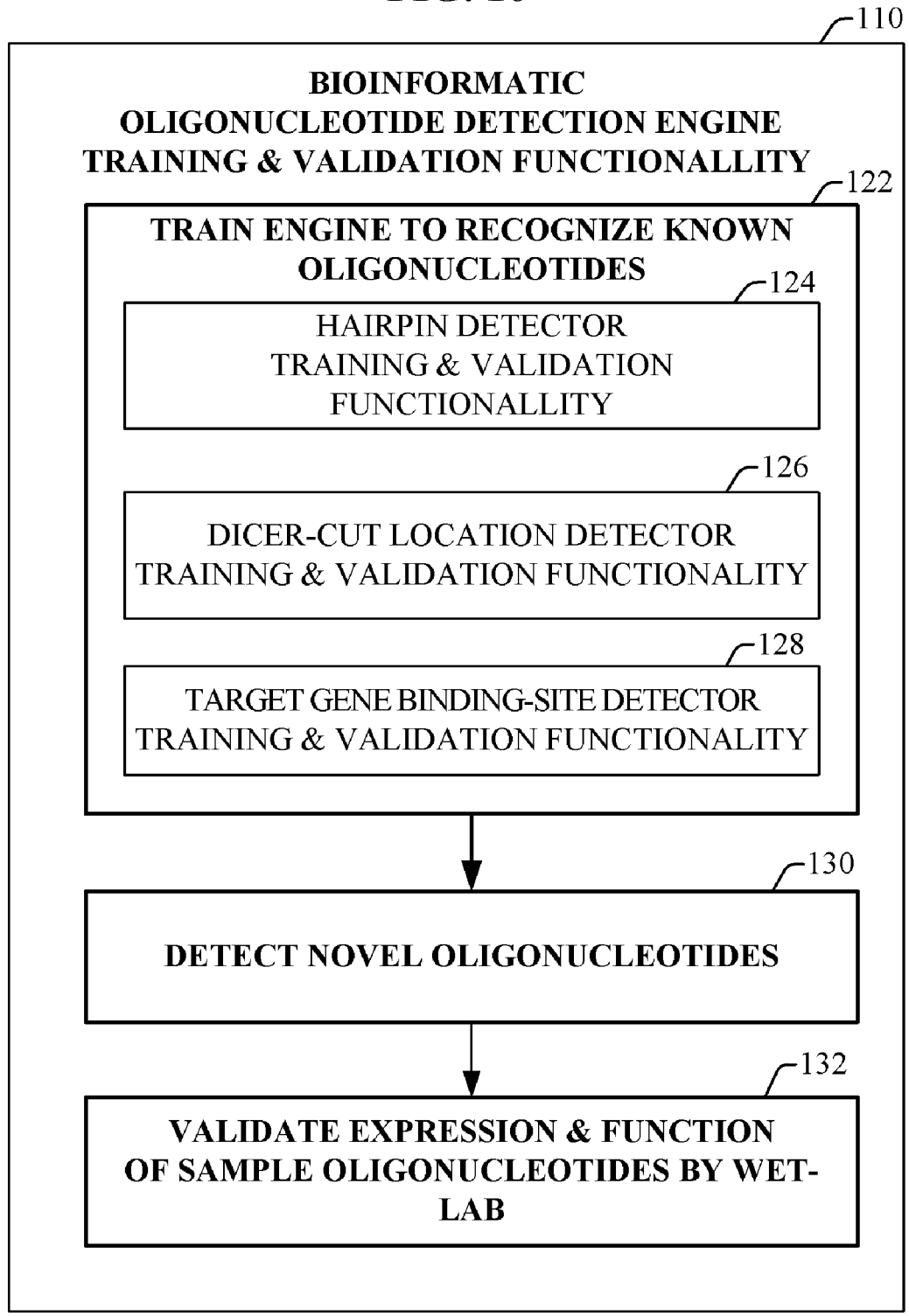
FIG. 10 is a simplified flowchart illustrating operation of a mechanism for training of a computer system to recognize the novel oligonucleotides of the present invention, which mechanism is constructed and operative in accordance with a preferred embodiment of the present invention.

Reference is now made to FIG. 10 which is a simplified flowchart illustrating operation of a preferred embodiment of the BIOINFORMATIC OLIGONUCLEOTIDE DETECTION ENGINE TRAINING & VALIDATION FUNCTIONALITY 110 described hereinabove with reference to FIG. 9.

BIOINFORMATIC OLIGONUCLEOTIDE DETECTION ENGINE TRAINING & VALIDATION FUNCTIONALITY 110 begins by training the BIOINFORMATIC OLIGONUCLEOTIDE DETECTION ENGINE 100 (FIG. 9) to recognize one or more known miRNA oligonucleotides, as designated by reference numeral 122. This training step comprises HAIRPIN DETECTOR TRAINING & VALIDATION FUNCTIONALITY 124, further described hereinbelow with reference to FIG. 12A, DICER-CUT LOCATION DETECTOR TRAINING & VALIDATION FUNCTIONALITY 126, further described hereinbelow with reference to FIGS. 13A and 13B, and TARGET GENE BINDING-SITE DETECTOR TRAINING & VALIDATION FUNCTIONALITY 128, further described hereinbelow with reference to FIG. 14A.

Next, the BIOINFORMATIC OLIGONUCLEOTIDE DETECTION ENGINE TRAINING & VALIDATION FUNCTIONALITY 110 is operative bioinformatically detect novel oligonucleotides, using BIOINFORMATIC OLIGONUCLEOTIDE DETECTION ENGINE 100 (FIG. 9), as designated by reference numeral 130. Wet lab experiments are preferably conducted in order to validate expression and preferably function of some samples of the novel oligonucleotides detected by the BIOINFORMATIC OLIGONUCLEOTIDE DETECTION ENGINE 100, as designated by reference numeral 132. FIGS. 22A-24D illustrate examples of wet-lab validation of sample novel human oligonucleotides bioinformatically detected in accordance with a preferred embodiment of the present invention.

Figure 11A:
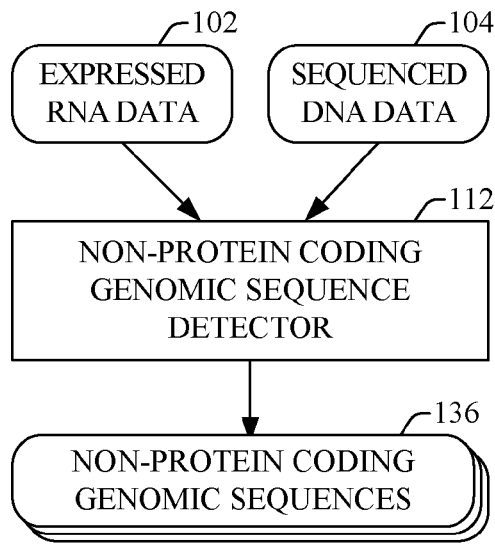
FIG. 11A is a simplified block diagram of a non-coding genomic sequence detector constructed and operative in accordance with a preferred embodiment of the present invention.

Reference is now made to FIG. 11A which is a simplified block diagram of a preferred implementation of the NON-CODING GENOMIC SEQUENCE DETECTOR 112 described hereinabove with reference to FIG. 9. The NON-PROTEIN CODING GENOMIC SEQUENCE DETECTOR 112 preferably receives at least two types of published genomic data: EXPRESSED RNA DATA 102 and SEQUENCED DNA DATA 104. The EXPRESSED RNA DATA 102 may include, inter alia, EST data, EST clusters data, EST genome alignment data and mRNA data. Sources for EXPRESSED RNA DATA 102 include NCBI dbEST, NCBI UniGene clusters and mapping data, and TIGR gene indices (Kirkness F. and Kerlavage, A. R., Methods Mol. Biol. 69:261-268 (1997)). SEQUENCED DNA DATA 104 may include sequence data (FASTA format files), and feature annotations (GenBank file format) mainly from NCBI databases. Based on the above mentioned input data, the NON-PROTEIN CODING GENOMIC SEQUENCE DETECTOR 112 produces a plurality of NON-PROTEIN CODING GENOMIC SEQUENCES 136. Preferred operation of the NON-PROTEIN CODING GENOMIC SEQUENCE DETECTOR 112 is described hereinbelow with reference to FIG. 11B.

Figure 11B:
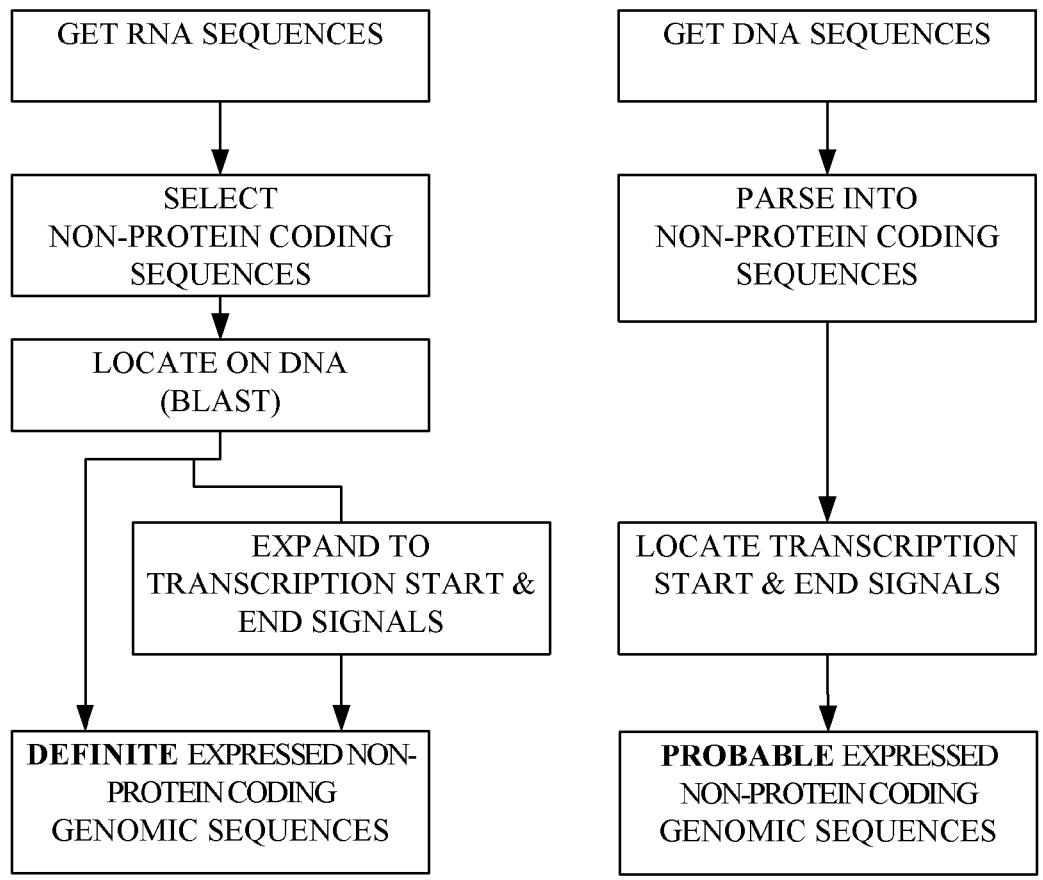
FIG. 11B is a simplified flowchart illustrating operation of a non-coding genomic sequence detector constructed and operative in accordance with a preferred embodiment of the present invention.

Reference is now made to FIG. 11B which is a simplified flowchart illustrating a preferred operation of the NON-CODING GENOMIC SEQUENCE DETECTOR 112 of FIG. 9. Detection of NON-PROTEIN CODING GENOMIC SEQUENCES 136, generally preferably progresses along one of the following two paths:

A first path for detecting NON-PROTEIN CODING GENOMIC SEQUENCES 136 (FIG. 11A) begins with receipt of a plurality of known RNA sequences, such as EST data. Each RNA sequence is first compared with known protein-coding DNA sequences, in order to select only those RNA sequences which are non-protein coding, i.e. intergenic or intronic sequences. This can preferably be performed by using one of many alignment algorithms known in the art, such as BLAST (Altschul et al., J. Mol. Biol. 215:403-410 (1990)). This sequence comparison preferably also provides localization of the RNA sequence on the DNA sequences.

Alternatively, selection of non-protein coding RNA sequences and their localization on the DNA sequences can be performed by using publicly available EST cluster data and genomic mapping databases, such as the UNIGENE database published by NCBI or the TIGR database. Such databases, map expressed RNA sequences to DNA sequences encoding them, find the correct orientation of EST sequences, and indicate mapping of ESTs to protein coding DNA regions, as is well known in the art. Public databases, such as TIGR, may also be used to map an EST to a cluster of ESTs, known in the art as Tentative Human Consensus and assumed to be expressed as one segment. Publicly available genome annotation databases, such as NCBIs GenBank, may also be used to deduce expressed intronic sequences.

Optionally, an attempt may be made to "expand" the non-protein RNA sequences thus found, by searching for transcription start and end signals, respectively upstream and downstream of the location of the RNA on the DNA, as is well known in the art.

A second path for detecting NON-PROTEIN CODING GENOMIC SEQUENCES 136 (FIG. 11A) begins with receipt of DNA sequences. The DNA sequences are parsed into non protein coding sequences, using published DNA annotation data, by extracting those DNA sequences which are between known protein coding sequences. Next, transcription start and end signals are sought. If such signals are found, and depending on their robustness, probable expressed non-protein coding genomic sequences are obtained. Such approach is especially useful for identifying novel GAM oligonucleotides which are found in proximity to other known miRNA oligonucleotides, or other wet-lab validated GAM oligonucleotides. Since, as described hereinbelow with reference to FIG. 16, GAM oligonucleotides are frequently found in clusters; sequences located near known miRNA oligonucleotides are more likely to contain novel GAM oligonucleotides. Optionally, sequence orthology, i.e. sequence conservation in an evolutionary related species, may be used to select genomic sequences having a relatively high probability of containing expressed novel GAM oligonucleotides.

Figure 12A:
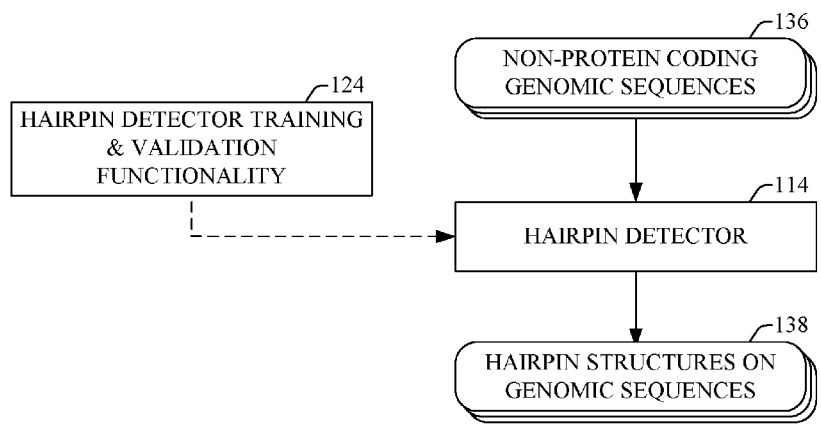
FIG. 12A is a simplified block diagram of a hairpin detector constructed and operative in accordance with a preferred embodiment of the present invention.

Reference is now made to FIG. 12A which is a simplified block diagram of a preferred implementation of the HAIRPIN DETECTOR 114 described hereinabove with reference to FIG. 9.

The goal of the HAIRPIN DETECTOR 114 is to detect hairpin-shaped genomic sequences, similar to those of known miRNA oligonucleotides. A hairpin-shaped genomic sequence is a genomic sequence, having a first half which is at least partially complementary to a second half thereof, which causes the halves to folds onto themselves, thereby forming a hairpin structure, as mentioned hereinabove with reference to FIG. 8.

The HAIRPIN DETECTOR 114 (FIG. 9) receives a plurality of NON-PROTEIN CODING GENOMIC SEQUENCES 136 (FIG. 11A). Following operation of HAIRPIN DETECTOR TRAINING & VALIDATION FUNCTIONALITY 124 (FIG. 10), the HAIRPIN DETECTOR 114 is operative to detect and output hairpin-shaped sequences, which are found in the NON-PROTEIN CODING GENOMIC SEQUENCES 136. The hairpin-shaped sequences detected by the HAIRPIN DETECTOR 114 are designated HAIRPINS STRUCTURES ON GENOMIC SEQUENCES 138. A preferred mode of operation of the HAIRPIN DETECTOR 114 is described hereinbelow with reference to FIG. 12B.

HAIRPIN DETECTOR TRAINING & VALIDATION FUNCTIONALITY 124 includes an iterative process of applying the HAIRPIN DETECTOR 114 to known hairpin shaped miRNA precursor sequences, calibrating the HAIRPIN DETECTOR 114 such that it identifies a training set of known hairpin-shaped miRNA precursor sequences, as well as other similarly hairpin-shaped sequences. In a preferred embodiment of the present invention, the HAIRPIN DETECTOR TRAINING & VALIDATION FUNCTIONALITY 124 trains the HAIRPIN DETECTOR 114 and validates each of the steps of operation thereof described hereinbelow with reference to FIG. 12B The HAIRPIN DETECTOR TRAINING & VALIDATION FUNCTIONALITY 124 preferably uses two sets of data: the aforesaid training set of known hairpin-shaped miRNA precursor sequences, such as hairpin-shaped miRNA precursor sequences of 440 miRNA oligonucleotides of *H. sapiens, M. musculus, C. elegans, C. Brigssae* and *D. Melanogaster*, annotated in the RFAM database (Griffiths-Jones 2003), and a background set of about 1000 hairpin-shaped sequences found in expressed non-protein coding human genomic sequences. The background set is expected to comprise some valid, previously undetected hairpin-shaped miRNA-like precursor sequences, and many hairpin-shaped sequences which are not hairpin-shaped miRNA-like precursors.

In a preferred embodiment of the present invention the efficacy of the HAIRPIN DETECTOR 114 (FIG. 9) is confirmed. For example, when a similarity threshold is chosen such that 87% of the known hairpin-shaped miRNA precursors are successfully predicted, only 21.8% of the 1000 background set of hairpin-shaped sequences are predicted to be hairpin-shaped miRNA-like precursors.

Figure 12B:
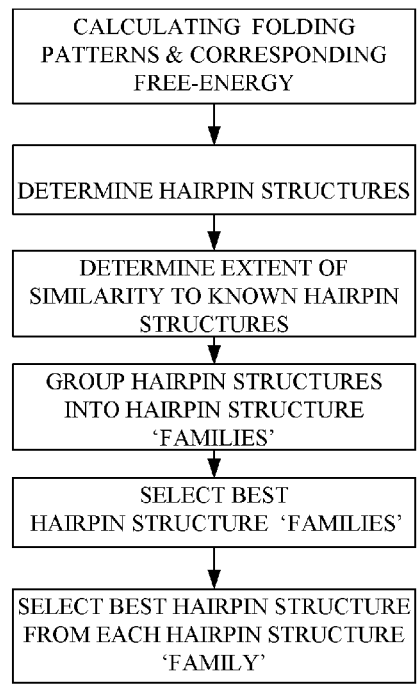
FIG. 12B is a simplified flowchart illustrating operation of a hairpin detector constructed and operative in accordance with a preferred embodiment of the present invention.

Reference is now made to FIG. 12B which is a simplified flowchart illustrating preferred operation of the HAIRPIN DETECTOR 114 of FIG. 9. The HAIRPIN DETECTOR 114 preferably initially uses a secondary structure folding algorithm based on free-energy minimization, such as the MFOLD algorithm, described in Mathews et al. J. Mol. Biol. 288:911-940 (1999) and Zuker, M. Nucleic Acids Res. 31: 3406-3415 (2003), the disclosure of which is hereby incorporated by reference. This algorithm is operative to calculate probable secondary structure folding patterns of the NON-PROTEIN CODING GENOMIC SEQUENCES 136 (FIG. 11A) as well as the free-energy of each of these probable secondary folding patterns. The secondary structure folding algorithm, such as the MFOLD algorithm (Mathews, 1997; Zuker 2003), typically provides a listing of the base-pairing of the folded shape, i.e. a listing of each pair of connected nucleotides in the sequence.

Next, the HAIRPIN DETECTOR 114 analyzes the results of the secondary structure folding patterns, in order to determine the presence and location of hairpin folding structures. The goal of this second step is to assess the base-pairing listing provided by the secondary structure folding algorithm, in order to determine whether the base-pairing listing describes one or more hairpin type bonding pattern. Preferably, sequence segment corresponding to a hairpin structure is then separately analyzed by the secondary structure folding algorithm in order to determine its exact folding pattern and free-energy.

The HAIRPIN DETECTOR 114 then assesses the hairpin structures found by the previous step, comparing them to hairpin structures of known miRNA precursors, using various characteristic hairpin structure features such as its free-energy and its thermodynamic stability, the amount and type of mismatched nucleotides and the existence of sequence repeat-elements, number of mismatched nucleotides in positions 18-22 counting from loop, and Percent of G nucleotide. Only hairpins that bear statistically significant resemblance to the training set of hairpin structures of known miRNA precursors, according to the abovementioned parameters, are accepted.

In a preferred embodiment of the present invention, similarity to the training set of hairpin structures of known miRNA precursors is determined using a "similarity score" which is calculated using a multiplicity of terms, where each term is a function of one of the above-mentioned hairpin structure features. The parameters of each function are found heuristically from the set of hairpin structures of known miRNA precursors, as described hereinabove with reference to HAIRPIN DETECTOR TRAINING & VALIDATION FUNCTIONALITY 124 (FIG. 10). The selection of the features and their function parameters is optimized so as to achieve maximized separation between the distribution of similarity scores validated miRNA-precursor hairpin structures, and the distribution of similarity scores of hairpin structures detected in the background set mentioned hereinabove with reference to FIG. 12B.

In an alternative preferred embodiment of the present invention, the step described in the preceding paragraph may be split into two stages. A first stage implements a simplified scoring method, typically based on thresholding a subset of the hairpin structure features described hereinabove, and may employ a minimum threshold for hairpin structure length and a maximum threshold for free energy. A second stage is preferably more stringent, and preferably employs a full calculation of the weighted sum of terms described hereinabove. The second stage preferably is performed only on the subset of hairpin structures that survived the first stage.

The HAIRPIN DETECTOR 114 also attempts to select hairpin structures whose thermodynamic stability is similar to that of hairpin structures of known miRNA precursors. This may be achieved in various ways. A preferred embodiment of the present invention utilizes the following methodology, preferably comprising three logical steps:

First, the HAIRPIN DETECTOR 114 attempts to group hairpin structures into "families" of closely related hairpin structures. As is known in the art, a secondary structure folding algorithm typically provides multiple alternative folding patterns, for a given genomic sequence and indicates the free energy of each alternative folding pattern. It is a particular feature of the present invention that the HAIRPIN DETECTOR 114 preferably assesses the various hairpin structures appearing in the various alternative folding patterns and groups' hairpin structures which appear at identical or similar sequence locations in various alternative folding patterns into common sequence location based "families" of hairpins. For example, all hairpin structures whose center is within 7 nucleotides of each other may be grouped into a family". Hairpin structures may also be grouped into a family" if their nucleotide sequences are identical or overlap to a predetermined degree.

It is also a particular feature of the present invention that the hairpin structure "families" are assessed in order to select only those families which represent hairpin structures that are as thermodynamically stable as those of hairpin structures of known miRNA precursors. Preferably only families which are represented in at least a selected majority of the alternative secondary structure folding patterns, typically 65%, 80% or 100% are considered to be sufficiently stable. Our tests suggest that only about 50% of the hairpin structures, predicted by the MFOLD algorithm with default parameters, are members of sufficiently stable families, comparing to about 90% of the hairpin structures that contain known miRNAs. This percent depends on the size of the fraction that was fold. In an alternative embodiment of the present invention we use fractions of size 1000 nts as preferable size. Different embodiment uses other sizes of genomics sequences, more or less strict demand for representation in the alternative secondary structure folding patterns.

It is an additional particular feature of the present invention that the most suitable hairpin structure is selected from each selected family. For example, a hairpin structure which has the greatest similarity to the hairpin structures appearing in alternative folding patterns of the family may be preferred. Alternatively or additionally, the hairpin structures having relatively low free energy may be preferred.

Alternatively or additionally considerations of homology to hairpin structures of other organisms and the existence of clusters of thermodynamically stable hairpin structures located adjacent to each other along a sequence may be important in selection of hairpin structures. The tightness of the clusters in terms of their location and the occurrence of both homology and clusters may be of significance.

Figure 13A:
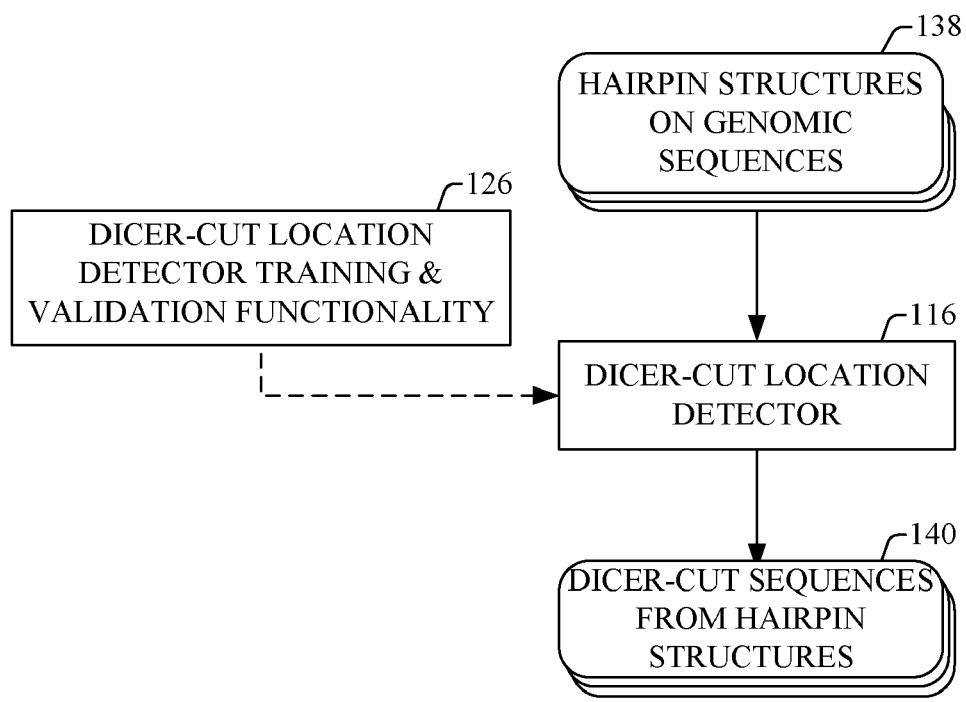
FIG. 13A is a simplified block diagram of a dicer-cut location detector constructed and operative in accordance with a preferred embodiment of the present invention.
Figure 13B:
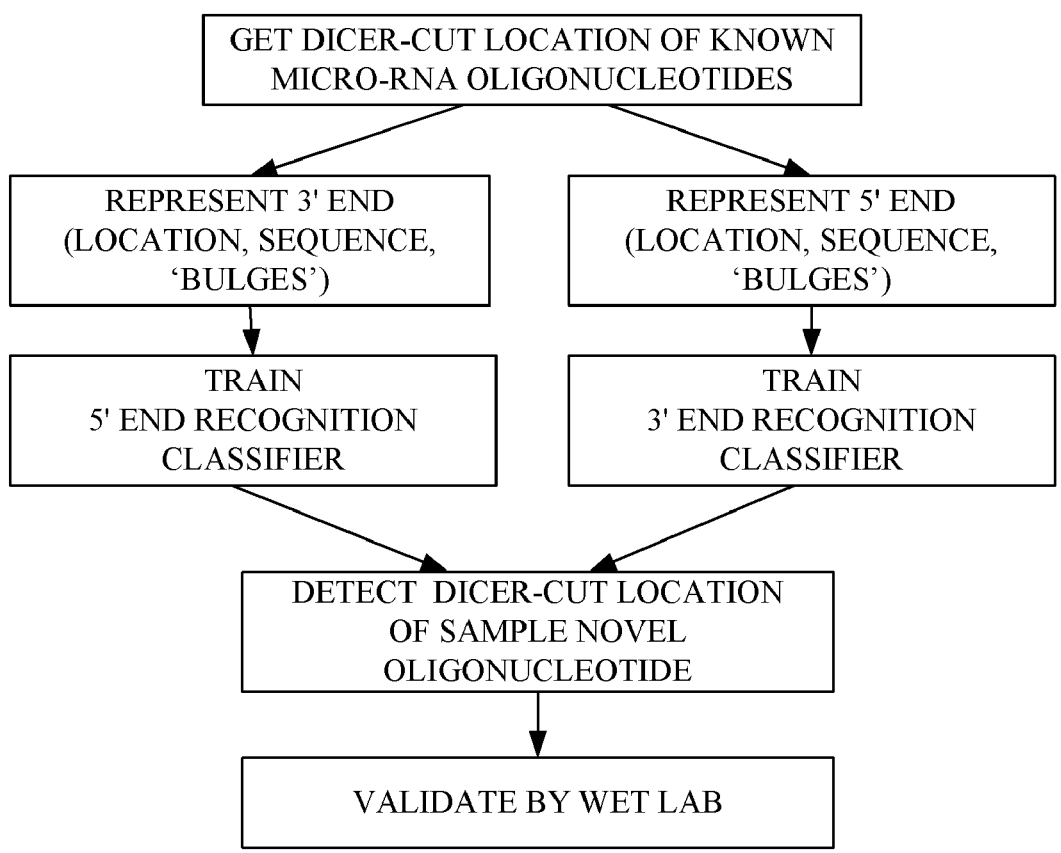
FIG. 13B is a simplified flowchart illustrating training of a dicer-cut location detector constructed and operative in accordance with a preferred embodiment of the present invention.
Figure 13C:
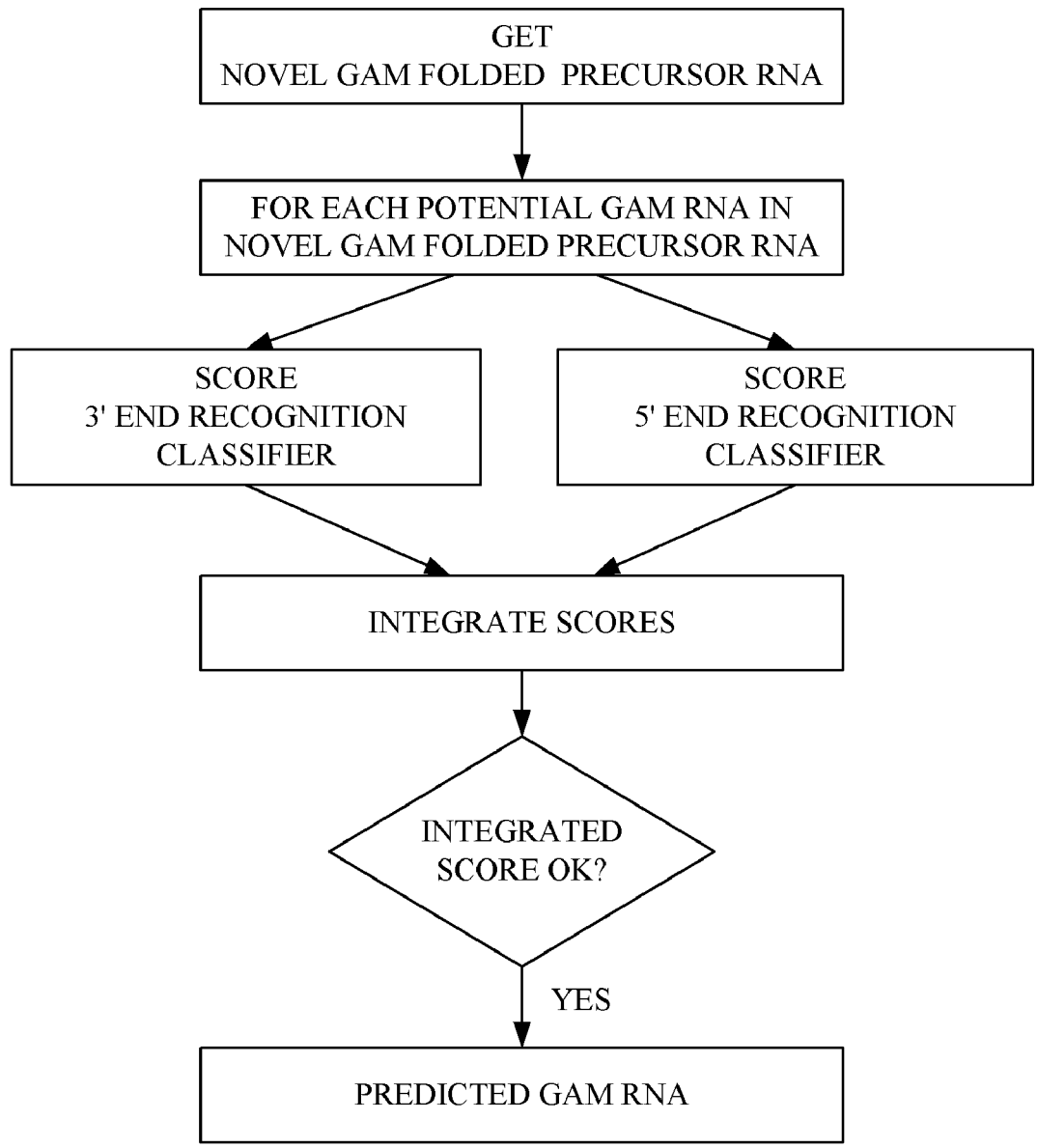
FIG. 13C is a simplified flowchart illustrating operation of a dicer-cut location detector constructed and operative in accordance with a preferred embodiment of the present invention.

Reference is now made to FIGS. 13A-13C which together describe the structure and operation of the DICER-CUT LOCATION DETECTOR 116, described hereinabove with FIG. 9.

FIG. 13A is a simplified block diagram of a preferred implementation of the DICER-CUT LOCATION DETECTOR 116. The goal of the DICER-CUT LOCATION DETECTOR 116 is to detect the location in which the DICER COMPLEX, described hereinabove with reference to FIG. 8, dices GAM FOLDED PRECURSOR RNA, yielding GAM RNA.

The DICER-CUT LOCATION DETECTOR 116 therefore receives a plurality of HAIRPIN STRUCTURES ON GENOMIC SEQUENCES 138 (FIG. 12A), and following operation of DICER-CUT LOCATION DETECTOR TRAINING & VALIDATION FUNCTIONALITY 126 (FIG. 10), is operative to detect a plurality of DICER-CUT SEQUENCES FROM HAIRPIN STRUCTURES 140.

Reference is now made to FIG. 13B which is a simplified flowchart illustrating a preferred implementation of DICER-CUT LOCATION DETECTOR TRAINING & VALIDATION FUNCTIONALITY 126.

A general goal of the DICER-CUT LOCATION DETECTOR TRAINING & VALIDATION FUNCTIONALITY 126 is to analyze the dicer-cut locations of known diced miRNA on respective hairpin shaped miRNA precursors in order to determine a common pattern in these locations, which can be used to predict dicer cut locations on GAM folded precursor RNAs.

The dicer-cut locations of known miRNA precursors are obtained and studied. Locations of the 5' and/or 3' ends of the known diced miRNAs are preferably represented by their respective distances from the 5' end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor.

One or more of the foregoing location metrics may be employed in the training and validation functionality. Additionally, metrics related to the nucleotide content of the diced miRNA and/or of the hairpin shaped miRNA precursor may be employed.

In a preferred embodiment of the present invention, DICER-CUT LOCATION DETECTOR TRAINING & VALIDATION FUNCTIONALITY 126 preferably employs standard machine learning techniques known in the art of machine learning for analysis of existing patterns in a given "training set" of examples. These techniques are capable, to a certain degree, of detecting similar patterns in other, previously unseen examples. Such machine learning techniques include, but are not limited to neural networks, Bayesian networks, Support Vector Machines (SVM), Genetic Algorithms, Markovian modeling, Maximum Likelihood modeling, Nearest Neighbor algorithms, Decision trees and other techniques, as is well known in the art.

In accordance with one embodiment of the present invention, machine learning predictors, such as a Support Vector Machine (SVM) predictor, are applied to the aforementioned training set and are operative, for example to test every possible nucleotide on a hairpin as a candidate for being the 5' end or the 3' end of a diced GAM RNA. More preferred machine learning predictors include predictors based on Nearest Neighbor, Bayesian modeling, and K-nearest-neighbor algorithms. A training set of the known miRNA precursor sequences is preferably used for training multiple separate classifiers or predictors, each of which produces a model for the 5' and/or 3' end locations of a diced miRNA with respect to its hairpin precursor. The models take into account one or more of the various miRNA location metrics described above.

Performance of the resulting predictors, evaluated on the abovementioned validation set of 440 published miRNAs using k-fold cross validation (Mitchell, 1997) with k=3, is found to be as follows: in 70% of known miRNAs 5'-end location is correctly determined by an SVM predictor within up to 2 nucleotides; a Nearest Neighbor (EDIT DISTANCE) predictor achieves 56% accuracy (247/440); a Two-Phased predictor that uses Bayesian modeling (TWO PHASED) achieves 80% accuracy (352/440), when only the first phase is used. When the second phase (strand choice) is implemented by a nave Bayesian model the accuracy is 55% (244/440), and when the K-nearest-neighbor modeling is used for the second phase, 374/440 decision are made and the accuracy is 65% (242/374). A K-nearest-neighbor predictor (FIRST-K) achieves 61% accuracy (268/440). The accuracies of all predictors are considerably higher on top scoring subsets of published miRNA.

Finally, in order to validate the efficacy and accuracy of the DICER-CUT LOCATION DETECTOR 116, a sample of novel oligonucleotides detected thereby is preferably selected, and validated by wet lab. Laboratory results validating the efficacy of the DICER-CUT LOCATION DETECTOR 116 are described hereinbelow with reference to FIGS. 21-24D.

Reference is now made to FIG. 13C which is a simplified flowchart illustrating operation of DICER-CUT LOCATION DETECTOR 116 (FIG. 9), constructed and operative in accordance with a preferred embodiment of the present invention. The DICER CUT LOCATION DETECTOR 116 preferably comprises a machine learning computer program module, which is trained to recognize dicer-cut locations on known hairpin-shaped miRNA precursors, and based on this training, is operable to detect dicer-cut locations of novel GAM RNAs (FIG. 8) on GAM FOLDED PRECURSOR RNAs (FIG. 8). In a preferred embodiment of the present invention, the dicer-cut location module preferably utilizes machine learning algorithms, such as known Support Vector Machine (SVM) and more preferably: known Bayesian modeling, Nearest Neighbors, and K-nearest-neighbor algorithms.

When initially assessing a novel GAM FOLDED PRECURSOR RNA, all 19-24 nucleotide long segments thereof are initially considered as "potential GAM RNAs", since the dicer-cut location is initially unknown.

For each such potential GAM RNA, the location of its 5' end or the locations of its 5' and 3' ends are scored by at least one recognition classifier or predictor.

In a preferred embodiment of the present invention, the DICER-CUT LOCATION DETECTOR 116 (FIG. 9) may use a Support Vector Machine predictor trained on and operating on features such as the following:

Locations of the 5' and/or 3' ends of the known diced miRNAs, which are preferably represented by their respective distances from the 5 end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor; and secondarily Metrics related to the nucleotide content of the diced miRNA and/or of the hairpin shaped miRNA precursor.

In another preferred embodiment of the present invention, the DICER-CUT LOCATION DETECTOR 116 (FIG. 9) preferably employs an "EDIT DISTANCE" predictor, which seeks sequences that are similar to those of known miRNAs, utilizing a Nearest Neighbor algorithm, where a similarity metric between two sequences is a variant of the Edit Distance algorithm (Gusfield, 1997). The EDIT DISTANCE predictor is based on an observation that miRNA oligonucleotides tend to form clusters, the members of which show marked sequence similarity.

In yet another preferred embodiment of the present invention, the DICER-CUT LOCATION DETECTOR 116 (FIG. 9) preferably uses a "TWO PHASE" predictor, which predicts the dicer-cut location in two distinct phases: (a) selecting a double-stranded segment of the GAM FOLDED PRECURSOR RNA (FIG. 8) comprising the GAM RNA by nave Bayesian modeling and (b) detecting which strand of the double-stranded segment contains GAM RNA (FIG. 8) by employing either nave or by K-nearest-neighbor modeling. K-nearest-neighbor modeling is a variant of the 'FIRST-K' predictor described hereinbelow, with parameters optimized for this specific task. The 'TWO PHASE' predictor may be operated in two modes: either utilizing only the first phase and thereby producing two alternative dicer-cut location predictions, or utilizing both phases and thereby producing only one final dicer-cut location.

In still another preferred embodiment of the present invention, the DICER-CUT LOCATION DETECTOR 116 preferably uses a "FIRST-K" predictor, which utilizes a K-nearestneighbor algorithm. The similarity metric between any two sequences is 1-E/L, where L is a parameter, preferably 8-10 and E is the edit distance between the two sequences, taking into account only the first L nucleotides of each sequence. If the K-nearest-neighbor scores of two or more locations on the GAM FOLDED PRECURSOR RNA (FIG. 8) are not significantly different, these locations are further ranked by a Bayesian model, similar to the one described hereinabove.

The TWO PHASE and FIRST-K predictors preferably are trained on and operate on features such as the following:

Locations of the 5' and/or 3' ends of the known diced miRNAs, which are preferably represented by their respective distances from the 5' end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor; and secondarily Metrics related to the nucleotide content of the diced miRNA and/or of the hairpin shaped miRNA precursor.

In accordance with an embodiment of the present invention scores of two or more of the abovementioned classifiers or predictors are integrated, yielding an integrated score for each "potential GAM RNA". As an example, FIG. 13C illustrates integration of scores from two classifiers, a 3' end recognition classifier and a 5' end recognition classifier, the scores of which are integrated to yield an integrated score. Most preferably, the INTEGRATED SCORE of FIG. 13C preferably implements a "best-of-breed" approach employing a pair of classifiers and accepting only "potential GAM RNAs" that score highly on one of the above mentioned "EDIT DISTANCE", or "TWO-PHASE" predictors. In this context, "high scores" means scores which have been demonstrated to have low false positive value when scoring known miRNA oligonucleotides. Alternatively, the INTEGRATED SCORE may be derived from operation of more or less than two classifiers.

The INTEGRATED SCORE is evaluated as follows: (a) the "potential GAM RNA" having the highest score is preferably taken to be the most probable GAM RNA, and (b) if the integrated score of this most probable GAM RNA is higher than a pre-defined threshold, then the most probable GAM RNA is accepted as a PREDICTED GAM RNA. Preferably, this evaluation technique is not limited to the highest scoring potential GAM RNA.

As a final optional stage we may filter PREDICTED GAM RNAs with low complexity, which have high probability to be part of repeated element in the DNA (for example ATATATA sequences). For each PREDICTED GAM RNA sequence we count the number of occurrences of each 2 nucleotides combination (AA, AT, AC), we filter out sequences where the sum of the most 2 probable combination is higher then 9. Using this criteria we filter 2% of the known miRNA and around 30% of the PREDICTED GAM RNAs.

Figure 14A:
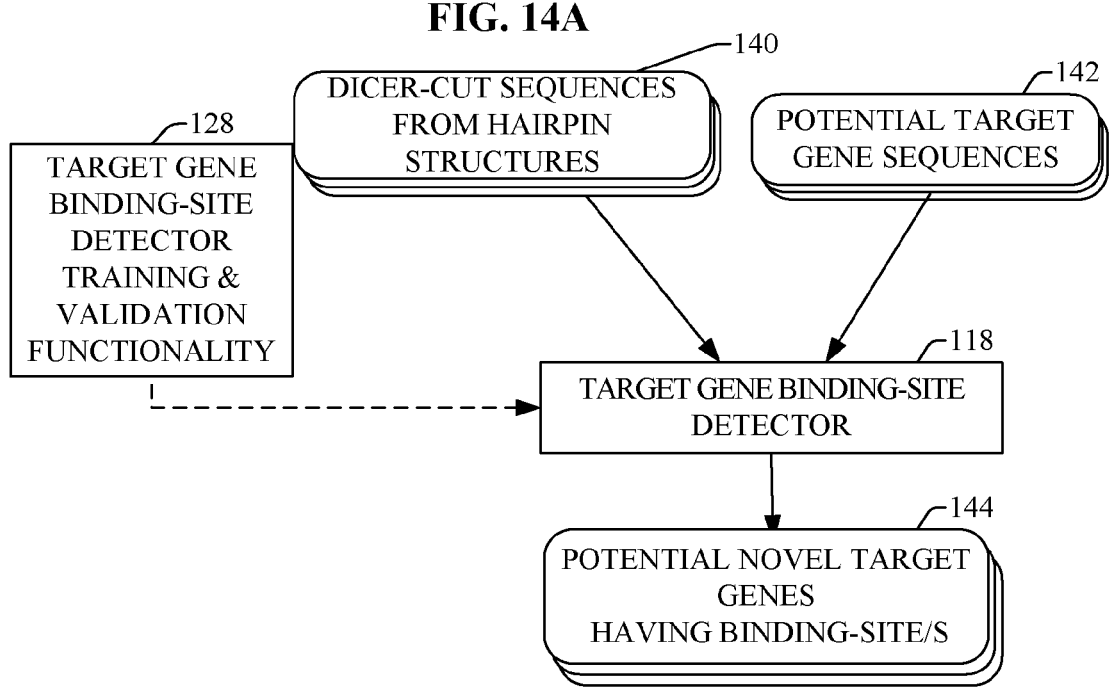
FIG. 14A is a simplified block diagram of a target gene binding-site detector constructed and operative in accordance with a preferred embodiment of the present invention.

Reference is now made to FIG. 14A which is a simplified block diagram of a preferred implementation of the TARGET GENE BINDING-SITE DETECTOR 118 described hereinabove with reference to FIG. 9. The goal of the TARGET GENE BINDING-SITE DETECTOR 118 is to detect one or more binding sites such as BINDING SITE I, BINDING SITE II and BINDING SITE III (FIG. 8) located in 3' untranslated regions of the mRNA of a known gene, the nucleotide sequence of which binding sites is partially or fully complementary to a GAM RNA, thereby determining that the above mentioned known gene is a target gene thereof.

The TARGET GENE BINDING-SITE DETECTOR 118 (FIG. 9) receives a plurality of DICER-CUT SEQUENCES FROM HAIRPIN STRUCTURES 140 (FIG. 13A), and a plurality of POTENTIAL TARGET GENE SEQUENCES 142 which are derived from SEQUENCED DNA DATA 104 (FIG. 9).

TARGET GENE BINDING-SITE DETECTOR TRAINING & VALIDATION FUNCTIONALITY 128 (FIG. 10) is operative to train the TARGET GENE BINDING-SITE DETECTOR 118 on known miRNAs and their respective target genes and to build a background model for evaluation of a P value for the TARGET GENE BINDING-SITE DETECTOR 118 results It Construct the model by analyzing both heuristically and computationally the results of the TARGET GENE BINDING-SITE DETECTOR 118.

Following operation of TARGET GENE BINDING-SITE DETECTOR TRAINING & VALIDATION FUNCTIONALITY 128 (FIG. 10), the TARGET GENE BINDING-SITE DETECTOR 118 is operative to detect a plurality of POTENTIAL NOVEL TARGET GENES HAVING BINDING-SITE/S 144 the nucleotide sequence of which is partially or fully complementary to that of each of the plurality of DICER-CUT SEQUENCES FROM HAIRPIN STRUCTURES 140. Preferred operation of the TARGET GENE BINDING-SITE DETECTOR 118 is further described hereinbelow with reference to FIG. 14B.

Figure 14B:
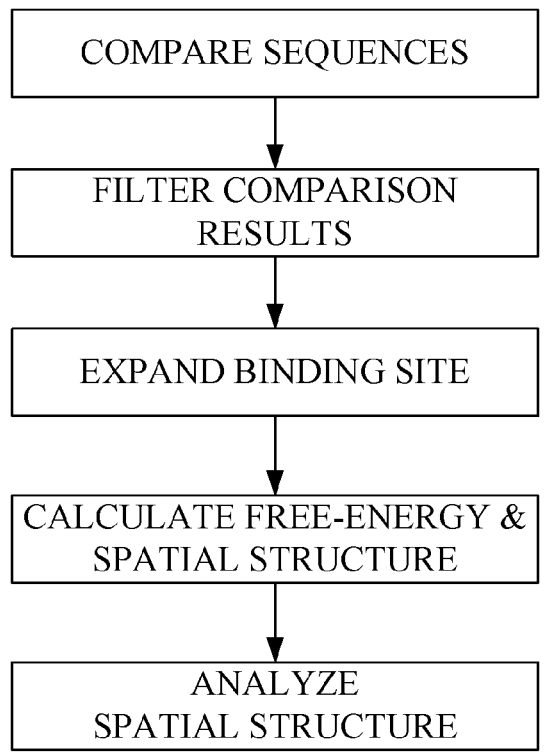
FIG. 14B is a simplified flowchart illustrating operation of a target gene binding-site detector constructed and operative in accordance with a preferred embodiment of the present invention.

Reference is now made to FIG. 14B which is a simplified flowchart illustrating a preferred operation of the TARGET GENE BINDING-SITE DETECTOR 118 of FIG. 9. In a preferred embodiment of the present invention, the TARGET GENE BINDING-SITE DETECTOR 118 employs a match search tool, described hereinbelow, in order to compare the nucleotide sequence of each of the plurality of DICER-CUT SEQUENCES FROM HAIRPIN STRUCTURES 140 (FIG. 13A), to the POTENTIAL TARGET GENE SEQUENCES 142 (FIG. 14A), such as 3 untranslated regions of known mRNAs, in order to find crude potential matches. Alternatively, a sequence comparison algorithm such as BLAST can be used.

The match search tool compare the DICER-CUT SEQUENCES FROM HAIRPIN STRUCTURES 140 (FIG. 14A) to POTENTIAL TARGET GENE SEQUENCES 142 (FIG. 14A). the methodology of the match search tool is to match Nucleotides 1:8 of DICER-CUT SEQUENCES FROM HAIRPIN STRUCTURES 140 (FIG. 14A) to POTENTIAL TARGET GENE SEQUENCES 142 (FIG. 14A). The results are preferably filtered to allow at most 1 edit distance between the DICER-CUT SEQUENCES FROM HAIRPIN STRUCTURES 140 (FIG. 14A) complementary sequence and POTENTIAL TARGET GENE SEQUENCES 142 (FIG. 14A).

In a preferred implementation of the match search tool, it first calculates two preprocess data structures: the first, store for every 9 nts sequences all its appearances in the POTENTIAL TARGET GENE SEQUENCES 142 (FIG. 14A).

The second is a map of all the 8 nts sequence to 9 nts sequences that can be accepted by adding one nucleotide and performing one or less editing actions to the 8 nts complementary sequence. This two data structures help to improve performance and to perform the binding site filtering stage as an integral part of the search. The match search tool in this implementation returns for every DICER-CUT SEQUENCES FROM HAIRPIN STRUCTURES 140 (FIG. 14A all the appearances of the 9 nts sequence in the POTENTIAL TARGET GENE SEQUENCES 142 (FIG. 14A) that are calculated using the second, describe hereinabove, data structure from its first 8 nts. The 9 nts sequences appearances are the potentially 3 of the POTENTIAL TARGET GENE SEQUENCES 142 (FIG. 14A) binding site of each DICER-CUT SEQUENCES FROM HAIRPIN STRUCTURES 140 (FIG. 14A Next the binding sites are expanded, and determinations are made whether if nucleotide sequences immediately upstream to the binding sites 3 part matches with the 3' end of the DICER-CUT SEQUENCES FROM HAIRPIN STRUCTURES. The alignment of the binding site 5 part is made by the alignment algorithm with specific weighting parameters describes hereinbelow with reference to FIG. 12). Alternatively the alignment can include also the 3 part of the binding site.

The alignment algorithm (implemented here) with specific weighting parameters. The weighting parameters are based on analyze of known miRNA binding sites (references: Wightman et al. Cell 1993, Moss Cell 1997, Reinhart Nature 2000, Abrahante Developmental Cell 2003 and Lin Developmental Cell 2003, Brennecke Cell 2003, Stark PLOS 2003, lewis et al. Cell 2003). It was heuristically found to best distinguish between known miRNA binding sites and sequences which are known not to be miRNA binding sites.

According to a preferred embodiment of the present invention a good matching at 5' end of the miRNA (nucleotides 1-8), and at 3' end of the miRNA, (the last 9 nucleotides) is required. The matching at 5' end is crucial for the binding while the 3' end binding is less important but can compensate on few mismatches at the 5'. The nucleotides at the middle of the miRNA have no punishment for any editing operation (reference: Doench et al. Gene and Development 2004). In this preferred embodiment the alignment of the 5 end of the miRNA (3 of the binding site) is a result of the match search tool, while the middle and 3 miRNA (5 of the binding site) is done by the alignment algorithm. The alignment is a combination of both. Alternatively, the alignment is done for all the miRNA and all the binding site sequence. The alignment algorithm finds the lowest free-energy spatial structure and heuristic constrain that were found to distinct the known binding sites in the best way. The alignment yields 2 scores for 5' end and 3' end. Each score represents the inverse of its probability to obtain such or higher score by running random sequences, with 22 nucleotides length and same base composition as known miRNA, with randomly chosen 3 un translated region sequences. The final score is the multiplicity of the two scores.

The binding site detector, then analyze the spatial structure of the miRNA with all its potential target gene 3 un translated region. It assesses the list of binding sites of each miRNA-Target gene pair with their positions and respective scores. The TARGET GENE BINDING-SITE DETECTOR 118 (FIG. 14A) then uses the fact that Many of the known binding sites are clustered, to evaluate the P value of obtaining cluster of few binding sites on the same target gene 3 un translated region in the following way: It scans different scores threshold, and calculate for each threshold the number and positions of possible binding sites with score above the threshold. It then gets from a preprocess calculated background matrixes, describe hereinbelow, a P value for each threshold and number and positions of binding sites combination. The output score for each miRNA and target gene pair is the minimal P value, normalized with the number of thresholds trying using Bernoulli distribution. A preference of low P value pairs is made.

As mentioned hereinabove, for each target gene a preprocess calculated background matrixes were build. The matrixes includes rows for each number of miRNA binding site (In the preferred embodiment the matrix include 7 rows for 0 to 6 binding site.), and columns for each different score threshold (In the preferred embodiment the matrix include 5 columns for 5 different threshold). Each matrix cell, corresponding to specific number of binding site and threshold, was set to be the probability to get equal or more binding sites with equal or more score by random sequences with 22 nucleotides length with the same letter distribution as known miRNAs (29.5% T, 24.5% A, 25% G and 21% C). Those probabilities are calculated by running the above procedure for 10000 random sequences. The P value can be estimated as the number of random sequences obeys the matrix cell requirement divided by the total number of random sequences (10000). In the preferred embodiment 2 matrixes are calculated. The P values are of the second matrix are calculated under constrain that at least two of the binding site position are under a heuristically determine constant value. The second matrix values are calculated without this constrain. The TARGET GENE BINDING-SITE DETECTOR uses the second matrix if the binding sites position agree with the constrain, else it uses the first. In an alternative embodiment only one matrix is calculated without any constrain on the binding sites positions.

Test preformed using the TARGET GENE BINDING-SITE DETECTOR showed that all of the known miRNA target genes are found using this algorithm with a P value of less than 0.5%. Running known miRNA against 3400 potential 3'UTR of target genes sequences yield on average 32 target genes for each miRNA with P value less than 0.5%, while background sequences, as well as inverse or complement sequence of known miRNA (which preserve their high order sequence statistics) found, as excepted, on average 17 target genes. This reflects the algorithm performance to detect real target genes with 47% accuracy.

Scoring of all potential binding sites are calculated and P value for obtaining such binding sites list for DICER-CUT SEQUENCE FROM HAIRPIN STRUCTURE and POTENTIAL TARGET GENE SEQUENCE pair is evaluate using the background matrix. In accordance with another preferred embodiment of the present invention, binding sites are searched by a reversed process. Sequences of K (preferably 22) nucleotides of a untranslated regions of a target gene are assessed as potential binding sites. A sequence comparison algorithm, such as BLAST or EDIT DISTANCE variant, is then used to search elsewhere in the genome for partially or fully complementary sequences which are found in known miRNA oligonucleotides or computationally predicted GAM oligonucleotides. Only complementary sequences, which meet predetermined spatial structure and free energy criteria as described hereinabove, are accepted. Clustered binding sites are strongly preferred and potential binding sites and potential GAM oligonucleotides which occur in evolutionarily conserved genomic sequences are also preferred. Scoring of candidate binding sites takes into account free energy and spatial structure of the binding site complexes, as well as the aforesaid preferences.

Figure 15:
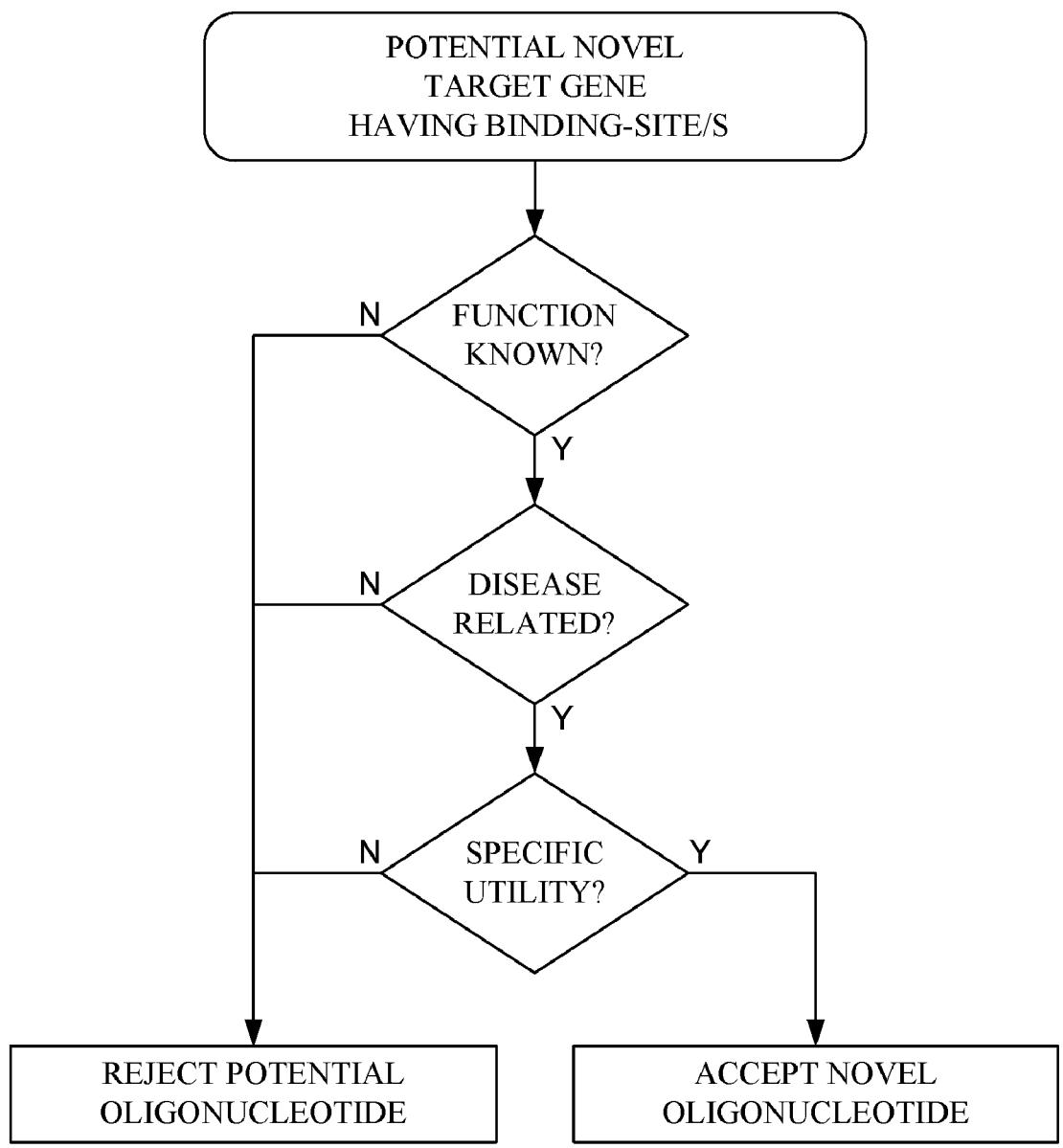
FIG. 15 is a simplified flowchart illustrating operation of a function & utility analyzer constructed and operative in accordance with a preferred embodiment of the present invention.

Reference is now made to FIG. 15 which is a simplified flowchart illustrating a preferred operation of the FUNCTION & UTILITY ANALYZER 120 described hereinabove with reference to FIG. 9. The goal of the FUNCTION & UTILITY ANALYZER 120 is to determine if a potential target gene is in fact a valid clinically useful target gene. Since a potential novel GAM oligonucleotide binding a binding site in the UTR of a target gene is understood to inhibit expression of that target gene, and if that target gene is shown to have a valid clinical utility, then in such a case it follows that the potential novel oligonucleotide itself also has a valid useful function which is the opposite of that of the target gene.

The FUNCTION & UTILITY ANALYZER 120 preferably receives as input a plurality of POTENTIAL NOVEL TARGET GENES HAVING BINDING-SITE/S 144 (FIG. 14A), generated by the TARGET GENE BINDING-SITE DETECTOR 118 (FIG. 9). Each potential oligonucleotide is evaluated as follows: First, the system checks to see if the function of the potential target gene is scientifically well established. Preferably, this can be achieved bioinformatically by searching various published data sources presenting information on known function of proteins. Many such data sources exist and are published as is well known in the art. Next, for those target genes the function of which is scientifically known and is well documented, the system then checks if scientific research data exists which links them to known diseases. For example, a preferred embodiment of the present invention utilizes the OMIM™ (Hamosh et al, 2002) database published by NCBI, which summarizes research publications relating to genes which have been shown to be associated with diseases. Finally, the specific possible utility of the target gene is evaluated. While this process too may be facilitated by bioinformatic means, it might require manual evaluation of published scientific research regarding the target gene, in order to determine the utility of the target gene to the diagnosis and or treatment of specific disease. Only potential novel oligonucleotides, the target genes of which have passed all three examinations, are accepted as novel oligonucleotide.

Figure 16:
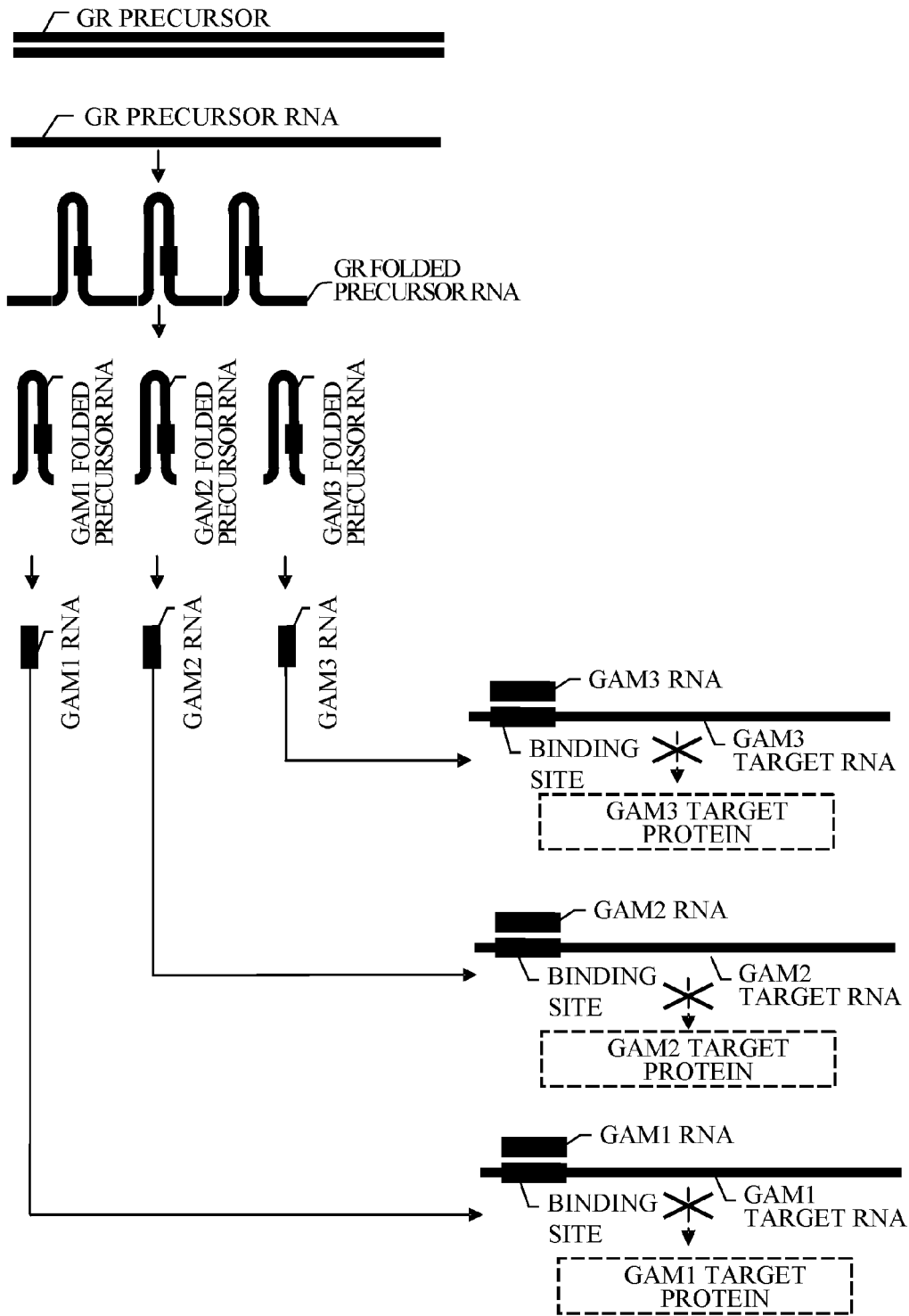
FIG. 16 is a simplified diagram describing a novel bioinformatically detected group of regulatory polynucleotides, referred to here as Genomic Record (GR) polynucleotides, each of which encodes an 'operon-like' cluster of novel miRNA-like oligonucleotides, which in turn modulate expression of one or more target genes.

Reference is now made to FIG. 16, which is a simplified diagram describing each of a plurality of novel bioinformatically detected regulatory polynucleotide referred to here as Genomic Record (GR) polynucleotide, which encodes an 'operon-like' cluster of novel microRNA-like oligonucleotides, each of which in turn modulates expression of at least one target gene; the function and utility of which at least one target gene is known in the art.

GR PRECURSOR is a novel bioinformatically detected regulatory, non protein coding polynucleotide. The method by which GR PRECURSOR is detected is described hereinabove with additional reference to FIGS. 9-18.

GR PRECURSOR encodes GR PRECURSOR RNA, an RNA molecule, typically several hundred to several thousand nucleotides long. GR PRECURSOR RNA folds spatially, forming GR FOLDED PRECURSOR RNA. It is appreciated that GR FOLDED PRECURSOR RNA comprises a plurality of what is known in the art as 'hairpin' structures. These 'hairpin' structures are due to the fact that the nucleotide sequence of GR PRECURSOR RNA comprises a plurality of segments, the first half of each such segment having a nucleotide sequence which is at least a partial or accurate reverse-complement sequence of the second half thereof, as is well known in the art.

GR FOLDED PRECURSOR RNA is naturally processed by cellular enzymatic activity into a plurality of separate GAM precursor RNAs, herein schematically represented by GAM1 FOLDED PRECURSOR RNA through GAM3 FOLDED PRECURSOR RNA, each of which GAM folded precursor RNAs being a hairpin shaped RNA segment, corresponding to GAM FOLDED PRECURSOR RNA of FIG. 8.

The above mentioned GAM folded precursor RNAs are diced by DICER COMPLEX of FIG. 8, yielding respective short RNA segments of about 22 nucleotides in length, schematically represented by GAM1 RNA through GAM3 RNA, each of which GAM RNAs corresponding to GAM RNA of FIG. 8. GAM1 RNA, GAM2 RNA and GAM3 RNA, each bind complementarily to binding sites located in untranslated regions of respective target genes, designated GAM1 TARGET RNA, GAM2 TARGET RNA and GAM3 TARGET RNA, respectively, which target binding site corresponds to a target binding site such as BINDING SITE I, BINDING SITE II or BINDING SITE III of FIG. 8. This binding inhibits translation of the respective target proteins designated GAM1 TARGET PROTEIN, GAM2 TARGET PROTEIN and GAM3 TARGET PROTEIN respectively.

It is appreciated that specific functions, and accordingly utilities of GR polynucleotide are correlated with and may be deduced from the identity of the target genes, which are inhibited by GAM RNAs comprised in the 'operon-like' cluster of GR polynucleotide, schematically represented by GAM1 TARGET PROTEIN through GAM3 TARGET PROTEIN. The function of these target genes is elaborated in Table 8, hereby incorporated herein.

Figure 17:
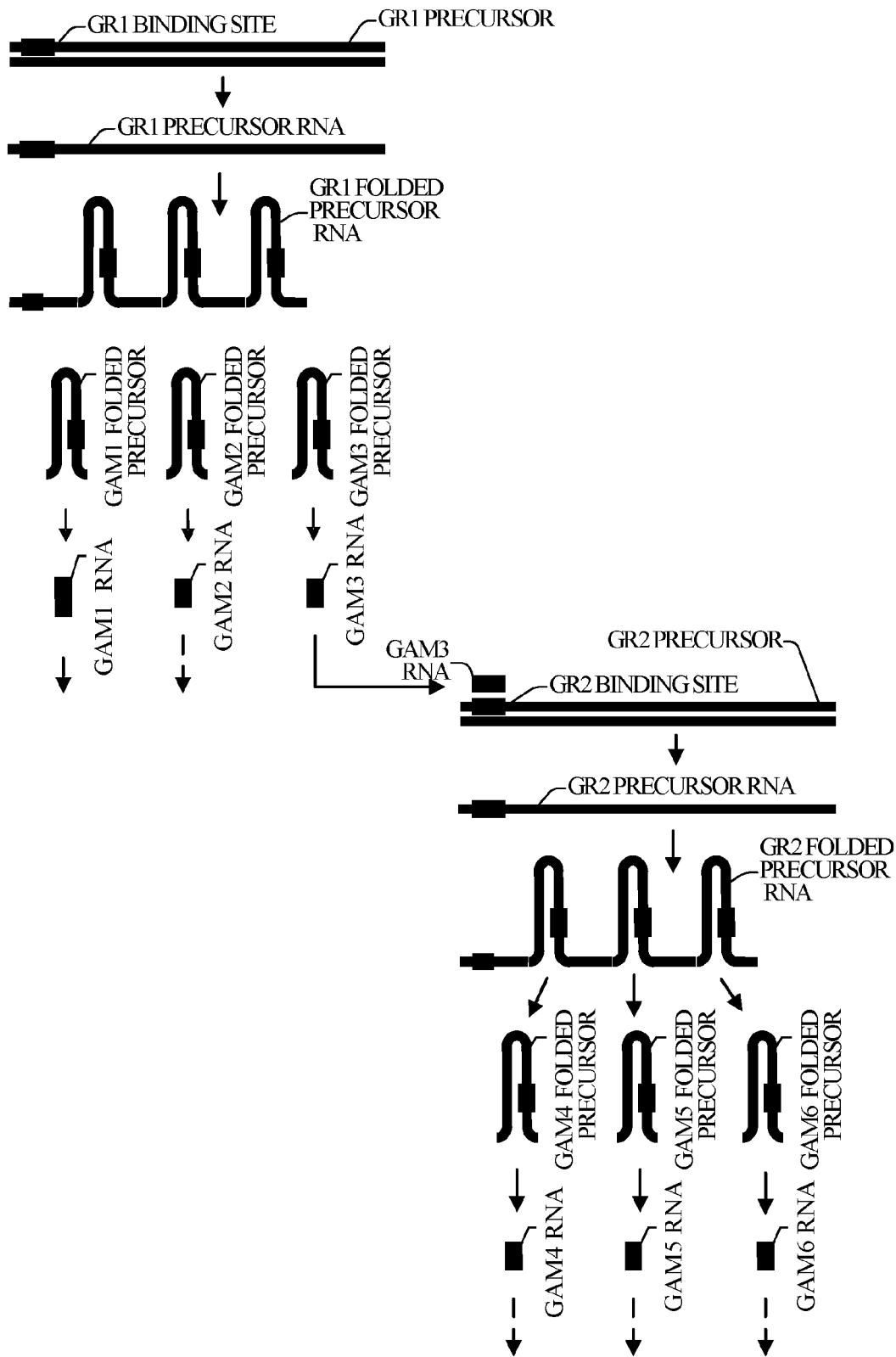
FIG. 17 is a simplified diagram illustrating a mode by which human oligonucleotides of a novel group of operon-like polynucleotides of the present invention, modulate expression of other such polynucleotides, in a cascading manner.

Reference is now made to FIG. 17 which is a simplified diagram illustrating a mode by which oligonucleotides of a novel group of operon-like polynucleotide described hereinabove with reference to FIG. 16 of the present invention, modulate expression of other such polynucleotide, in a cascading manner. GR1 PRECURSOR and GR2 PRECURSOR are two polynucleotides of the novel group of operon-like polynucleotides designated GR PRECURSOR (FIG. 16). As is typical of polynucleotides of the GR group of polynucleotides GR1 PRECURSOR and GR2 PRECURSOR, each encode a long RNA precursor, which in turn folds into a folded RNA precursor comprising multiple hairpin shapes, and is cut into respective separate hairpin shaped RNA segments, each of which RNA segments being diced to yield an oligonucleotide of a group of oligonucleotides designated GAM RNA. In this manner GR1 yields GAM1 RNA, GAM2 RNA and GAM3 RNA, and GR2 yields GAM4 RNA, GAM5 RNA and GAM6 RNA. As FIG. 17 shows, GAM3 RNA, which derives from GR1, binds a binding site located adjacent to GR2 GPRECURSOR thus modulating expression of GR2, thereby invoking expression of GAM4 RNA, GAM5 RNA and GAM6 RNA which derive from GR2. It is appreciated that the mode of modulation of expression presented by FIG. 17 enables an unlimited 'cascading effect' in which a GR polynucleotide comprises multiple GAM oligonucleotides each of which may modulate expression of other GR polynucleotides each such GR polynucleotides comprising additional GAM oligonucleotide etc., whereby eventually certain GAM oligonucleotides modulate expression of target proteins.

This mechanism is in accord with the conceptual model of the present invention addressing the differentiation enigma, described hereinabove with specific reference to FIGS. 6-7.

Figure 18:
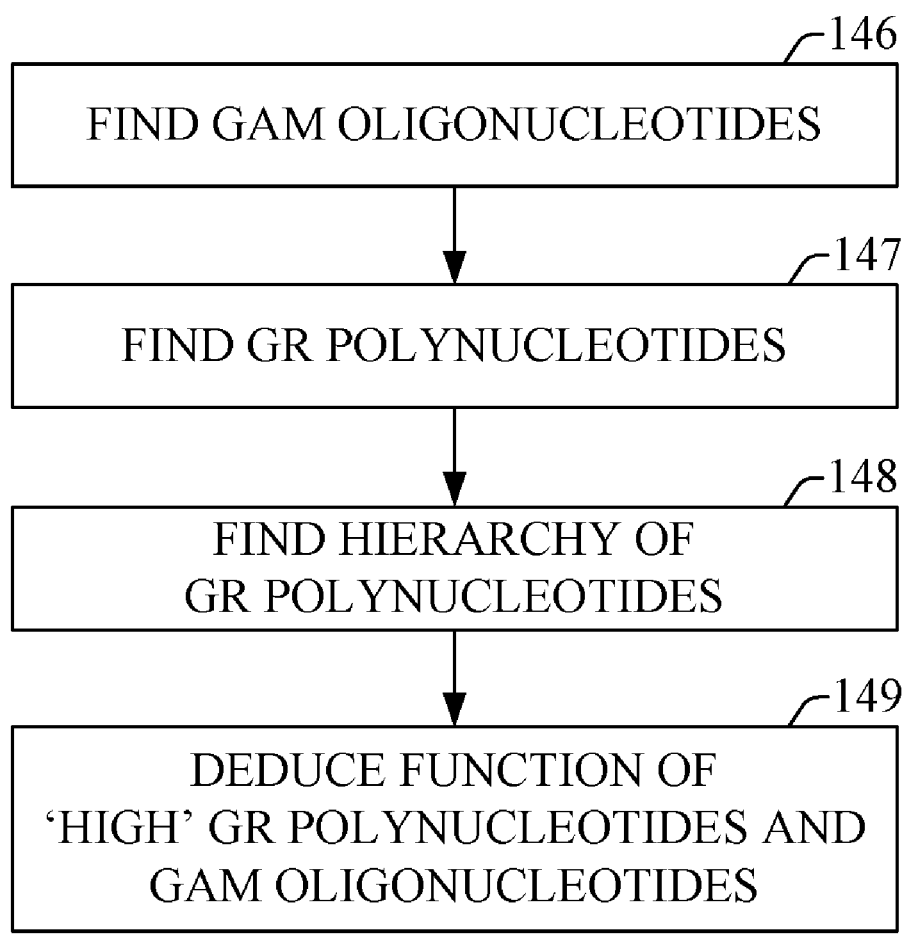
FIG. 18 is a block diagram illustrating an overview of a methodology for finding novel human oligonucleotides and novel operon-like human polynucleotides of the present invention, and their respective functions.

Reference is now made to FIG. 18 which is a block diagram illustrating an overview of a methodology for finding novel oligonucleotides and operon-like polynucleotides of the present invention, and their respective functions. According to a preferred embodiment of the present invention, the methodology to finding novel oligonucleotides of the present invention and their function comprises of the following major steps: First, FIND GAM OLIGONUCLEOTIDES 146 is used to detect, oligonucleotide of the novel group of oligonucleotide of the present invention, referred to here as GAM oligonucleotide. GAM oligonucleotides are located and their function elicited by detecting target proteins they bind and the function of those target proteins, as described hereinabove with reference to FIGS. 9-15. Next, FIND GR POLYNUCLEOTIDES 147 is used to detect polynucleotide of a novel group of operon-like polynucleotide of the present invention, referred to here as GR polynucleotide. GR polynucleotides are located, by locating clusters of proximally located GAM oligonucleotide, based on the previous step. Consequently, FIND HIERARCHY OF GR POLYNUCLEOTIDES 148 elicits the hierarchy of GR and GAM: binding sites for non-protein-binding GAM oligonucleotide comprised in each GR polynucleotide found are sought adjacent to other GR polynucleotides. When found, such a binding site indicates that the connection between the GAM and the GR the expression of which it modulates, and thus the hierarchy of the GR polynucleotides and the GAM oligonucleotides they comprise.

Lastly, DEDUCE FUNCTION OF HIGH GR POLYNUCLEOTIDES AND GAM OLIGONUCLEOTIDES 149 is used to deduce the function of GR polynucleotides and GAM oligonucleotides which are 'high' in the hierarchy, i.e. GAM oligonucleotides which modulate expression of other GR polynucleotides rather than directly modulating expression of target proteins. A preferred approach is as follows: The function of protein-modulating GAM oligonucleotides is deducible from the proteins which they modulate, provided that the function of these target proteins is known. The function of 'higher' GAM oligonucleotides may be deduced by comparing the function of protein-modulating GAM oligonucleotides with the hierarchical relationships by which the 'higher' GAM oligonucleotides are connected to the protein-modulating GAM oligonucleotides. For example, given a group of several protein-modulating GAM oligonucleotides which collectively cause a protein expression pattern typical of a certain cell-type, then a 'higher' GAM oligonucleotide is sought which modulates expression of GR polynucleotides which perhaps modulate expression of other GR polynucleotides which eventually modulate expression of the given group of protein-modulating GAM oligonucleotide. The 'higher' GAM oligonucleotide found in this manner is taken to be responsible for differentiation of that cell-type, as per the conceptual model of the invention described hereinabove with reference to FIG. 6.

Figure 19:
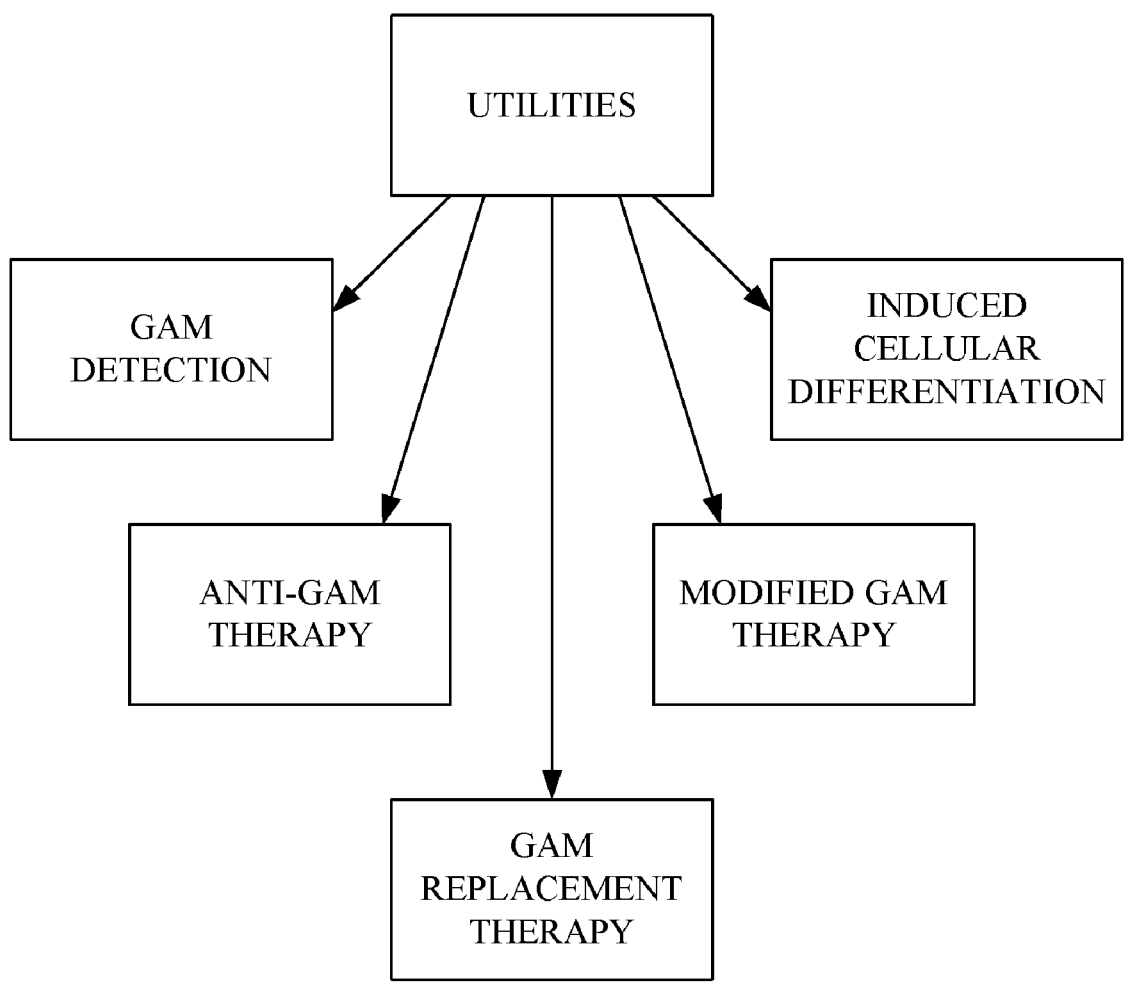
FIG. 19 is a block diagram illustrating different utilities of novel oligonucleotides and novel operon-like polynucleotides, both of the present invention.

Reference is now made to FIG. 19 which is a block diagram illustrating different utilities of oligonucleotide of the novel group of oligonucleotides of the present invention referred to here as GAM oligonucleotides and GR polynucleotides. The present invention discloses a first plurality of novel oligonucleotides referred to here as GAM oligonucleotides and a second plurality of operon-like polynucleotides referred to here as GR polynucleotides, each of the GR polynucleotide encoding a plurality of GAM oligonucleotides. The present invention further discloses a very large number of known target genes, which are bound by, and the expression of which is modulated by each of the novel oligonucleotides of the present invention. Published scientific data referenced by the present invention provides specific, substantial, and credible evidence that the above mentioned target genes modulated by novel oligonucleotides of the present invention, are associated with various diseases. Specific novel oligonucleotides of the present invention, target genes thereof and diseases associated therewith, are described hereinbelow with reference to Tables 1 through 11. It is therefore appreciated that a function of GAM oligonucleotides and GR polynucleotides of the present invention is modulation of expression of target genes related to known diseases, and that therefore utilities of novel oligonucleotides of the present invention include diagnosis and treatment of the above mentioned diseases.

FIG. 19 describes various types of diagnostic and therapeutic utilities of novel oligonucleotides of the present invention. A utility of novel oligonucleotide of the present invention is detection of GAM oligonucleotides and of GR polynucleotides. It is appreciated that since GAM oligonucleotides and GR polynucleotides modulate expression of disease related target genes, that detection of expression of GAM oligonucleotides in clinical scenarios associated with said diseases is a specific, substantial and credible utility. Diagnosis of novel oligonucleotides of the present invention may preferably be implemented by RNA expression detection techniques, including but not limited to biochips, as is well known in the art. Diagnosis of expression of oligonucleotides of the present invention may be useful for research purposes, in order to further understand the connection between the novel oligonucleotides of the present invention and the above mentioned related diseases, for disease diagnosis and prevention purposes, and for monitoring disease progress.

Another utility of novel oligonucleotides of the present invention is anti-GAM therapy, a mode of therapy which allows up regulation of a disease-related target gene of a novel GAM oligonucleotide of the present invention, by lowering levels of the novel GAM oligonucleotide which naturally inhibits expression of that target gene. This mode of therapy is particularly useful with respect to target genes which have been shown to be under-expressed in association with a specific disease. Anti-GAM therapy is further discussed hereinbelow with reference to FIGS. 20A and 20B.

A further utility of novel oligonucleotides of the present invention is GAM replacement therapy, a mode of therapy which achieves down regulation of a disease related target gene of a novel GAM oligonucleotide of the present invention, by raising levels of the GAM which naturally inhibits expression of that target gene. This mode of therapy is particularly useful with respect to target genes which have been shown to be over-expressed in association with a specific disease. GAM replacement therapy involves introduction of supplementary GAM products into a cell, or stimulation of a cell to produce excess GAM products. GAM replacement therapy may preferably be achieved by transfecting cells with an artificial DNA molecule encoding a GAM which causes the cells to produce the GAM product, as is well known in the art.

Yet a further utility of novel oligonucleotides of the present invention is modified GAM therapy. Disease conditions are likely to exist, in which a mutation in a binding site of a GAM RNA prevents natural GAM RNA to effectively bind inhibit a disease related target gene, causing up regulation of that target gene, and thereby contributing to the disease pathology. In such conditions, a modified GAM oligonucleotides is designed which effectively binds the mutated GAM binding site, i.e. is an effective anti-sense of the mutated GAM binding site, and is introduced in disease effected cells. Modified GAM therapy is preferably achieved by transfecting cells with an artificial DNA molecule encoding the modified GAM which causes the cells to produce the modified GAM product, as is well known in the art.

An additional utility of novel GAM of the present invention is induced cellular differentiation therapy. An aspect of the present invention is finding oligonucleotides which determine cellular differentiation, as described hereinabove with reference to FIG. 18. Induced cellular differentiation therapy comprises transfection of cell with such GAM oligonucleotides thereby determining their differentiation as desired. It is appreciated that this approach may be widely applicable, inter alia as a means for auto trans-plantation harvesting cells of one cell-type from a patient, modifying their differentiation as desired, and then trans-planting them back into the patient. It is further appreciated that this approach may also be utilized to modify cell differentiation in vivo, by transfecting cells in a genetically diseased tissue with a cell-differentiation determining GAM thus stimulating these cells to differentiate appropriately.

Reference is now made to FIGS. 20A and 20B, simplified diagrams which when taken together illustrate anti-GAM therapy mentioned hereinabove with reference to FIG. 19. A utility of novel GAMs of the present invention is anti-GAM therapy, a mode of therapy which allows up regulation of a disease-related target gene of a novel GAM of the present invention, by lowering levels of the novel GAM which naturally inhibits expression of that target gene. FIG. 20A shows a normal GAM inhibiting translation of a target gene by binding of GAM RNA to a BINDING SITE found in an untranslated region of GAM TARGET RNA, as described hereinabove with reference to FIG. 8.

FIG. 20B shows an example of anti-GAM therapy. ANTI-GAM RNA is short artificial RNA molecule the sequence of which is an anti-sense of GAM RNA. Anti-GAM treatment comprises transfecting diseased cells with ANTI-GAM RNA, or with a DNA encoding thereof. The ANTI-GAM RNA binds the natural GAM RNA, thereby preventing binding of natural GAM RNA to its BINDING SITE. This prevents natural translation inhibition of GAM TARGET RNA by GAM RNA, thereby up regulating expression of GAM TARGET PROTEIN.

It is appreciated that anti-GAM therapy is particularly useful with respect to target genes which have been shown to be under-expressed in association with a specific disease.

Furthermore, anti-GAM therapy is particularly useful, since it may be used in situations in which technologies known in the art as RNAi and siRNA can not be utilized. As in known in the art, RNAi and siRNA are technologies which offer means for artificially inhibiting expression of a target protein, by artificially designed short RNA segments which bind complementarily to mRNA of said target protein. However, RNAi and siRNA can not be used to directly up regulate translation of target proteins.

Figure 21A:
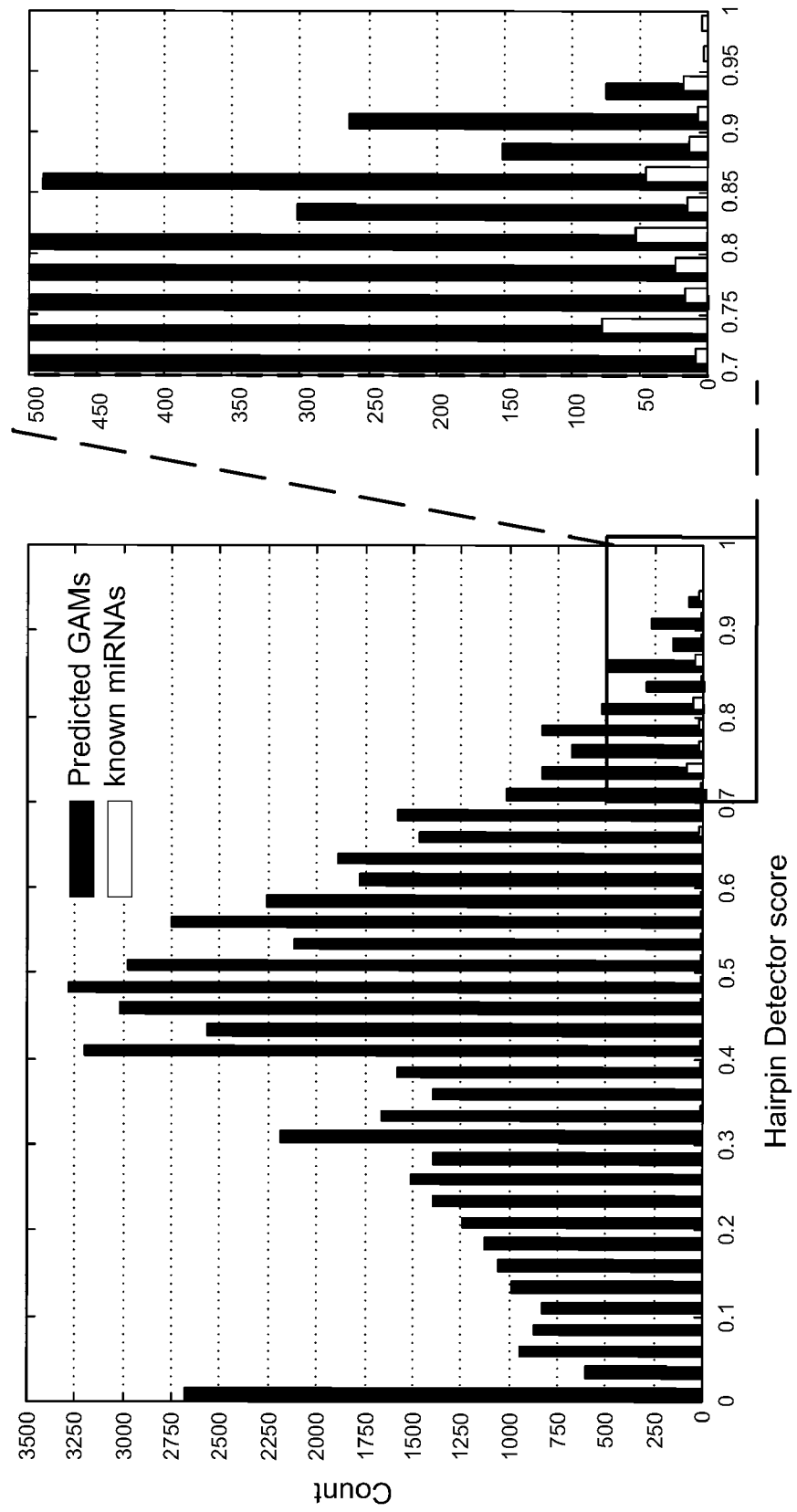
FIG. 21A is a histogram representing the distribution of known miRNA oligonucleotides and that of predicted miRNA-like hairpin structures extracted from expressed genome sequences with respect to their hairpin detector score.

Reference is now made to FIG. 21A, which is a histogram representing the distribution of known miRNA oligonucleotides and that of hairpin structures extracted from expressed human genome sequences with respect to their HAIRPIN DETECTOR score (this analysis preferably uses the previous version of the Hairpin Detector program). The known miRNA oligonucleotides set is taken from RFAM database, Release 2.1 and includes 440 miRNA oligonucleotides from *H. sapienas, M. musculus, C. elegans, C. brigassae* and *D. melanogaster*. Folding of expressed genome sequences taken from public databases of ESTs (Unigene-NCBI and TIGR) identified 342,882 hairpin structures. ~154,000 out of the 342,882 hairpin structures did not pass the filter of being identified as hairpins in several secondary structure folding versions of the given genomic sequence, as described hereinabove with reference to FIG. 12B, and hence did not receive a Hairpin detector score. Furthermore, ~133,000 hairpin structures did not pass the filter of minimum score of the DICER-CUT LOCATION DETECTOR 116 (FIG. 9) (those ~287,000 hairpin structures are not represented in the histogram).

Hairpin structures are considered as miRNA-like precursor oligonucleotides here referred to as GAM precursor, if their Hairpin detector score is above 0.3. Thus, the GAM precursor set is comprised of ~40,000 hairpin structures, of those ~5100 received a high Hairpin detector score (>=0.7). These are much higher numbers than those of the known miRNA oligonucleotides and of the upper bound of ~255 human miRNA oligonucleotides, estimated by Bartel et al. (Science, 299, 1540, March 2003). Of the reference set that pass the above filter (408/440), 284 (69%) received a high Hairpin detector score (>=0.7).

Reference is now made to FIG. 21B, which is a table summarizing laboratory validation results that validate efficacy of the BIOINFORMATIC OLIGONUCLEOTIDE DETECTION ENGINE 100 (FIG. 9). In order to assess efficacy of the BIOINFORMATIC OLIGONUCLEOTIDE DETECTION ENGINE 100, novel oligonucleotides predicted thereby are preferably filtered using the scores of HAIRPIN DETECTOR 114 (FIG. 9) and DICER-CUT LOCATION DETECTOR 116 (FIG. 9) as follows: covering 85% (second column) of published hairpin our algorithm enable to filter 95% of background (third column), leaving only dozens of predicted hairpins with relatively high probability of being a real hairpin carrying a 'diced' miRNA for lab validation.

Group A (selected for the present invention, first column): The score of the HAIRPIN-DETECTOR is above 0, the overall score of the two-phased predictor is above 0.55, and the score of the second phase of the two-phased predictor is above 0.75, or the score of the EDIT-DISTANCE predictor is equal or above 17. In this group, one Dicer cut location is predicted for each hairpin.

Sample of novel bioinformatically predicted human GAMs are sent to the laboratory for validation (fourth column), and the number (fifth column) and percent (sixth column) of successful validation of predicted human GAM is noted for each of the groups, as well as overall (bottom line). The information about the above lab validation is based on previous patents group selections, there is a high correlation between the old group A predicted hairpin and the present one indicate that the update results should be approximately the same or better, due to improvement in the predictions.

It is appreciated that the present invention comprises 15454 novel GAM oligonucleotides, which fall into group A, and that the BIOINFORMATIC OLIGONUCLEOTIDE DETECTION ENGINE 100 (FIG. 9) is substantiated by a group of 37 novel human GAM oligonucleotides validated by laboratory means, out of 101 human GAM oligonucleotides which were tested in the lab, resulting in validation of an overall 31% accuracy. The selected group demonstrated 37% accuracy. Pictures of test-results of specific human GAM oligonucleotides as well as the methodology used for validating the expression of predicted oligonucleotides are elaborated hereinbelow with reference to FIG. 22.

It is further appreciated that failure to detect a predicted oligonucleotide in the lab does not necessarily indicate a mistaken bioinformatic prediction. Rather, it may be due to technical sensitivity limitation of the lab test, or because the predicted oligonucleotides are not expressed in the tissue examined, or at the development phase tested.

It is still further appreciated that in general these findings are in agreement with the expected bioinformatic accuracy, as describe hereinabove with reference to FIG. 13B: assuming 80% accuracy of the HAIRPIN DETECTOR 114 and 80% accuracy of the DICER-CUT LOCATION DETECTOR 116 and 80% accuracy of the lab validation, this would result in 50% overall accuracy of the predicted oligonucleotide validated in the lab.

Figure 22A:
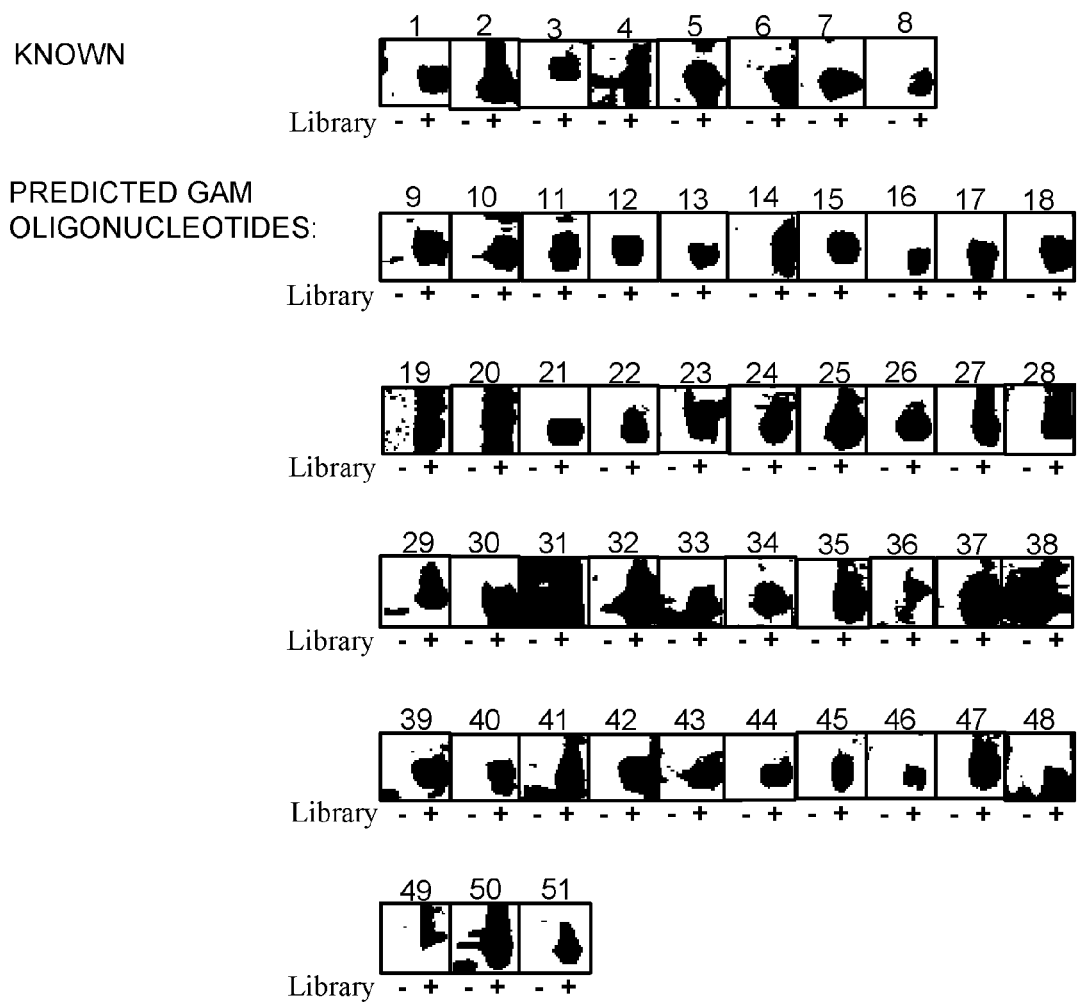

Reference is now made to FIG. 22A which is a picture of laboratory results validating the expression of 43 novel human GAM oligonucleotides detected by the BIOINFORMATIC OLIGONUCLEOTIDE DETECTION ENGINE 100 (FIG. 9).

Reference is now made to FIG. 22A and FIG. 22B which are pictures and a summary table of laboratory results validating the expression of 43 novel human GAM oligonucleotides detected by the BIOINFORMATIC OLIGONUCLEOTIDE DETECTION ENGINE 100. In each row in FIG. 22A, pictures of several oligonucleotides validated by hybridization of Polymerase Chain Reaction (PCR)-product southern-blots, are provided, each corresponding to a specific GAM oligonucleotide, as elaborated hereinbelow. To test our validation method, we used a reference set of 8 known human miRNA oligonucleotides, as a blind test to our laboratory. These PCR-product hybridization pictures are designated 1 through 8 for the reference set known miRNA oligonucleotides; and 9 through 51 for predicted GAM oligonucleotides.

In each PCR hybridization picture, 2 lanes are seen: the test lane, designated "+" and the control lane, designated "−". The control reaction contained all the components of the test reaction except library template. For convenience of viewing the results, all PCR-product hybridization pictures of FIG. 22A have been shrunk ×4 vertically. It is appreciated that for each of the tested GAM oligonucleotides a clear hybridization band appears in the test ("+") lane, but not in the control ("−") lane.

Specifically, FIG. 22A shows pictures of PCR-product hybridization validation by southern-blot, the methodology of which is described hereinbelow, to the following novel human GAM oligonucleotides (RosettaGenomics Ltd. Nomenclature, 'A' and 'B' referred to the Dicer Cut Location as described hereinbelow with reference to the description of large tables:

(1) hsa-MIR-21; (2) hsa-MIR-27b; (3) hsa-MIR-186; (4) hsa-MIR-93; (5) hsa-MIR-26a; (6) hsa-MIR-191; (7) hsa-MIR-31; (8) hsa-MIR-92; (9) GAM3418-A (later published by other researchers as hsa-MIR23); (10) GAM4426-A; (11) GAM281-A; (12) GAM7553-A; (13) GAM5385-A; (14) GAM2608-A; (15) GAM1032-A; (16) GAM3431-A; (17) GAM7933-A; (18) GAM3298-A.; (19) GAM7080-A; (20) GAM895-A.; (21) GAM3770.1; (22) GAM337162-A; (23) GAM 8678-A; (24) GAM2033-A; (25) GAM7776-A; (26) GAM8145-A; (27) GAM25-A; (28) GAM7352.1; (29) GAM337624-A; (30) GAM1479-A; (31) GAM2270-A; (32) GAM7591-A; (33) GAM8285-A; (34) GAM6773-A; (35) GAM336818-A; (36) GAM336487-A; (37) GAM337620-A; (38) GAM336809-A; (39) GAM5346-A; (40) GAM8554-A; (41) GAM2071-A; (42) GAM7957-A; (43) GAM391-A; (44) GAM6633-A; (45) GAM19; (46) GAM8358-A; (47) GAM3229-A; an)GAM 7052-A; (49) GAM3027-A; (50) GAM21 and (51) GAM oligonucleotide similar to mmu-MIR-30e.

The next validated GAM oligonucleotides are highly similar or identical to known mouse-miRNA oligonucleotides: GAM3027-A, similar to mmu-MIR-29c; GAM21, similar to mmu-MIR-130b; and GAM oligonucleotide which is highly similar to mmu-MIR-30e (picture number 51). In addition to the PCR—product hybridization detection, the following GAMs were also cloned and sequenced: GAM3418-A, GAM5385-A, GAM1032-A, GAM3298-A, GAM7080-A, GAM1338-A, GAM7776-A, GAM25-A, GAM337624-A, GAM1479-A, GAM6773-A, GAM336818-A, GAM336487-A, GAM337620-A, GAM336809-A, GAM3027-A, GAM21, and GAM oligonucleotide similar to mmu-MIR-30e (picture number 51). Furthermore, the following GAM oligonucleotides were sequenced directly from the ligation reaction by the method described hereinbelow under LIGATION-PCR DIAGNOSTIC METHOD: GAM4426-A, GAM7553-A, GAM2270-A, and GAM7591-A.

In order to validate the expression of predicted novel GAMs and assuming that these novel GAM oligonucleotides are probably expressed at low concentrations, a PCR product cloning approach was set up through the following strategy: two types of cDNA libraries designated "One tailed" and "Ligation" were prepared from frozen HeLa S100 extract (4c Biotech, Belgium) size fractionated RNA. Essentially, Total S100 RNA was prepared through an SDS-Proteinase K incubation followed by an acid Phenol-Chloroform purification and Isopropanol precipitation. Alternatively, total HeLa RNA was also used as starting material for these libraries.

Fractionation was done by loading up to 500 g per YM100 Amicon Microcon column (Millipore) followed by a 500 g centrifugation for 40 minutes at 4 C. Flow through "YM100"RNA consisting of about of the total RNA was used for library preparation or fractionated further by loading onto a YM30 Amicon Microcon column (Millipore) followed by a 13,500 g centrifugation for 25 minutes at 4 C. Flowthrough "YM30" was used for library preparation as is and consists of less than 0.5% of total RNA. For the both the "ligation" and the "One-tailed" libraries, RNA was dephosphorilated and ligated to an RNA (lowercase)-DNA (UPPERCASE) hybrid 5-phosphorilated, 3 idT blocked 3-adapter (5-P-uuuAACCG-CATCCTTCTC-idT-3 Dharmacon #P-002045-01-05) (SEQ ID NO: 2254574) (as elaborated in Elbashir et al., Genes Dev. 15:188-200 (2001)) resulting in ligation only of RNase III type cleavage products. 3-Ligated RNA was excised and purified from a half 6%, half 13% polyacrylamide gel to remove excess adapter with a Nanosep 0.2M centrifugal device (Pall) according to instructions, and precipitated with glycogenand 3 volumes of Ethanol. Pellet was resuspended in a minimal volume of water.

For the "ligation" library a DNA (JPPERCASE)-RNA Oowercase) hybrid 5-adapter (5-TACTAATACGACTCAC-Taaa-3 Dharmacon #P-002046-01-05) (SEQ ID NO: 2254575) was ligated to the 3-adapted RNA, reverse transcribed with "EcoRI-RT": (5-GACTAGCTGGAATTCAAG-GATGCGGTTAAA-3) (SEQ ID NO: 2254576), PCR amplified with two external primers essentially as in Elbashir et al 2001 except that primers were "EcoRI-RT" and "PstI Fwd" (5-CAGCCAACGCTGCAGATACGACTCACTAAA-3) (SEQ ID NO: 2254577). This PCR product was used as a template for a second round of PCR with one hemispecific and one external primer or with two hemispecific primers.

For the "One tailed" library the 3-Adapted RNA was annealed to 20 pmol primer "EcoRI RT" by heating to 70 C and cooling 0.1 C/sec to 30 C and then reverse transcribed with Superscript II RT (According to instructions, Invitrogen) in a 201 volume for 10 alternating 5 minute cycles of 37 C and 45 C. Subsequently, RNA was digested with 1 1 2M NaOH, 2 mM EDTA at 65 C for 10 minutes. cDNA was loaded on a polyacrylamide gel, excised and gelpurified from excess primer as above (invisible, judged by primer run alongside) and resuspended in 13 1 of water. Purified cDNA was then oligo-dC tailed with 400 U of recombinant terminal transferase (Roche molecular biochemicals), 1 1 100M dCTP, 1 1 15 mM CoCl2, and 41 reaction buffer, to a final volume of 20 l for 15 minutes at 37 C. Reaction was stopped with 210.2M EDTA and 15 1 3M NaOAc pH 5.2. Volume was adjusted to 150 1 with water, Phenol: Bromochloropropane 10:1 extracted and subsequently precipitated with glycogen and 3 volumes of Ethanol. C-tailed cDNA was used as a template for PCR with the external primers "T3-PstBsg(G/I) 18"(5- AATTAACCCTCACTAAAGGCTGCAGGTGC AGGIGGGIIGGGIIGGGIIGN-3 (SEQ ID NO: 2254578) where I stands for Inosine and N for any of the 4 possible. deoxynucleotides), and with "EcoRI Nested" (5-GGAAT-TCAAGGATGCGGTTA-3) (SEQ ID NO:2254579). This PCR product was used as a template for a second round of PCR with one hemispecific and one external primer or with two hemispecific primers.

Hemispecific primers were constructed for each predicted GAM RNA oligonucleotide by an in-house program designed to choose about half of the 5 or 3 sequence of the GAM RNA corresponding to a TM of about 30-34 C constrained by an optimized 3 clamp, appended to the cloning adapter sequence (for "One-tailed" libraries 5-GGN-NGGGNNG (SEQ ID NO: 2254580) on the 5 end of the GAM RNA, or TTTAACCGCATC-3 (SEQ ID NO: 2254581) on the 3 end of the GAM RNA. For "Ligation" libraries the same 3 adapter and 5-CGACTCACTAAA (SEQ ID NO: 2254582) on the 5 end). Consequently, a fully complementary primer of a TM higher than 60 C was created covering only one half of the GAM RNA sequence permitting the unbiased elucidation by sequencing of the other half.

Confirmation of GAM Oligonucleotide Sequence Authenticity of PCR Products:

SOUTHERN BLOT: PCR-product sequences were confirmed by southern blot (Southern E. M., Biotechnology, 1992, 24:122-39 (1975)) and hybridization with DNA oligonucleotide probes synthesized as complimentary (antisense) to predicted GAM RNA oligonucleotides. Gels were transferred onto a Biodyne PLUS 0.45 m, (Pall) positively charged nylon membrane and UV cross-linked. Hybridization was performed overnight with DIG-labeled probes at 420 C in DIG Easy-Hyb buffer (Roche). Membranes were washed twice with 2×SSC and 0.1% SDS for 10 minutes at 420 C and then washed twice with 0.5×SSC and 0.1% SDS for 5 min at 420 C. The membrane was then developed by using a DIG luminescent detection kit (Roche) using anti-DIG and CSPD reaction, according to the manufacturer's protocol. All probes were prepared according to the manufacturers (Roche Molecular Biochemicals) protocols: Digoxigenin (DIG) labeled antisense transcripts was prepared from purified PCR products using a DIG RNA labeling kit with T3 RNA polymerase. DIG labeled PCR was prepared by using a DIG PCR labeling kit. 3-DIG-tailed oligo ssDNA antisense probes, containing DIG-dUTP and dATP at an average tail length of 50 nucleotides were prepared from 100 pmole oligonucleotides with the DIG Oligonucleotide Labeling Kit.

CLONE-SEQUENCING: PCR products were inserted into pGEM-T (Promega) or pTZ57/T (MBI Fermentas), heat-shock transformed into competent JM109 E. coli (Promega) and sown on LB-Ampiccilin plates with IPTG and Xgal. White and light-blue colonies were transferred to duplicate gridded plates, one of which was blotted onto a membrane (Biodyne Plus, Pall) for hybridization with DIG tailed oligo probes (according to instructions, Roche) complimentary to the expected GAM. Plasmid DNA from positive colonies was sequenced.

LIGATION-PCR DIAGNOSTIC METHOD: To further validate predicted GAM PCR product sequence derived from hemi-primers, a PCR based diagnostic technique was devised to amplify only those products containing also at least two additional nucleotides of the non hemi-primer defined part of the predicted GAM RNA oligonucleotide. In essence, a diagnostic primer was designed so that its 3 end, which is the specificity determining side, was identical to the desired GAM RNA oligonucleotide, 2-10 nucleotides (typically 4-7, chosen for maximum specificity) further into its 3 end than the nucleotide stretch primed by the hemi-primer. The hemi-primer PCR product was first ligated into a T-cloning vector (pTZ57/T or pGEM-T) as described hereinabove. The ligation reaction mixture was used as template for the diagnostic PCR under strict annealing conditions with the new diagnostic primer in conjunction with a general plasmid-homologous primer, resulting in a distinct ~200 base-pair product. This PCR product can be directly sequenced, permitting the elucidation of the remaining nucleotides up to the 3 of the mature GAM RNA oligonucleotide adjacent to the 3 adapter. Alternatively, following analysis of the diagnostic PCR reaction on an agarose gel, positive ligation reactions (containing a band of the expected size) were transformed into E. coli. Using this same diagnostic technique and as an alternative to screening by Southern-blot colony-hybridization, transformed bacterial colonies were screened by colony-PCR (Gussow, D. and Clackson, T, Nucleic Acids Res. 17: 4000 (1989)) prior to plasmid purification and sequencing.

Reference is now made to FIG. 22B which is a table summarizing laboratory results which validate the expression of 8 known human miRNA oligonucleotides and 43 novel GAM oligonucleotides detected by the BIOINFORMATIC OLIGONUCLEOTIDE DETECTION ENGINE 100. The table gives additional information on the above GAM oligonucleotides and contains the following fields: NUMBER: refers to the hybridization picture number of FIG. 22A; NAME: indicates the known MIR name for the reference set, or the GAM's name as given by RosettaGenomics nomenclature method; SEQUENCE: 5' to 3' sequence of the mature, 'diced' oligonucleotide; SEQUENCED: '+' indicates the additional validation of the GAM RNA sequence by sequencing procedure as described hereinabove with reference to FIG. 22A.

Figures 23A, 23B, 23C:
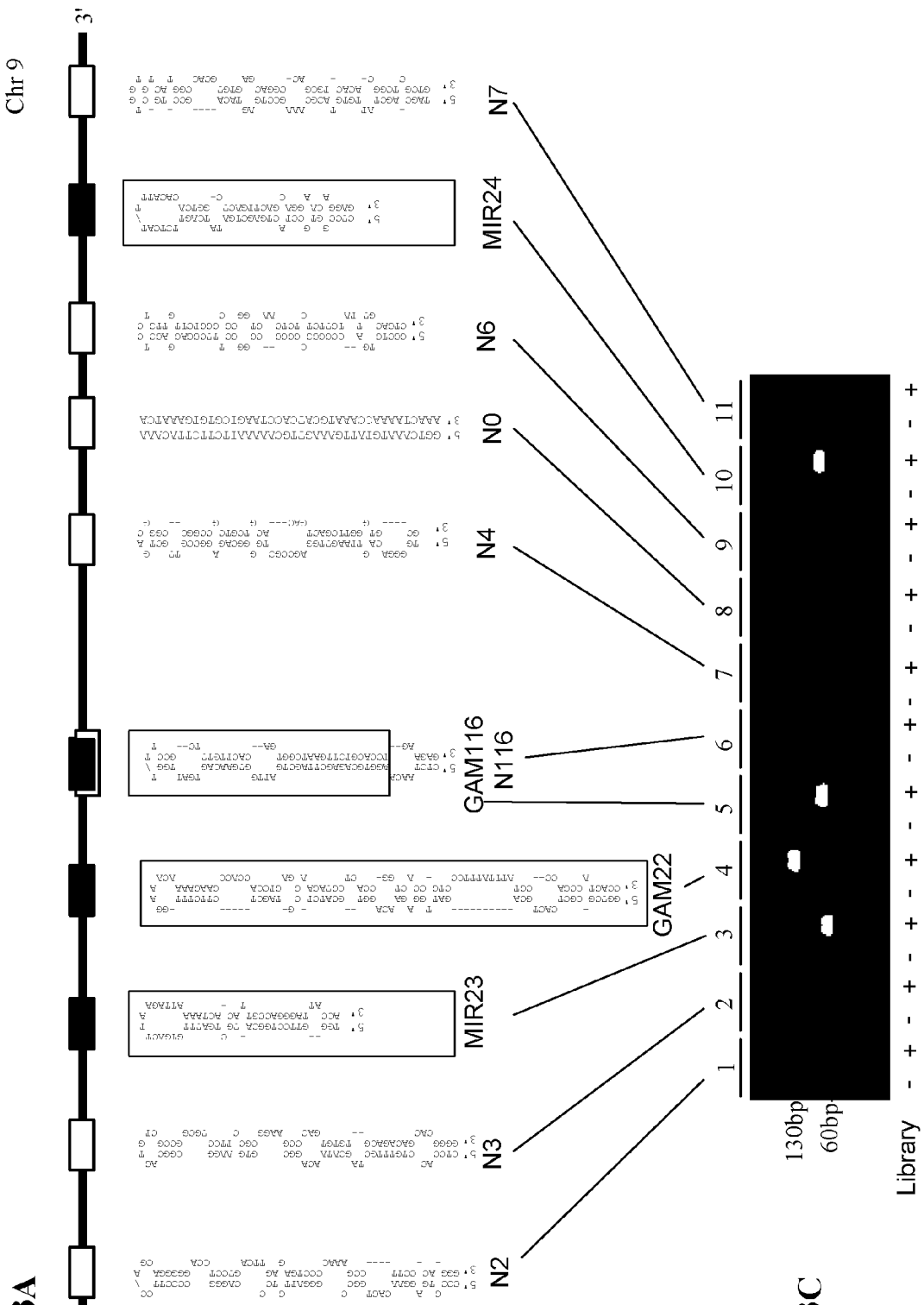
FIG. 23A is a schematic representation of an "operon-like" cluster of novel human hairpin sequences detected bioinformatically by a bioinformatic oligonucleotide detection engine constructed and operative in accordance with a preferred embodiment of the present invention, and non-GAM hairpin useful as negative controls thereto.
FIG. 23B is a schematic representation of secondary folding of hairpins of the operon-like cluster of FIG. 23A. The hairpins are associated with the following SEQ ID NOs: N2 (SEQ ID NO: 2254563); N3 (SEQ ID NO: 2254564); MIR23 (SEQ ID NO: 2254565); GAM22 (SEQ ID NO: 2254566); GAM116 (SEQ ID NOs: 2254567 and 2254568); N4 (SEQ ID NO: 2254569; N0 (SEQ ID NO: 2254570): N6 (SEQ ID NO: 2254571); MIR24 (SEQ ID NO: 2254572); N7 (SEQ ID NO: 2254573)
FIG. 23C is a picture of laboratory results demonstrating expression of novel oligonucleotides of FIGS. 23A and 23B, and lack of expression of the negative controls, thereby validating efficacy of bioinformatic detection of GAM oligonucleotides and GR polynucleotides detected by a bioinformatic oligonucleotide detection engine, constructed and operative in accordance with a preferred embodiment of the present invention.

Reference is now made to FIG. 23A, which is a schematic representation of a novel human GR polynucleotide herein designated GR12731 (RosettaGenomics Ltd. nomenclature), located on chromosome 9, comprising 2 known human MIR oligonucleotides—MIR24 and MIR23, and 2 novel GAM oligonucleotides, herein designated GAM22 and GAM116, all marked by solid black boxes. FIG. 23A also schematically illustrates 6 non-GAM hairpin sequences, and one non-hairpin sequence, all marked by white boxes, and serving as negative controls. By "non-GAM hairpin sequences" is meant sequences of a similar length to known MIR PRECURSOR sequences, which form hairpin secondary folding pattern similar to MIR PRECURSOR hairpins, and yet which are assessed by the BIOINFORMATIC OLIGONUCLEOTIDE DETECTION ENGINE 100 not to be valid GAM PRECURSOR hairpins. It is appreciated that FIG. 23A is a simplified schematic representation, reflecting only the order in which the segments of interest appear relative to one another, and not a proportional distance between the segments.

Reference is now made to FIG. 23B, which is a schematic representation of secondary folding of each of the MIRs and GAMs of GR GR12731 MIR24, MIR23, GAM22 and GAM116, and of the negative control non-GAM hairpins, herein designated N2, N3, N116, N4, N6 and N7. N0 is a non-hairpin control, of a similar length to that of known MIR PRECURSOR hairpins. It is appreciated that the negative controls are situated adjacent to and in between real MIR oligonucleotides and GAM predicted oligonucleotides and demonstrates similar secondary folding patterns to that of known MIRs and GAMs.

Reference is now made to FIG. 23C, which is a picture of laboratory results of a PCR test upon a YM100 size-fractionated "ligation"-library, utilizing a set of specific primer pairs located directly inside the boundaries of the hairpins. Due to the nature of the library the only PCR amplifiable products can result from RNaseIII type enzyme cleaved RNA, as expected for legitimate hairpin precursors presumed to be produced by DROSHA (Lee et al, Nature 425 415-419, 2003). FIG. 23C demonstrates expression of hairpin precursors of known MIR oligonucleotides—MIRhsa-23 and MIRhsa-24, and of novel bioinformatically detected GAM22 and GAM116 hairpins predicted bioinformatically by a system constructed and operative in accordance with a preferred embodiment of the present invention. FIG. 23C also shows that none of the 7 controls (6 hairpins designated N2, N3, N23, N4, N6 and N7 and 1 non-hairpin sequence designated N0) were expressed. N116 is a negative control sequence partially overlapping GAM116.

In the picture, test lanes including template are designated "+" and the control lane is designated "−". The control reaction contained all the components of the test reaction except library template. It is appreciated that for each of the tested hairpins, a clear PCR band appears in the test ("+") lane, but not in the control ("−") lane.

FIGS. 23A through 23C, when taken together validate the efficacy of the bioinformatic oligonucleotide detection engine in: (a) detecting known MIR oligonucleotides; (b) detecting novel GAM PRECURSOR hairpins which are found adjacent to these MIR oligonucleotides, and which despite exhaustive prior biological efforts and bioinformatic detection efforts, went undetected; (c) discerning between GAM (or MIR) PRECURSOR hairpins, and non-GAM hairpins.

It is appreciated that the ability to discern GAM-hairpins from non-GAM-hairpins is very significant in detecting GAM oligonucleotides since hairpins are highly abundant in the genome. Other MIR prediction programs have not been able to address this challenge successfully.

Reference is now made to FIG. 24A which is an annotated sequence of an EST comprising a novel GAM oligonucleotides detected by the oligonucleotide detection system of the present invention. FIG. 24A shows the nucleotide sequence of a known human non-protein coding EST (Expressed Sequence Tag), identified as EST72223. The EST72223 clone obtained from TIGR database (Kirkness and Kerlavage, 1997) was sequenced to yield the above 705 bp transcript with a polyadenyl tail. It is appreciated that the sequence of this EST comprises sequences of one known miRNA oligonucleotide, identified as hsa-MIR98, and of one novel GAM oligonucleotide referred to here as GAM25, detected by the BIOINFORMATIC OLIGONUCLEOTIDE DETECTION ENGINE 100 (FIG. 9) of the present invention.

The sequences of the precursors of the known MIR98 and of the predicted GAM25 precursors are marked in bold, the sequences of the established miRNA 98 and of the predicted miRNA-like oligonucleotide GAM25 are underlined.

Reference is now made to FIGS. 24B, 24C and 24D that are pictures of laboratory results, which when taken together demonstrate laboratory confirmation of expression of the bioinformatically detected novel oligonucleotide of FIG. 24A. In two parallel experiments, an enzymatically synthesized capped, EST72223 RNA transcript, was incubated with Hela S100 lysate for 0 minutes, 4 hours and 24 hours. RNA was subsequently harvested, run on a denaturing polyacrylamide gel, and reacted with either a 102 nt antisense MIR98 probe or a 145 nt antisenseGAM25 precursor transcript probe respectively. The Northern blot results of these experiments demonstrated processing of EST72223 RNA by Hela lysate (lanes 2-4, in 24B and 24C), into ~80 bp and ~22 bp segments, which reacted with the MIR98 precursor probe (24B), and into ~100 bp and ~24 bp segments, which reacted with the GAM25 precursor probe (24C). These results demonstrate the processing of EST72223 by Hela lysate into MIR98 precursor and GAM25 precursor. It is also appreciated from FIG. 24C (lane 1) that Hela lysate itself reacted with the GAM25 precursor probe, in a number of bands, including a ~100 bp band, indicating that GAM25-precursor is endogenously expressed in Hela cells. The presence of additional bands, higher than 100 bp in lanes 5-9 probably corresponds to the presence of nucleotide sequences in Hela lysate, which contain the GAM25 sequence.

In addition, in order to demonstrate the kinetics and specificity of the processing of MIR98 and GAM25 precursors into their respective mature, 'diced' segments, transcripts of MIR98 and of the bioinformatically predicted GAM25 precursors were similarly incubated with Hela S100 lysate, for 0 minutes, 30 minutes, 1 hour and 24 hours, and for 24 hours with the addition of EDTA, added to inhibit Dicer activity, following which RNA was harvested, run on a polyacrylamide gel and reacted with MIR98 and GAM25 precursor probes. Capped transcripts were prepared for in-vitro RNA cleavage assays with T7 RNA polymerase, including a m7G (5')ppp(5')G-capping reaction using the T7-mMessage mMachine kit (Ambion). Purified PCR products were used as template for the reaction. These were amplified for each assay with specific primers containing a T7 promoter at the 5 end and a T3 RNA polymerase promoter at the 3end. Capped RNA transcripts were incubated at 30 C in supplemented, dialysis concentrated, Hela S100 cytoplasmic extract (4C Biotech, Seneffe, Belgium). The Hela S100 was supplemented by dialysis to a final concentration of 20 mM Hepes, 100 mM KCl, 2.5 mM MgCl2, 0.5 mM DTT, 20% glycerol and protease inhibitor cocktail tablets (Complete mini Roche Molecular Biochemicals). After addition of all components, final concentrations were 100 mM capped target RNA, 2 mM ATP, 0.2 mM GTP, 500 U/ml RNasin, 25 g/ml creatine kinase, 25 mM creatine phosphate, 2.5 mM DTT and 50% S100 extract. Proteinase K, used to enhance Dicer activity (Zhang et al., EMBO J. 21, 5875-5885 (2002)) was dissolved in 50 mM Tris-HCl pH 8, 5 mM CaCl2, and 50% glycerol, was added to a final concentration of 0.6 mg/ml. Cleavage reactions were stopped by the addition of 8 volumes of proteinase K buffer (200 Mm Tris-Hcl, pH 7.5, 25 m M EDTA, 300 mM NaCl, and 2% SDS) and incubated at 65 C for 15 min at different time points (0, 0.5, 1, 4, 24 h) and subjected to phenol/chloroform extraction. Pellets were dissolved in water and kept frozen. Samples were analyzed on a segmented half 6%, half 13% polyacrylamide 1XTBE-7M Urea gel.

The Northern blot results of these experiments demonstrated an accumulation of a ~22 bp segment which reacted with the MIR98 precursor probe, and of a ~24 bp segment which reacted with the GAM25 precursor probe, over time (lanes 5-8). Absence of these segments when incubated with EDTA (lane 9), which is known to inhibit Dicer enzyme (Zhang et al., 2002), supports the notion that the processing of MIR98 and GAM25 precursors into their 'diced' segments is mediated by Dicer enzyme, found in Hela lysate. Other RNases do not utilize divalent cations and are thus not inhibited by EDTA. The molecular sizes of EST72223, MIR-98 and GAM25 and their corresponding precursors are indicated by arrows.

FIG. 24D present Northern blot results of same above experiments with GAM25 probe (24 nt). The results clearly demonstrated the accumulation of mature GAM25 oligonucleotide after 24 h.

To validate the identity of the band shown by the lower arrow in FIGS. 24C and 24D, a RNA band parallel to a marker of 24 base was excised from the gel and cloned as in Elbashir et al (2001) and sequenced. 90 clones corresponded to the sequence of mature GAM25 oligonucleotide, three corresponded to GAM25*(the opposite arm of the hairpin with a 1-3 nucleotide 3 overhang) and two to the hairpin-loop.

GAM25 was also validated endogenously by sequencing from both sides from a HeLa YM100 total-RNA "ligation" libraries, utilizing hemispecific primers as described in FIG. 22.

Taken together, these results validate the presence and processing of a novel MIR-like oligonucleotide, GAM25, which was predicted bioinformatically. The processing of this novel GAM oligonucleotide product, by Hela lysate from EST72223, through its precursor, to its final form was similar to that observed for known miRNA oligonucleotide, MIR98.

Transcript products were 705 nt (EST72223), 102 nt (MIR98 precursor), 125 nt (GAM25 precursor) long. EST72223 was PCR amplified with T7-EST 72223 forward primer: 5-TAATACGACTCACTATAGGCCCTTATFA-GAGGATTCTGCT-3 (SEQ ID NO: 2254583) and T3-EST72223 reverse primer: "-AATTAACCCTCAC-TAAAGGTTTTTTTTTCCTGAGACAGAG T-3 (SEQ ID NO: 2254584). MIR98 was PCR amplified using EST72223 as a template with T7MIR98 forward primer: 5-TAATAC-GACTCACTATAGGGTGAGGTAGTAAGTTGTATT GTT-3 (SEQ ID NO: 2254585) and T3MIR98 reverse primer: 5-AATTAACCCTCACTAAAGGGAAAGTAG-TAAGTTGTATAGT T-3. (SEQ ID NO: 2254586) GAM25 was PCR amplified using EST72223 as a template with GAM25 forward primer: 5-GAGGCAGGAGAATTGCT-TGA-3 (SEQ ID NO: 2254587) and T3-EST72223 reverse primer: 5-AATTAACCCTCACTAAAGGC CTGAGACA-GAGTCTTGCTC-3 (SEQ ID NO: 2254588).

It is appreciated that the data presented in FIGS. 24A, 24B, 24C and 24D when taken together validate the function of the bioinformatic oligonucleotide detection engine 100 of FIG. 9. FIG. 24A shows a novel GAM oligonucleotide bioinformatically detected by the BIOINFORMATIC OLIGONUCLE-OTIDE DETECTION ENGINE 100, and FIGS. 24C and 24D show laboratory confirmation of the expression of this novel oligonucleotide. This is in accord with the engine training and validation methodology described hereinabove with reference to FIG. 10.

DETAILED DESCRIPTION OF LARGE TABLES

Table 1 comprises data relating the SEQ ID NO of oligonucleotides of the present invention to their corresponding GAM NAME, and contains the following fields: GAM SEQ-ID: GAM SEQ ID NO, as in the Sequence Listing; GAM NAME: Rosetta Genomics Ltd. nomenclature (see below); GAM RNA SEQUENCE: Sequence (5' to 3') of the mature, 'diced' GAM RNA; GAM ORGANISM: identity of the organism encoding the GAM oligonucleotide; GAM POS: Dicer cut location (see below); and Table 2 comprises detailed textual description according to the description of FIG. 8 of each of a plurality of novel GAM oligonucleotides of the present invention, and contains the following fields: GAM NAME: Rosetta Genomics Ltd. nomenclature (see below); GAM ORGANISM: identity of the organism encoding the GAM oligonucleotide; PRECUR SEQ-ID:GAM precursor Seq-ID, as in the Sequence Listing; PRECURSOR SEQUENCE: Sequence (5' to 3) of the GAM precursor; GAM DESCRIPTION: Detailed description of GAM oligonucleotide with reference to FIG. 8; and Table 3 comprises data relating to the source and location of novel GAM oligonucleotides of the present invention, and contains the following fields: GAM NAME: Rosetta Genomics Ltd. nomenclature (see below); PRECUR SEQ-ID: GAM precursor SEQ ID NO, as in the Sequence Listing; GAM ORGANISM: identity of the organism encodes the GAM oligonucleotide; SOURCE: Chromosome encoding a human GAM oligonucleotide; STRAND: Orientation of the strand, '+' for the plus strand, '−' for the minus strand; SRC-START OFFSET: Start offset of GAM precursor sequence relative to the SOURCE; SRC-END OFFSET: End offset of GAM precursor sequence relative to the SOURCE; and Table 4 comprises data relating to GAM precursors of novel GAM oligonucleotides of the present invention, and contains the following fields: GAM NAME: Rosetta Genomics Ltd. nomenclature (see below); PRECUR SEQ-ID: GAM precursor Seq-ID, as in the Sequence Listing; GAM ORGANISM: identity of the organism encoding the GAM oligonucleotide; PRECURSOR-SEQUENCE: GAM precursor nucleotide sequence (5' to 3'); GAM FOLDED PRECUR-SOR RNA: Schematic representation of the GAM folded precursor, beginning 5' end (beginning of upper row) to 3' end (beginning of lower row), where the hairpin loop is positioned at the right part of the draw; and Table 5 comprises data relating to GAM oligonucleotides of the present invention, and contains the following fields: GAM NAME: Rosetta Genomics Ltd. nomenclature (see below); GAM ORGAN-ISM: identity of the organism encoding the GAM oligonucleotide; GAM RNA SEQUENCE: Sequence (5' to 3') of the mature, 'diced' GAM RNA; PRECUR SEQ-ID: GAM precursor Seq-ID, as in the Sequence Listing; GAM POS: Dicer cut location (see below); and Table 6 comprises data relating SEQ ID NO of the GAM target gene binding site sequence to TARGET gene name and target binding site sequence, and contains the following fields: TARGET BINDING SITE SEQ-ID: Target binding site SEQ ID NO, as in the Sequence Listing; TARGET ORGANISM: identity of organism encode the TARGET gene; TARGET: GAM target gene name; TARGET BIND-ING SITE SEQUENCE: Nucleotide sequence (5' to 3') of the target binding site; and Table 7 comprises data relating to target-genes and binding sites of GAM oligonucleotides of the present invention, and contains the following fields: GAM NAME: Rosetta Genomics Ltd. nomenclature (see below); GAM ORGANISM: identity of the organism encoding the GAM oligonucleotide; GAM RNA SEQUENCE: Sequence (5' to 3') of the mature, 'diced' GAM RNA; TARGET: GAM target gene name; TAR-GET REF-ID: Target accession number (GenBank); TAR-GET ORGANISM: identity of organism encode the TAR-GET gene; UTR: Untranslated region of binding site/s (3" or 5"); TARGET BS-SEQ: Nucleotide sequence (5' to 3') of the target binding site; BINDING-SITE-DRAW: Schematic representation of the binding site, upper row represent 5 to 3 sequence of the GAM, Lower row represent 3' to 5N Sequence of the target; GAM POS: Dicer cut location (see below); and Table 8 comprises data relating to functions and utilities of novel GAM oligonucleotides of the present invention, and contains the following fields: GAM NAME: Rosetta Genomics Ltd. nomenclature (see below); GAM RNA SEQUENCE: Sequence (5' to 3') of the mature, 'diced' GAM RNA; GAM ORGANISM: identity of the organism encoding the GAM oligonucleotide; TARGET:GAM target gene name; TAR-GET ORGANISM: identity of organism encode the TAR-GET gene; GAM FUNCTION: Description of the GAM functions and utilities; GAM POS: Dicer cut location (see below); and Table 9 comprises data of gene function references—Bibliography and contains the following fields: GAM NAME: Rosetta Genomics Ltd. nomenclature (see below); GAM RNA SEQUENCE: Sequence (5 to 3) of the mature, 'diced' GAM RNA gene; GAM ORGANISM: identity of the organism encoding the GAM oligonucleotide; TARGET: GAM target gene name; TARGET ORGANISM: identity of organism encode the TARGET gene; REFERENCES: list of references relating to the target gene; GAM POS: Dicer cut location (see below); and Table 10 comprises data relating to novel GR (Genomic Record) polynucleotides of the present invention, and contains the following fields: GR NAME: Rosetta Genomics Ltd.nomenclature (see below); GR ORGANISM: identity of the organism encoding the GR polynucleotide; GR DESCRIPTION: Detailed description of a GR gene cluster, with reference to FIG. 16; and Table 11 comprises data relating to diseases that GAM oligonucleotides are predicted to regulate the disease-associated genes. Each row is referred to a specific disease, and lists the GAM target genes related to the disease. The first row is a summary of ALL diseases containing in the present invention, thus listing ALL GAM target genes relating to theses diseases. The table contains the following fields: ROW #: index of the row number; DISEASE NAME: name of the disease; TARGET-GENES ASSOCIATED WITH DISEASE: list of GAM target genes that are associated with the specified disease; and The following conventions and abbreviations are used in the tables: The nucleotide 'U' is represented as 'T' in the tables, and GAM NAME or GR NAME are names for nucleotide sequences of the present invention given by RosettaGenomics Ltd. nomenclature method. All GAMs/GRs are designated by GAMx/GRx where x is a unique ID.

GAM POS is a position of the GAM RNA on the GAM PRECURSOR RNA sequence. This position is the Dicer cut location: A indicates a probable Dicer cut location; B indicates an alternative Dicer cut location.

All human nucleotide sequences of the present invention as well as their chromosomal location and strand orientation are derived from sequence records of UCSC-hg16 version, which is based on NCBI, Build34 database (April, 2003).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07655785B1). An electronic copy of the "Sequence Listing" will also be available from the USPTO upon request and payment of the fee set forth in 37 CFR 1.19(b)(3).

The invention claimed is:

1. An isolated nucleic acid consisting of X nucleotides wherein the sequence of the nucleic acid comprises:
    (a) Y consecutive nucleotides of SEQ ID NO: 2240728;
    (b) a DNA equivalent of (a); or
    (c) the complement of (a) or (b),
wherein,
X=16 to 120,
Y≧16, and
X≧Y.

2. The nucleic acid of claim 1, wherein the Y nucleotides comprises the sequence of SEQ ID NO: 8385.

3. The nucleic acid of claim 1, wherein X=19 to 24 nucleotides.

4. The nucleic acid of claim 1, wherein X=Y.

5. The nucleic acid of claim 4, wherein the Y consecutive nucleotides is SEQ ID NO: 2240728.

6. The nucleic acid of claim 4, wherein the Y consecutive nucleotides is SEQ ID NO: 8385.

7. A vector comprising a human insert, wherein the human insert consists of the nucleic acid of claim 1, and wherein the vector comprises no other insert but the nucleic acid of claim 1.

8. A vector comprising a human insert, wherein the human insert consists of the nucleic acid of claim 2, and wherein the vector comprises no other insert but the nucleic acid of claim 2.

9. A vector comprising a human insert, wherein the human insert consists of the nucleic acid of claim 3, and wherein the vector comprises no other insert but the nucleic acid of claim 3.

10. A vector comprising a human insert, wherein the human insert consists of the nucleic acid of claim 4, and wherein the vector comprises no other insert but the nucleic acid of claim 4.

11. A vector comprising a human insert, wherein the human insert consists of the nucleic acid of claim 5, and wherein the vector comprises no other insert but the nucleic acid of claim 5.

12. A vector comprising a human insert, wherein the human insert consists of the nucleic acid of claim 6, and wherein the vector comprises no other insert but the nucleic acid of claim 6.

13. The isolated nucleic acid of claim 1, wherein the nucleic acid is a probe.

14. The isolated nucleic acid of claim 2, wherein the nucleic acid is a probe.

15. The isolated nucleic acid of claim 3, wherein the nucleic acid is a probe.

16. The isolated nucleic acid of claim 4, wherein the nucleic acid is a probe.

17. The isolated nucleic acid of claim 5, wherein the nucleic acid is a probe.

18. The isolated nucleic acid of claim 6, wherein the nucleic acid is a probe.

* * * * *